US006599873B1

(12) United States Patent
Sommer et al.

(10) Patent No.: US 6,599,873 B1
(45) Date of Patent: Jul. 29, 2003

(54) INTERLEUKIN-1 INHIBITORS, COMPOSITIONS, AND METHODS OF TREATMENT

(75) Inventors: Andreas Sommer, Concord, CA (US); Charles H. Hannum, Boulder, CO (US); Stephen P. Eisenburg, Boulder, CO (US); Robert C. Thompson, Boulder, CO (US); William P. Arend, Denver, CO (US); Fenneke G. Joslin, Denver, CO (US)

(73) Assignees: Amgen Inc., Thousand Oaks, CA (US); The Regents of the University of Colorado, Boulder, CO (US)

( * ) Notice: Subject to any disclaimer, the term of this patent is extended or adjusted under 35 U.S.C. 154(b) by 0 days.

(21) Appl. No.: 08/468,425

(22) Filed: Jun. 6, 1995

Related U.S. Application Data

(60) Division of application No. 08/304,437, filed on Sep. 12, 1994, which is a continuation of application No. 07/987,992, filed on Dec. 9, 1992, now abandoned, which is a continuation of application No. 07/685,818, filed on Apr. 15, 1991, now abandoned, which is a division of application No. 07/506,522, filed on Apr. 6, 1990, now Pat. No. 5,075,222, which is a continuation of application No. 07/266,531, filed on Nov. 3, 1988, now abandoned, which is a continuation-in-part of application No. 07/248,521, filed on Sep. 23, 1988, now abandoned, which is a continuation-in-part of application No. 07/238,713, filed on Aug. 31, 1988, now abandoned, which is a continuation-in-part of application No. 07/199,915, filed on May 27, 1988.

(51) Int. Cl.⁷ .............................................. A61K 38/17
(52) U.S. Cl. .................. 514/2; 514/4; 514/8; 530/350; 530/351; 435/69.1; 435/69.8; 435/356; 435/358; 435/361; 435/252.33; 435/254.2
(58) Field of Search ................................ 530/350, 351; 424/529–545; 514/2, 4, 8; 435/69.1, 69.52, 172.1, 69.8, 356, 358, 361, 253.33, 254.2

(56) References Cited

U.S. PATENT DOCUMENTS

| | | | |
|---|---|---|---|
| 4,968,607 A | | 11/1990 | Dower et al. |
| 5,075,222 A | * | 12/1991 | Hannum et al. |
| 5,359,032 A | | 10/1994 | Dayer et al. ............ 530/350 |
| 5,453,490 A | | 9/1995 | Hageman et al. |
| 5,455,330 A | | 10/1995 | Haskill et al. |
| 5,508,262 A | | 4/1996 | Norman, Jr. |
| 5,739,282 A | * | 4/1998 | Colotta et al. |
| 5,747,072 A | | 5/1998 | Davidson et al. |
| 5,747,444 A | | 5/1998 | Haskill et al. |
| 5,770,401 A | | 6/1998 | Mullarkey |
| 5,972,880 A | * | 10/1999 | Pelletier et al. |
| 6,096,728 A | * | 8/2000 | Collins et al. |
| 6,159,460 A | * | 12/2000 | Thompson et al. |

FOREIGN PATENT DOCUMENTS

| | | |
|---|---|---|
| EP | 0 341 273 B1 | 3/1989 |
| EP | 0 398 817 A1 | 11/1990 |
| EP | 0 343 684 B1 | 4/1993 |
| WO | WO 88/10299 | 12/1988 |
| WO | WO 89/01946 | 3/1989 |
| WO | WO 89/11540 | 11/1989 |
| WO | WO 91/00742 | 1/1991 |
| WO | WO 91/08285 | 6/1991 |
| WO | WO 91/17184 | 11/1991 |
| WO | WO 91/17249 | 11/1991 |
| WO | WO 92/12724 | 8/1992 |
| WO | WO 92/16221 | 10/1992 |
| WO | WO 93/02692 | 2/1993 |
| WO | WO 93/07863 | 4/1993 |
| WO | WO 93/08304 | 4/1993 |
| WO | WO 93/08819 | 5/1993 |
| WO | WO 93/08820 | 5/1993 |
| WO | WO 93/18783 | 9/1993 |
| WO | WO 93/21946 | 11/1993 |
| WO | WO 93/24134 | 12/1993 |
| WO | WO 94/06457 | 3/1994 |
| WO | WO 94/20517 | 9/1994 |
| WO | WO 94/21235 | 9/1994 |
| WO | WO 94/21275 | 9/1994 |
| WO | WO 95/10298 | 4/1995 |
| WO | WO 95/16353 | 6/1995 |
| WO | WO 95/16706 | 6/1995 |
| WO | WO 96/09323 | 3/1996 |

OTHER PUBLICATIONS

Heimberg H., et al., Inhibition of cytokine–induced NF–kappaB activation by adenovirus–mediated expression of a NF–kappaB super–repressor prevents beta–cell apoptosis. Diabetes Oct. 2001, 50 (10) p2219–24.*
Chen G. et al. Expression of the transcription factor STAT–1 alpha in insulinoma cells protects against cytotoxic effects of multiple cytokines. Journal of biological chemistry, Jan. 5, 2001, 276 (1) p766–72.*
Losa Garcia JE et al., Evaluation of inflammatory cytokine secretion by human alveolar macrophages. Mediators of inflammation (ENGLAND) 1999, 8 (1) p43–51.*
Losa Garcia Je et al., Effect of cyclosporin A on inflammatory cytokine production by human alveolar macrophages. Respiratory medicine (ENGLAND) May 1998, 92 (5) p722–8.*
Mikuniya T. et al., Quantitative evaluation of the IL–1 beta and IL–1 receptor antagonist obtained from BALF macrophages in patients with interstitial lung diseases. Sarcoidosis, vasculitis, and diffuse lung diseases (ITALY) Mar. 1997, 14 (1) p39–45.*
Smith DR et al., Increased interleukin–1 receptor antagonist in idiopathic pulmonary fibrosis. A compartmental analysis. American journal of respiratory and critical care medicine (UNITED STATES) Jun. 1995, 151 (6) p1965–73.*

(List continued on next page.)

Primary Examiner—Lorraine Spector
(74) Attorney, Agent, or Firm—Finnegan, Henderson, Farabow, Garrett & Dunner, LLP

(57) ABSTRACT

Interleukin-1 inhibitors are provided. Compositions comprising an interleukin-1 inhibitor are provided. Methods of treating a patient comprising administering an interleukin-1 inhibitor are provided.

296 Claims, 22 Drawing Sheets

OTHER PUBLICATIONS

Janson RW et al., Enhanced production of IL–1 receptor antagonist by alveolar macrophages from patients with interstitial lung disease. American review of respiratory disease Aug. 1993, 148 (2) p495–503.*

Kline JN et al., Relative release of interleukin–1 beta and interleukin–1 receptor antagonist by alveolar macrophages. A study in asbestos–induced lung disease, sarcoidosis, and idiopathic pulmonary fibrosis. Chest Jul. 1993, 104 (1) p47–53.*

Fireman E et al., Suppressive activity of alveolar macrophages and blood monocytes from interstitial lung diseases: role of released soluble factors. International journal of immunopharmacology (ENGLAND) 1989, 11 (7) p751–60.*

Johnston CJ et al., Early and persistent alterations in the expression of interleukin–1 alpha, interleukin–1 beta and tumor necrosis factor alpha mRNA levels in fibrosis–resistant and sensitive mice after thoracic irradiation. Radiation research Jun. 1996, 145 (6) p762–7.*

Chen CC et al., Interleukin–1 beta in oral submucous fibrosis, verrucous hyperplasia and squamous cell carcinoma tissues. Kaohsiung journal of medical sciences (CHINA(REPUBLIC: 1949–)) Sep. 1999, 15 (9) p513–9.*

Nikolic–Paterson DJ et al., Interleukin–1 in renal fibrosis. Kidney international. Supplement May 1996, 54 p588–90.*

Rameshwar P et al., Implication of CD44 in adhesion–mediated overproduction of TGF–beta and IL–1 in monocytes from patients with bone marrow fibrosis. British journal of haematology (ENGLAND) Apr. 1996, 93 (1) p22–9.*

Mancini R et al., An interleukin–1 receptor antagonist decreases fibrosis induced by dimethylnitrosamine in rat liver. Virchows Archiv (GERMANY) 1994, 424 (1) p25–31.*

Piguet PF et al, Interleukin 1 receptor antagonist (IL–1ra) prevents or cures pulmonary fibrosis elicited in mice by bleomycin or silica. Cytokine Jan. 1993, 5 (1) p57–61.*

Pacifici R et al., Spontaneous release of interleukin 1 from human blood monocytes reflects bone formation in idiopathic osteoporosis. Proceedings of the National Academy of Sciences of the United States of America Jul. 1987, 84 (13) p4616–20.*

Abrahamsen B et al., Cytokines and bone loss in a 5–year longitudinal study—hormone replacement therapy suppresses serum soluble interleukin–6 receptor and increases interleukin–1–receptor antagonist: the Danish Osteoporosis Prevention Study. Journal of bone and mineral research (UNITED STATES) Aug. 2000, 15 (8) p1545–54.*

Cooper KD et al. Interleukin–1 in human skin: dysregulation in psoriasis. Journal of investigative dermatology Nov. 1990, 95 (5) p24S–26S.*

Takematsu H et al., Lack of correlation between interleukin 6 and interleukin 1 levels in psoriatic lesional skin.Tohoku journal of experimental medicine (JAPAN) Mar. 1994, 172 (3) p243–52.*

Bernstein SH et al., A phase I study of recombinant human soluble interleukin–1 receptor (rhu IL–1R) in patients with relapsed and refractory acute myeloid leukemia. Cancer chemotherapy and pharmacology (GERMANY) 1999, 43 (2) p141–4.*

Notice of Opposition to a European Patent (European Patent No. 341273 B1) and Facts And Arguments Supporting The Opposition Against European Patent No. 341273 B1, filed by Amgen Inc., dated Oct. 8, 1997.

Official Communication, and Letter From The Proprietor (Biogen) including Observation Under Article 101(2) EPC (Observations to the Opposition filed by Amgen Inc.), dated Aug. 4, 1998.

Summons To Attend Oral Proceedings Pursuant To Rule 71(1) EPC, including Preliminary Opinion, dated Jul. 11, 2000.

Response To The Official Communication dated Aug. 4, 1998; and the Preliminary Opinion dated Jul. 11, 2000, filed by Amgen, dated Jan. 8, 2001.

Letter to European Patent Office from Amgen, dated Feb. 6, 2001.

Letter to European Patent Office from Biogen, including Observations Of The Patent Proprietor In Response To The Opponent's Letter Dated Jan. 8, 2001, dated Feb. 6, 2001.

Letter to European Patent Office from Amgen, dated Feb. 22, 2001.

Letter to European Patent Office from Biogen, dated Feb. 27, 2001.

Minutes of Oral Proceeding dated Mar. 19, 2001.

Decision Revoking the European Patent (Art. 102(1), (3) EPC), dated May 25, 2001.

Notice that the Patent Proprietor filed an appeal, dated Jul. 25, 2001.

Notice of Appeal pursuant to Article 108 EPC, dated Jul. 12, 2001.

Communication from European Patent Office enclosing a copy of the statement setting out the grounds of appeal, dated Oct. 12, 2001.

Letter to European Patent Office from Biogen, dated Oct. 3, 2001.

Statement Of Grounds Of Appeal, dated Oct. 3, 2001.

Balavoine et al., "Collagense– and $PGE_2$–Stimulating Activity (Interleukin–1–Like) and Inhibitors in Urine from a Patient with Monocytic Leukemia", The Physiologic, Metabolic, and Immunologic Actions of Interleukin–1, pp. 429–436 (1985).

Dayer et al., "Collagenase–and PGE2– Stimulating Activity (Interleukin–1–Like) and Inhibitors(s) in Human Urine", J. Leukocyte Biology, 37, p. 693 (Jun. 1985).

Gearing et al., "A simple sensitive bioassay for interleukin–1 which is unresponsive to $10^3$ U/ml of interleukin–1", J. Immunol. Methods, 99:7–11 (1987).

Urdal et al., "Affinity purification and chemical analysis of the interleukin–1 receptor", J. Biol. Chem., 263:2870–2877 (1988).

Arend et al., "An IL–1 Inhibitor from Human Monocytes", J. Immunol., 143(6):1851–1858 (1989).

Balavoine et al., "Identification of Interleukin 1–like Activity and Inhibitor(s) in Urine from a Patient with Acute Monoblastic Leukemia", Lymphokine Res., 3(4):233A (Abstract) (1984).

Bienkowski et al., "Purification and Characterization of Interleukin 1 Receptor Level Antagonist Proteins from THP–1 Cells", J. Biol. Chem., 265(24):14505–14511 (1990).

Biotechnology Bulletin (1994) Jul. 31, 1994, 13(6):2 (100–199 words).

Bulletin International d'Informations (Droit et Pharmacie), Sep. 21, 1994, 8/9 p. 89(100–199 words).

Cannon et al., "Circulating Interleukin–1 and Tumor Necrosis Factor in Septic Shock and Experimental Endotoxin Fever", Journal of Infectious Diseases, 161:79–84 (1990).

Carter et al., "Purification, cloning, expression and biological characterization of an interleukin–1 receptor antagonist protein", Nature, 344:633–638 (1990).

Catalano, "Clinical Use of Human Recombinant IL–1 Receptor Antagonist", Keystone Symposium on Cytokines and Cytokine Receptors, Jan. 31–Feb. 7, 1993, p. 55 (Abstract No. E016).

Cominelli et al., "Interleukin–1 in the pathogenesis of and protection from inflammatory bowel disease", Biotherapy, 1(4):369–375 (1989).

Cominelli et al., "Regulation of Eicosanoid Production in Rabbit Colon by Interleukin–1", Gastroenterology, 97(6):1400–1405 (1989).

Cominelli et al., "Interleukin 1 (IL–1) Gene Expression, Synthesis, and Effect of Specific IL–1 Receptor Blockade in Rabbit Immune Complex Colitis", J. Clin. Invest., 86:972–980 (1990).

Conti et al.,"Human Recombinant Interleukin–1 Receptor Antagonist (hrIL–1ra) Enhances the Stimulatory Effect of Interleukin–2 on Natural Killer Cell Activity Against Molt–4 Target Cells", Int. J. Immunopharmac 14(6):987–993 (1992).

Dinarello, "Interleukin–1 and Interleukin–1 Antagonism", Blood, 77(8):1627–1652 (1991).

Dinarello et al., "Interleukin–1", Digestive Diseases & Sciences, 33(3):25S–35S (1988).

Eichacker et al., "The Effects of Human Recombinant Interleukin–1 (IL–1) on Canine Alveolar Neutrophil(N) Number and Lung Function", Critical Care Medicine, Apr. 1989, p. S58 (Abstract).

Ferrara, "The Role of Interleukin 1 (IL–1) and IL–1 Receptor Antagonist in Graft–Versus–Host Disease", Keystone Symposium on Cellular Immunity & the Immuno–therapy of Cancer, Mar. 17–24, 1993, p. 96 (Abstract No. NZ 019).

Girardin et al., "Tumor Necrosis Factor and Interleukin–1 in the Serum of Children with Severe Infectious Purpura", New England Journal of Medicine, 319(7):397–400 (1988).

Locksley et al., "Release of Interleukin 1 Inhibitory Activity (Contra–IL–1) by Human Monocyte–derived Macrophages Infected with Human Immunodeficiency Virus In Vitro and In Vivo", J. Clin. Invest., 82:2097–2105 (Dec. 1988).

Lotz et al., "Characterization of Interleukin–1 Inhibitors in Rheumatoid Synovial Fluid", Arthritis Rheum., 29:S38 (Abstract No. 162) (1986).

Maniatis, "Strategies for cDNA Cloning" and "Construction of Genomic Libraries in Bacteriophage γ Vectors" and "Hybridization of Southern Filters", Molecular Cloning, A Laboratory Manual, Cold Springs Harbor Laboratory, CSH, NY, pp. 224–228 (1982).

Mazzei et al., "Purification and Characterization of a 26–kDa Competitive Inhibitor of Interleukin 1," Eur. J. Immunol., 20:683–689 (1990).

Moldawer, "Interleukin–1, TNFa and Their Naturally Occurring Antagonists in Sepsis", Blood Purif., 11:128–133 (1993).

Moonen et al. , "Bioassay for interleukin–1 Inhibitors", Chem. Abstr., 107:587 (Abstract 234307K) (1987).

Ohlsson et al., "Interleukin–1 receptor antagonist reduces mortality from endotoxin shock", Nature:348:550–552 (1990).

Okusawa et al., "Interleukin 1 induces a Shock–like State in Rabbits", J. Clin. Invest., 81:1162–1172 (1988).

Piguet et al., "Interleukin 1 Receptor Antagonist (IL–1ra) Prevents or Cures Pulmonary Fibrosis Elicited in Mice by Bleomycin or Silica", Cytokine, 5(1):57–61 (1993).

Poli et al., "Interleukin 1 induces expression of the human immunodeficiency virus alone and in synergy with interleukin 6 in chronically infected U1 cells: Inhibition of inductive effects by the interleukin 1 receptor antagonist", Proc. Natl. Acad. Sci. USA, 91:108–112 (1994).

Relton & Rothwell, "Interleukin–1 Receptor Antagonist Inhibits Ischaemic and Excitotoxic Neuronal Damage in the Rat", Brain Research Bulletin, 29:243–246 (1992).

Roberts et al., "Interleukin–1 and Inhibitor Production by Human Macrophages Exposed to Influenza Virus or Respiratory Syncytial Virus", The Physiologic, Metabolic, and Immunologic Actions of Interleukin–1, Proceeding of a Symposium Held in Ann Arbor, Michigan, Jun. 4–6, 1985, pp. 409–418, Alan R. Liss Inc. publisher (1985).

Rolfe et al., "Interleukin–1 Receptor Antagonist Expression in Sarcoidosis", Am. Rev. Respir. Dis., 148:1378–1384 (1993).

Rosenstriech et al., "Studies on a Urine Derived Human Interleukin–1 Inhibitor", The Physiologic, Metabolic, and Immunologic Actions of Interleukin–1, Proceeding of a Symposium Held in Ann Arbor, Michigan, Jun. 4–6, 1985, pp. 419–428.

Rothwell & Relton, "Involvement of Cytokines in Acute Neurodegeneration in the CNS", Neurosci. Biobehav. Rev., 17:217–227 (1993).

Scala G., Matsushima K., Oppenheim J.J., "Inhibitory cells and factors that regulate the production and activities of interleukin 1 IL–1", Serono symposia publications from Raven Press, vol. 23, Immunopharmacology, editors, Peter A. Miescher, L. Bolis, M. Ghione. New York, pp. 41–50 (1985).

Seckinger et al., "Natural and Recombinant Human IL–1 Receptor Antagonists Block the Effects of IL–1 on Bone Resorption and Prostaglandin Production", J. Immunol., 145(12)4181–4184 (1990).

Sofer, "Chromatographic Removal of Pyrogens", Bio/Technology, Dec.:1035–1038 (1984).

Stimpson et al., "Exacerbation of Arthritis by IL–1 in Rat Joints Previously Injured by Peptidoglycan–Polysaccharide", J. Immunol., 140:2964–2969 (1988).

Sullivan et al., "Inhibition of the Inflammatory Action of Interleukin–1 and Tumor Necrosis Factor (Alpha) on Neutrophil Function by Pentoxifylline", Infection & Immunity, 56(7):1722–1729 (1988).

Thomas et al., "Evaluation of an interleukin–1 receptor antagonist in the rat acetic acid–induced colitis model", Agents & Action, 34:187–190 (1991).

Ulich et al., "The Intratracheal Administration of Endotoxin and Cytokines. III. The Interleukin–1(IL–1) Receptor Antagonist Inhibits Endotoxin– and IL–1–Induced Acute Inflammation", Am. J. Pathology, 138(3):521–524(1991).

van Hilten et al., "A Report on the International Conference on Inflammation Held in Rome, Oct. 6–11, 1991", DN&P, 5(1):59–62 (1992).

Wakabayashi et al., "A specific receptor antagonist for interleukin 1 prevents *Escherichia coli*–induced shock in rabbits", FASEB J., 5(3):338–343 (1991).

Watson et al., Molecular Biology of the Gene, Fourth Edition, Benjamin/Cummings Publishing: Menlo Park, CA, P. 313 (1987).

Wooley et al., "The Effect of an Interleukin–1 Receptor Antagonist Protein on Type II Collagen–induced Arthritis and Antigen–induced Arthritis in Mice", Arthritis & Rheumatism, 36(9):1305–1314 (1993).
Ziegler et al., "Treatment of Gram–Negative Bacteremia and Shock with Human Antiserum to a Mutant *Escherichia coli*", New England Journal of Medicine, 307:1225–1230 (1982).
Balavoine et al., *Lymphokine Res., 3*:233 (1984).
Balavoine et al., J. Clin. Invest., 73:1120–1124 (1986).
Barak et al., Lymphokine Res. 7:Abstract No. 1.32 (Fall 1988).
Beck et al., RES 1987 Annual Meeting (Abstract No. 232).
Brown et al., J. Leukocyte Biol., 37:688–689 (Abstract) (1985).
Dinarello et al., Ann. Rev. Med., 37:173–178 (1986).
Durum et al., Ann. Rev. Immunol., 3:263–287 (1985).
Hill et al., J. Immunol., 137:858–862 (1986).
Kemp et al., J. Immunol. 137:2245–2251 (1986).
Kimball et al., J. Immunol., 133:256–260 (1984).
Korn et al., J. Immunol., 138:3290–3294 (May 15, 1987).
Kupper et al., J. investigative Dermatology, 87:570–573 (1986).
Liao et al., J. Exp. Med. 159:126–136 (1984).
Liao et al., J. Immunol., 134:3882–3886 (1985).
Lomedico et al., Nature, 312:458–462 (1984).
Lotz et al., J. Immunol., 136:3643–3648 (1986).
Moissec et al., Fed. Proc., 44:1262 (Abstract No. 4978) (1985).
Nishihara et al., Infection and Immunity, 56:2801–2807 (1988).
Rodgers et al., J. Virol, 55:527–532 (1985).
Scala et al., J. Exp. Med., 159:1637–1652 (1984).
Scala et al., Lymphokine Res., 3:271 (Abstract) (1984).
Scala et al., "Inhibitory cells and factors that regulate the production and activities of IL–1," ILI Regulatory Factors, pp. 41–50.
Shirahama et al., Scand. J. Immunol., 28:719–725 (1988).
Sissons et al., Clin. Res., 33: (Abstract No. 610A) (1985).
Schnyder et al., J. Immunol., 138:496–503 (Jan. 15, 1987).
Schwarz et al., J. Immunol., 138:1457–1463 (Mar. 1, 1987).
Takahashi et al., "Basal and Clinical Investigation of Urine IL–1 Inhibitor," Hiroshima Univ. Med. J., 35(4):813–842 (1987) (Japanese with English Abstract).
Tiku et al., J. Leukocyte Biol., 37:747–748 (Abstract) (1985).
Tiku et al., Arthrit. Rheum., 29:S98 (Abstract E34) (1986).
Tiku et al., J. Immunol., 136:3677–3685 (1986).
Tiku et al., J. Immunol., 136:3686–3692 (1986).
Tracey et al., J. Leukocyte Biol., 37:750 (Abstract) (1985).
Westley et al., J. Exp. Med., 163:1589–1594 (1986).
Yost et al., J. Allergy Clin. Immunol., 77:230 (Abstract No. 439) (1986).
Roberts et al., J. Exp. Med., 163:511–519 (1986).
Seckinger et al., J. Immunol., 139:1541–1545 (1987).
Hall, Chem. Abstr., 105(17):539, abstract No. 151238W (Diss. Abstr. Int. B, 46(12), pt. 1, 4191 (1986).
Helfman et al., Proc. Nat'l Acad. Sci. USA, 80:31–35 (1983).
Suggs et al., Proc. Nat'l. Acad. Sci. USA, 78:6613–6617 (1981).
Bories et al., Biochem. and Biophys. Res. Comm., 147:710–715 (1987).
Arend et al., J. Immunol., 134:3868–3875 (1985).
Hannum et al., Nature, 343:336–340 (1990).
Furutani et al., Nucleic Acids Res., 13:5869–5882 (1985).
Rosenstreich et al., J. Exp. Med., 168:1767–1779 (1988).
Kramer et al., Cell, 30:599–606 (1982).
Seckinger et al., 18th Forum in Immunology, pp. 486–488 (1987).
Billingham et al., British J. Rheum., 24 (Suppl. 1):25–28 (1985).
Pujol et al., Life Sciences, 41:1187–1198 (1987).
Tan et al., Australian and New Zealand Rheum Assoc., Abstract on p. 113 (1986).
Arend et al., J. Clin. Invest., 85:1694–1697 (May 1990).
Williamson, Chem. Abstr., 107:234307K (1987).
Hall, "Isolation and Partial Purification of an Inhibitor to Interleukin I," a dissertation submitted in partial fulfillment of the requirements for the degree of Doctor of Philosophy at Virginia Commonwealth University, VCU, Richmond, VA (Dec. 1985).
Maniatis, Molecular Cloning, A Laboratory Manual, Cold Springs Harbor Laboratory, CSH, NY, pp. 229–246, 270–307, and 387–389 (1982).
Seckinger et al., J. Immunol., 139:1546–1549 (1987).
Rosenstriech, Chem. Abstr., vol. 108, No. 17 (1988), p. 559, abstract No. 148372s; from Lymphokines, 14:63–89 (1987).
Matsudaira, J. Biological Chem., 262 (21): 10035–10038 (Jul. 25, 1987).
Sofer et al., BioTechniques, Nov./Dec. 1983, pp. 198–203.
Bowie et al., Science, 247: 1306 (Mar. 16, 1990).
Barak et al., Eur. J. Immunol., 16: 1449–1452 (1986).
Dialog Abstract, BIOSIS No. 85016332, Takahashi (1987) Med. J. Hiroshima.

\* cited by examiner

35S-MET LABEL WITH MONOCYTES PLATED ON PETRI DISHES COATED WITH IgG.

35S-MET LABEL WITH MONOCYTES PLATED ON PETRI DISHES COATED WITH FCS.

SILVER STAINED GELS

AUTORADS

SILVER-STAINED GELS

AUTORAD

CONSECUTIVE SUPEROSE 12 (SIZING) CHROMATO- GRAPHIC SEPARATIONS ON MONO Q PURIFIED IL-1j

RERUN FRACTIONS 37+38

—— $OD_{280}$
—— RADIOACTIVITY
—— BIOACTIVITY

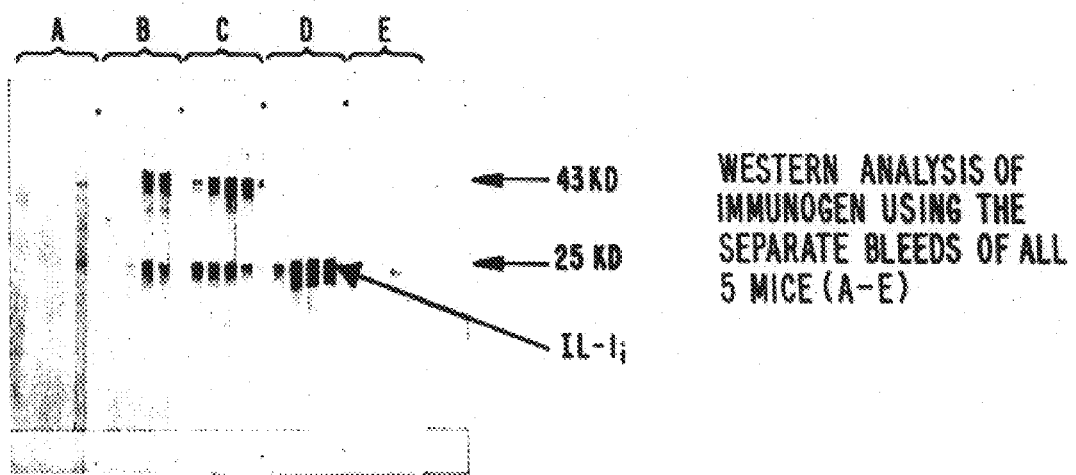

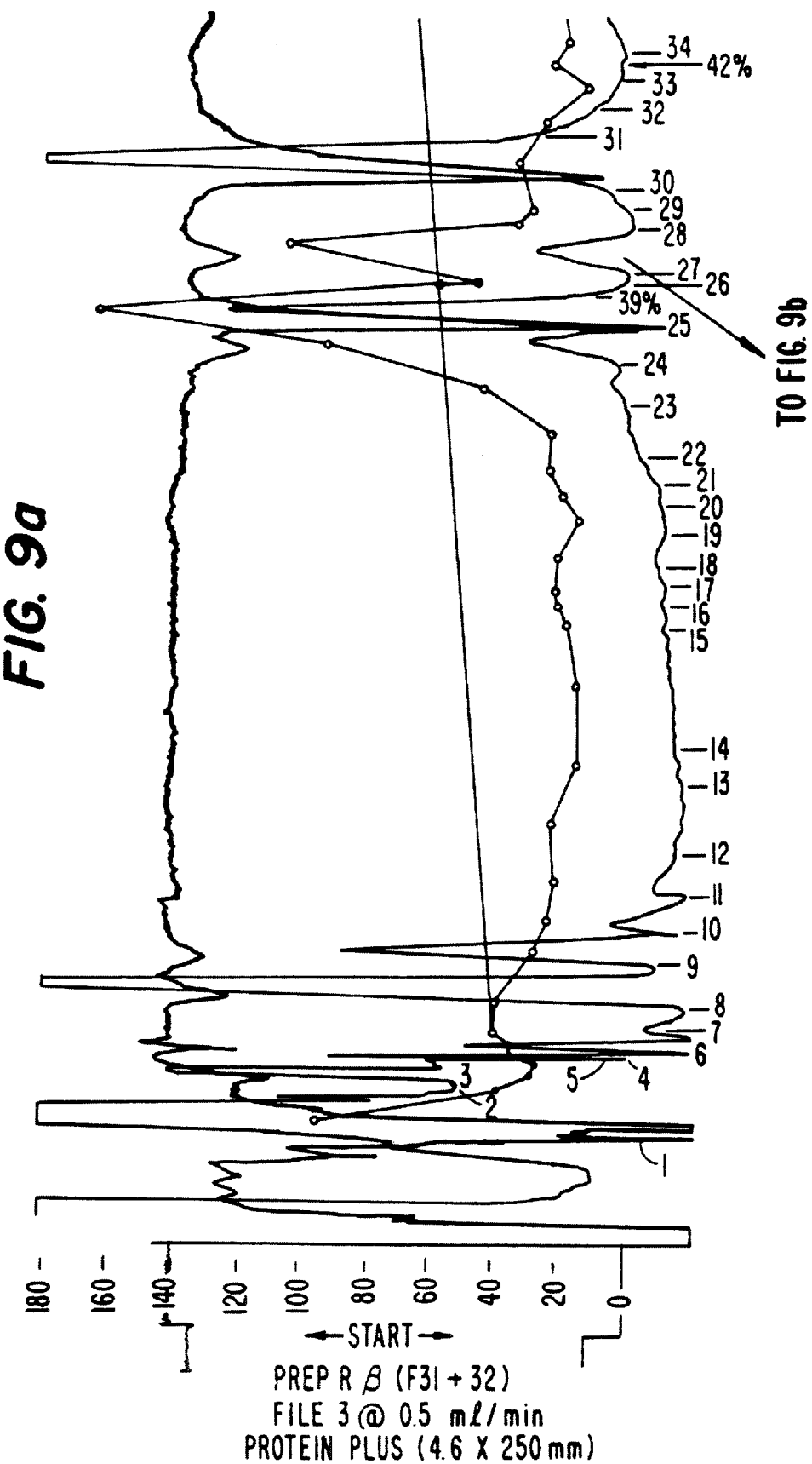

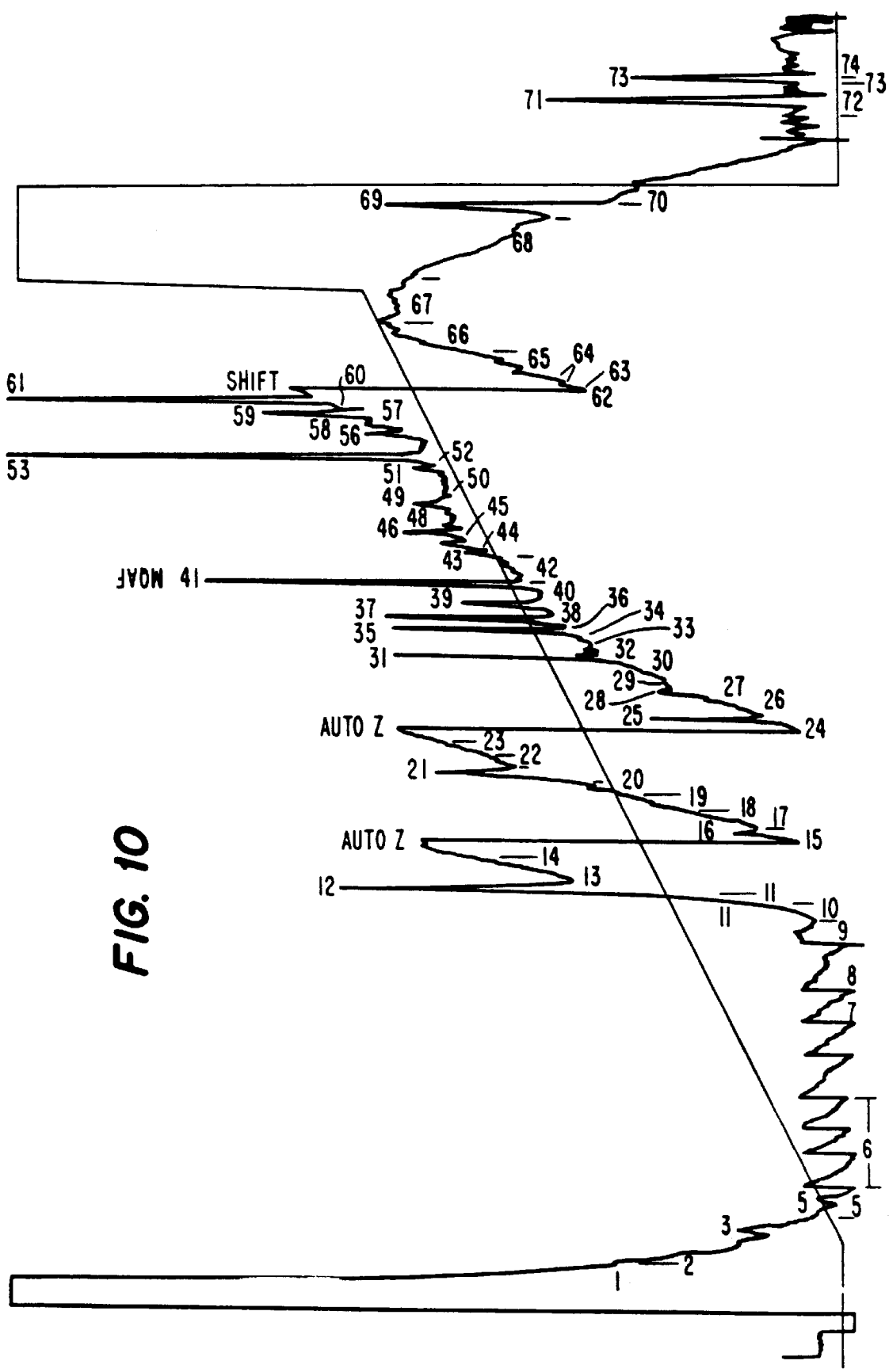

FIG. 13

```
                                27                                                      54
GCG TCA CAG AAT GGA AAT CTG CAG AGG CCT CCG CAG TCA CCT AAT CAC TCT CCT
Ala Ser Gln Asn Gly Asn Leu Gln Arg Pro Pro Gln Ser Pro Asn His Ser Pro 81                                                     108
CCT CTT CTG ATC ATT CAG AGA CCG ATC TGC CCA CCC TCT GGG AGA AAA TCC AGC
Pro Leu Leu Ile Ile Gln Arg Pro Ile Cys Pro Pro Ser Gly Arg Lys Ser Ser 135                                                     162
AAG ATG CAA GCC TTC AGA ATC TGG GAT GTT AAC CAG AAG ACC TTC TAT CTG AGG
Lys MET Gln Ala Phe Arg Ile Trp Asp Val Asn Gln Lys Thr Phe Tyr Leu Arg 189                                                     216
AAC AAC CAA CTA GTT GCT GGA TAC TTG CAA GGA CCA AAT GTC AAT TTA GAA GAA
asn Asn Gln Leu Val Ala Gly Tyr Leu Gln Gly Pro Asn Val Asn Leu Glu Glu 243                                                     270
AAG ATA GAT GTG GTA CCC ATT GAG CCT CAT GCT CTG TCT TGG GAA TCC ATG GAG
Lys Ile Asp Val Val Pro Ile Glu Pro His Ala Leu Ser Trp Glu Ser MET Glu
```

FIG. 14

```
      10        20    ↓   30        40        50        60
GAATTCCGGGCTGCAGTCACAGAATGGAAATCTGCAGAGGCCTCCGCAGTCACCTAATCA
                       M  E  I  C  R  G  L  R  S  H  L  I 70        80        90       100       110       120
CTCTCCTCCTCTTCCTGTTCCATTCAGAGACGATCTGCCCACCCTCTGGGAGAAAATCCA
 T  L  L  L  F  L  F  H  S  E  T  I  C (P) P  S  G  R  K  S 130       140       150       160       170       180
GCAAGATGCAAGCCTTCAGAATCTGGGATGTTAACCAGAAGACCTTCTATCTGAGGAACA
 S  K  M  Q  A  F  R  I  W  D  V  N  Q  K  T  F  Y  L  R  N 190       200       210       220       230       240
ACCAACTAGTTGCTGGATACTTGCAAGGACCAAATGTCAATTTAGAAGAAAAGATAGATG
 N  Q  L  V  A  G  Y  L  Q  G  P  N  V  N  L  E  E  K  I  D 250       260       270       280       290       300
TGGTACCCATTGAGCCTCATGCTCTGTTCTTGGGAATCCATGGAGGGAAGATGTGCCTGT
 V  V  P  I  E  P  H  A  L  F  L  G  I  H  G  G  K  M  C  L 310       320       330       340       350       360
CCTGTGTCAAGTCTGGTGATGAGACCAGACTCCAGCTGGAGGCAGTTAACATCACTGACC
 S  C  V  K  S  G  D  E  T  R  L  Q  L  E  A  V  N  I  T  D 370       380       390       400       410       420
TGAGCGAGAACAGAAAGCAGGACAAGCGCTTCGCCTTCATCCGCTCAGACAGTGGCCCCA
 L  S  E  N  R  K  Q  D  K  R  F  A  F  I  R  S  D  S  G  P 430       440       450       460       470       480
CCACCAGTTTTGAGTCTGCCGCCTGCCCCGGTTGGTTCCTCTGCACAGCGATGGAAGCTG
 T  T  S  F  E  S  A  A  C  P  G  W  F  L  C  T  A  M  E  A 490       500       510       520       530       540
ACCAGCCCGTCAGCCTCACCAATATGCCTGACGAAGGCGTCATGGTCACCAAATTCTACT
 D  Q  P  V  S  L  T  N  M  P  D  E  G  V  M  V  T  K  F  Y

550      ↓560       570       580       590       600
TCCAGGAGGACGAGTAGTACTGCCCAGGCCTGCTGTTCCATTCTTGCATGGCAAGGACTG
 F  Q  E  D  E  *
```

INTERLEUKIN-1 INHIBITORS, COMPOSITIONS, AND METHODS OF TREATMENT

This application is a division of application Ser. No. 08/304,437, filed Sep. 12, 1994, which is a continuation of application Ser. No. 07/987,992, filed Dec. 9, 1992 (abandoned); which is a continuation of application Ser. No. 07/685,818, filed Apr. 15, 1991 (abandoned); which is a division of application Ser. No. 07/506,522, filed Apr. 6, 1990, now U.S. Pat. No. 5,075,222, issued Dec. 24, 1991; which is a continuation of application Ser. No. 07/266,531, filed Nov. 3, 1988 (abandoned); which is a continuation-in-part application of application Ser. No. 07/248,521, filed Sep. 23, 1988 (abandoned); which is a continuation-in-part of U.S. patent application Ser. No. 07/238,713, filed Aug. 31, 1988 (abandoned), which is a continuation-in-part of U.S. patent application Ser. No. 07/199,915, filed May 27, 1988.

BACKGROUND OF THE INVENTION

A. IL-1

Interleukins-1 are a class of proteins produced by numerous cell-types, including monocytes and some macrophages. This class includes at least two 17–18 kilodalton proteins known as interleukin-1 alpha and interleukin-1 beta. These proteins have important physiological effects on a number of different target cells involved in the inflammatory and immune responses. The proteins are co-mitogens (with phytohemaglutinin) for T-cells, cause both fibroblasts and chondrocytes to secrete latent collagenase, and increase the surface adhesive powers of endothelial cells for neutrophils. In addition, they act on the hypothalamus as pyrogens, they stimulate the catabolism of muscle protein, and they cause hepatocytes to synthesize a class of proteins known as "acute phase reactants." Thus, interleukins-1 (IL-1) are obviously an important part of an organism's response to infection and injury.

B. Pathological Roles of IL-1

However, despite their normally beneficial effects, circumstances have come to light in which the actions of IL-1 are harmful. For example, IL-1 may increase the level of collagenase in an arthritic joint and has been implicated as a mediator of both the acute and chronic stages of immunopathology in rheumatoid arthritis. IL-1 may be responsible for altering endothelial cell function, directing the chemotaxis and migration of leukocytes and lymphocytes into the synovial tissue, inducing capillary proliferation, and stimulating macrophage accumulation in the synovial lining during the acute phase of this disease. In the phase of tissue destruction, IL-1 has been implicated as a mediator in induction of tissue damage through stimulating release of enzymes from fibroblasts and chondrocytes.

In addition, excessive IL-1 production has been demonstrated in the skin of patients with psoriasis and high levels of IL-1 can be found in the synovial fluid of patients with psoriatic arthritis. IL-1 released by cells in the inflamed synovium in psoriatic arthritis may mediate tissue destruction through stimulation of enzyme release from other cells. The joint pathology of Reiter's syndrome is similar to that seen in psoriatic arthritis and in rheumatoid arthritis. IL-1 has been implicated as a mediator of tissue destruction in these three different forms of inflammatory arthritis. Moreover, IL-1 may be found in the synovial fluid of patients with osteoarthritis. The release of IL-1 by chondrocytes has been implicated in the destruction of articular cartilage in this disease.

IL-1 may also increase the severity of autoimmune diseases. For example, decreased IL-1 production has been described from peripheral blood cells in persons suffering from systemic lupus erythematosus. Moreover, some of the alterations in B lymphocyte function may be related to abnormalities in IL-1 production or IL-1 availability.

Excessive IL-1 production has been demonstrated in the peripheral monocytes of patients with scleroderma, and IL-1 has been implicated as a possible agent of fibrosis through stimulation of collagen production by fibroblasts. The mechanism of tissue damage in dermatomyositis might also involve cell-mediated immunity and IL-1 may therefore be involved as a mediator in this pathophysiological process.

Acute and chronic interstitial lung disease is characterized by excessive collagen production by lung fibroblasts which may be stimulated by IL-1. Recent studies on an animal model of pulmonary hypertension indicate that IL-1 may be responsible for induction of endothelial cell changes that result in narrowing of pulmonary arteries. It is this narrowing that leads to pulmonary hypertension and further secondary damage. Thus, IL-1 inhibitors could be useful in treating these lung diseases.

Recent studies have described that IL-1 is capable of directly damaging the beta cells in the Islets of Langerhans that are responsible for the production of insulin. IL-1 damage to the cells is now hypothesized to be a primary event in the acute phase of juvenile diabetes mellitus.

Monocyte and macrophage infiltration in the kidneys predominates in many forms of acute and chronic glomerulonephritis. IL-1 release by these cells may result in local accumulation of other inflammatory cells, eventually leading to inflammatory damage and fibrotic reaction in the kidneys.

It has been demonstrated that the crystals found in tissues or fluids in gout or pseudogout can directly stimulate macrophages to release IL-1. Thus, IL-1 may be an important mediator in the inflammatory cycle in these diseases.

IL-1 is capable of inducing loss of calcium from bones and may be responsible for the osteoporosis that is seen in inflammatory joint diseases.

Keratinocytes from patients with psoriasis release large amounts of IL-1. This mediator may be responsible for the secondary cell proliferation and accumulation which occurs in the skin in patients with this disease.

IL-1 is one of the important endocenous pyrogens and may be responsible for inducing the marked decree of fever seen in some infectious diseases such as acute febrile illnesses due to bacteria or viruses.

Sarcoidosis is characterized by granulomatous lesions in many different organs in the body. IL-1 has been shown to be capable of inducing granuloma formation in vitro and may be involved in this process in patients with sarcoidosis.

Excessive IL-1 production has been demonstrated in peripheral monocytes from both Crohn's disease and ulcerative colitis. Local IL-1 release in the intestine may be an important mediator in stimulating the inflammatory cycle in these diseases.

Certain lymphomas are characterized by fever, osteoporosis and even secondary arthritis. Excessive IL-1 release has been demonstrated by some lymphoma cells in vitro and may be responsible for some of the clinical manifestations of these malignancies. Also, IL-1 production by some malignant lymphocytes may be responsible for some of the fever, acute phase response and cachexia seen with leukemias.

IL-1 release by astrocytes in the brain is thought to be responsible for inducing the fibrosis that may result after damage to the brain from vascular occlusion.

C. Uses for an IL-1 Inhibitor

In these and other circumstances in which IL-1 has a harmful effect, there is clearly a clinical use for an inhibitor of IL-1 action. As IL-1 is a co-mitogen for T-cells, it is central to the development of autoimmune and other immune diseases. Thus, systemically administered, IL-1 inhibitors could be useful immunosuppressive agents. Locally applied, such IL-1 inhibitors could serve to prevent tissue destruction in an inflamed joint and other sites of inflammation. Indeed, to prevent tissue destruction some IL-1 inhibitors could be even more effective when administered in conjunction with collagenase inhibitors.

Therapeutic intervention against the action of IL-1 might be possible at the level of synthesis, secretion, or the target cell's binding or response to the protein. IL-1 is synthesized by monocyte/macrophages and other cells in response to lipopolysaccharides, complement fragments and viruses. Any molecule that blocks binding of these inducing agents to producer cells or which interferes with their effects on the physiology of these cells would serve as a regulator of IL-1 action. IL-1 is not secreted by a traditional secretion system since mRNAs have been isolated that code for at least two 30 kd precursors of the proteins but which do not contain a hydrophobic signal sequence. Release of the active protein from the inactive precursor probably requires proteolysis of that precursor. An inhibitor of the release of IL-1 or IL-1s from their precursors could theoretically regulate IL-1 action. IL-1 probably acts on target cells through a classical receptor-mediated pathway, although that receptor has not yet been isolated. Thus, it could be that a molecule that interferes with IL-1 binding to its receptors, or down-regulates these receptors, could also regulate IL-1 action. Moreover, although the intracellular events following receptor binding of IL-1 are not yet fully understood, it is possible that agents exist that can interfere with the cellular responses to other receptor-mediated events and therefore block IL-1 action. For the reasons stated above, proteins and small molecules capable of inhibiting IL-1 in one or more of these manners have been sought.

Surprisingly, the present inventors have found at least two IL-1 inhibitor proteins with IL-1 inhibiting properties. These molecules have been obtained in a purified form which will enable one of ordinary skill in the art to determine their amino acid sequence. Furthermore, a preparation of cells has been characterized which produce these proteins, and an mRNA that leads to its synthesis has been characterized. Finally, an antisera has been developed that will facilitate screening of cDNA expression libraries for the genes coding for these inhibitors. Together these reagents will allow cDNAs encoding the IL-1 inhibitors to be cloned. These genes will, in turn, make possible the large scale production of IL-1 inhibitors suitable for use in pharmaceutical formulations useful in treating pathophysicological conditions mediated by IL-1.

SUMMARY OF THE INVENTION

This invention relates to IL-1 inhibitors ("IL-1i") generally and, more specifically, to a monocyte-derived IL-1 inhibitor. Additionally, the present invention relates to biologically-active analogs of these inhibitors.

An object of the present invention is to provide purified forms of IL-1 inhibitors which are active against IL-1α or IL-1β or a combination thereof. An additional object of the present invention is to provide these inhibitors in purified forms to enable the determination of their amino acid sequence. A further object is to provide the amino acid sequences of certain IL-1 inhibitors. Furthermore, the identification of biologically-active analogs of such IL-1 inhibitors with enhanced or equivalent properties is also one of the objects of the invention.

Additionally, it is an object of this invention to provide a recombinant-DNA system for the production of the IL-1 inhibitors described herein. A further object of the present invention includes providing purified forms of IL-1 inhibitors which would be valuable as pharmaceutical preparations exhibiting activity against IL-1.

Additional objects and advantages of the invention will be set forth in part in the description which follows, and in part will be obvious from the description or may be learned from the practice of the invention. The objects and advantages may be realized and attained by means of the instrumentalities and combinations particularly pointed out in the appended claims.

To achieve the objects and in accordance with the purposes of the present invention, IL-1 inhibitors are disclosed which exhibit inhibitory activity against IL-1. The preferred inhibitors have been isolated in a purified form from monocyte-conditioned medium with monocytes grown on IgG-coated plates.

Preferred inhibitors of the preset invention are 1, 2 and 3. Inhibitors 1 and 2 are proteins running at positions characteristic of 22–23 kDa proteins on SDS-PAGE and eluting at 52 mM and 60 mM NaCl, respectively, from a Mono Q FPLC column under specified conditions. Inhibitor 3 is a protein running at a position characteristic of a 20 kD protein on SDS-PAGE and eluting at 48 mM NaCl from a Mono Q FPLC column under the specified conditions. Additionally, to achieve the objects and in accordance with the purposes of the present invention, pharmaceutical compositions containing, at least one of the active ingredients, an IL-1 inhibitor in accordance with the present invention or its biologically-active analog as set forth herein are disclosed.

Moreover, to achieve the objects and in accordance with the purposes of the present invention, a recombinant-DNA system for the creation of these IL-1 inhibitors and their analogs is also disclosed. A preferred embodiment of this system includes at least one cDNA clone or its synthetic equivalent encoding at least one IL-1 inhibitor along with vectors and cells constituting an expression system capable of expressing the IL-1 inhibitors disclosed herein. Antisera for use in identifying these cDNA clones is also provided. Expression systems for producing these IL-1 inhibitors using these cDNA clones, their analogs, or other DNA sequences encoding these inhibitors are also provided.

BRIEF DESCRIPTION OF THE FIGURES

FIG. 2b is an autoradiogram of the gels shown in FIG. 2a.

FIG. 3a presents chromatography data with the radioactivity pattern superimposed. FIG. 3b presents silver stained gels run on samples of the fractions indicated in FIG. 3a.

FIGS. 8a and 8b present chromatography data. FIG. 8c presents a silver stained gel run on samples of fractions indicated in FIG. 8b. FIG. 8d presents an autoradiogram.

FIGS. 9a and 9b present data on IL-1i-β. FIG. 9a presents chromatography data. FIG. 9b presents SDS-PAGE data.

FIG. 10 presents data of IL-1i-α peptide separation.

FIG. 12b presents data of an autoradiogram of a Southern blot of the gel shown in FIG. 12a.

FIG. 13 depicts a part of the DNA sequence of the protein coding region of lambda GT10-IL1i-2A and the predicted amino acid sequence according to Example 6.

FIG. 14 depicts the nucleotide sequence of GT10-i11I-2A.

FIG. 15 depicts a peptide including, inter alia, an IL-1i sequence and a secretory leader sequence.

DESCRIPTION OF THE PREFERRED EMBODIMENT

Figure 1A:
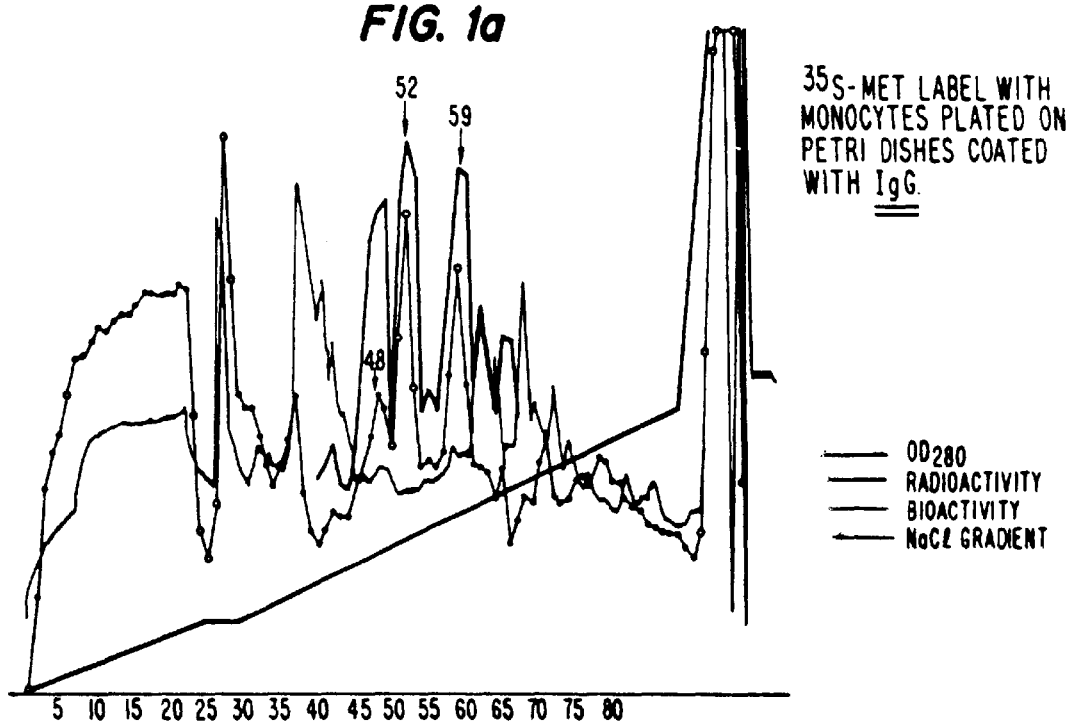
FIGS. 1a and 1b depict the protein profile of the Mono Q chromatography of two metabolically-labelled monocyte supernatants. The cells were cultured on IgG (1a) or fetal calf serum (1b) coated plates.

Reference will now be made in detail to the presently preferred embodiments of The invention, which, together with the following examples, serve to explain the principles of the invention.

A. Inhibitor from Human Monocytes

As noted above, the present invention relates to IL-1 inhibitors which have been isolated in a purified form. Preferably, the IL-1 inhibitors of the present invention are derived from human monocyte conditioned medium where the monocytes are grown on IgG coated vessels. In addition, the invention encompasses substantially purified IL-1 inhibitors of any origin which are biologically equivalent to the inhibitor derived from human monocyte-contained medium.

By "biologically equivalent," as used throughout the specification and claims, we mean compositions of the present invention that are capable of preventing IL-1 action in a similar fashion, but not necessarily to the same degree, as the native IL-1 inhibitor isolated from monocytes. By "substantially homologous" as used throughout the ensuing specification and claims, is meant a degree of homology to the native IL-1 inhibitor isolated from monocyte-conditioned medium in excess of that displayed by any previously reported IL-1 inhibitors. Preferably, the degree of homology in excess of 70 percent, more preferably in excess of 80 percent and even more preferably in excess of 90 percent. A particularly preferred group of inhibitors are in excess of 95 percent homologous with the native inhibitor. The percentage of homology as described is calculated as the percentage of amino acid residues found in the smaller of the two sequences that align with identical amino acid residues in the sequence being compared when four gaps in a length of 100 amino acids may be introduced to assist in that alignment as set forth by Dayhoff, M. D. in *Atlas of Protein Sequence and Structure* Vol.5, p. 124 (1972), National Biochemical Research Foundation, Washington, D.C., specifically incorporated herein by reference.

The preferred IL-1 inhibitors of the present invention have been derived from monocyte-conditioned medium and, for the first time, have been isolated in a purified form. For the purposes of the present application, "pure form" or "purified form" when used to refer to the IL-1 inhibitors disclosed herein, shall mean a preparation which is substantially free of other proteins which are not IL-1 inhibitor proteins. Preferably, the IL-1 inhibitors of the present invention are at Least 90% pure and preferably 95% pure.

At least three purified IL-1 inhibitors have been isolated by the methods of the Example. These include inhibitor 1, inhibitor 2 and inhibitor 3. Inhibitor 1 is behaving as a 22–23 kDa molecule on SDS-PAGE with an approximate isoelectric point of 4.8 and eluting from a Mono Q FPLC column at around 52 mM NaCl in Tris buffer, pH 7.6. Inhibitor 2 is also a 22–23 kDa protein, pI=4.8, but eluting from a Mono Q column at 60 mM NaCl. Inhibitor 3 is a 20 kDa protein and elutes from a Mono Q column at 48 mM NaCl. Inhibitors 1, 2 and 3 are related immunologically and functionally. Having obtained these inhibitors in purified forms has enabled the present inventors to obtain their amino acid sequences. Using the purified inhibitors disclosed for the first time wherein and methods such as those described in and by ABI Protein Sequencer technical manuals supplied with the ABI Protein Sequencer, a substantial proportion of the amino acid sequences of these inhibitors can be deduced.

Example 3 shows amino acid sequence data obtained:of three species of IL-1 inhibitors, namely IL-$1_i$-X, IL-$1_i$-α and IL-$1_i$-β.

The present inventors have discovered at least one antibody raised against an IL-1 inhibitor. Other polyclonal and monoclonal antibodies against this and other IL-1 inhibitors may be prepared by methods known to those of ordinary skill in the art. One particular polyclonal antibody is described in Example 4.

B. Recombinant Inhibitor

1. General

A recombinant DNA method for the manufacture of an IL-1 inhibitor is now disclosed. In one embodiment of the invention, the active site functions in a manner biologically equivalent to that of the native IL-1 inhibitor isolated from human. A natural or synthetic DNA sequence may be used to direct production of the IL-1 inhibitors. This method comprises:

(a) Preparation of a DNA sequence capable of directing a host cell to produce a protein having IL-1 inhibitor activity;

(b) Cloning the DNA sequence into a vector capable of being transferred into and replicated in a host cell, such vector containing operational elements needed to express the DNA sequence;

(c) Transferring the vector containing the synthetic DNA sequence and operational elements into a host cell capable of expressing the DNA encoding IL-1 inhibitor;

(d) Culturing the host cells under conditions appropriate for amplification of the vector and expression of the inhibitor;

(e) Harvesting the inhibitor; and (f) Permitting the inhibitor to assume an active tertiary structure whereby it possesses IL-1 inhibitory activity.

2. DNA Sequences

DNA sequences contemplated for use in this method are discussed in part in Example 5 and in part in Example 6. It is contemplated that these sequences include synthetic and natural DNA sequences. The natural sequences further include cDNA or genomic DNA segments.

Example 6 provides a molecular clone of DNA encoding a protein identical to that isolated in Examples 1–3. In Example 6, a plaque, GT10-IL1i-2A, was isolated from a GT10 Library. The phage within this plaque was propagated and the DNA was isolated and digested with EcoRI. An EcoRI fragment of 1850 base pairs carries the coding sequence for IL1 inhibitor. FIG. 13 shows the partial DNA sequence of the EcoRI fragment.

In light of the teachings contained herein and procedures known, other synthetic polynucleotide sequences will be available to one of ordinary skill in the art. As an example of the current state of the art relating to polynucleotide synthesis, one is directed to Matteucci, M. D. and Caruthers, M. H., in J. Am. Chem. Soc. 103:3185 (1981) and Beaucage, S. L. and Caruthers, M. H. in Tetrahedron Lett. 22:1859 (1981), and to the instructions supplied with an ABI oligonucleotide synthesizer, each of which is specifically incorporated herein by reference.

These synthetic sequences may be identical to the natural sequences described in more detail below or they may contain different nucleotides. In one embodiment, if the synthetic sequences contain nucleotides different from those found in the natural DNA sequences of this invention, it is contemplated that these different sequences will still encode a polypeptide which has the same primary structure as IL-1i isolated from monocytes. In an alternate embodiment, the synthetic sequence containing different nucleotides will encode a polypeptide which has the same biological activity as the IL-1i described herein.

Additionally, the DNA sequence may be a fragment of a natural sequence, i.e., a fragment of a polynucleotide which occurred in nature and which has been isolated and purified for the first time by the present inventors. In one embodiment, the DNA sequence is a restriction fragment isolated from a cDNA library.

In an alternative embodiment, the DNA sequence is isolated from a human genomic library. An example of such a library useful in this embodiment is set forth by Lawn et al. in Cell 15:1157–1174 (1978), specifically incorporated herein by reference.

In a preferred version of this embodiment, it is contemplated that the natural DNA sequence will be obtained by a method comprising:

(a) Preparation of a human cDNA library from cells, preferably monocytes, capable of generating an IL-1 inhibitor in a vector and cell capable of amplifying and expressing all or part of that cDNA;

(b) Probing the human DNA library with at least one probe capable of binding to the IL-1 inhibitor gene or its protein product;

(c) Identifying at least one clone containing the gene coding for the inhibitor by virtue of the ability of the clone to bind at least one probe for the gene or its protein product;

(d) Isolation of the gene or portion of the gene coding for the inhibitor from the clone or clones chosen;

(e) Linking the gene, or suitable fragments thereof, to operational elements necessary to maintain and express the gene in a host cell.

The natural DNA sequences useful in the foregoing process may also be identified and isolated through a method comprising:

(a) Preparation of a human genomic DNA library, preferably propagated in a recArecBC E. coli host;

(b) Probing the human genomic DNA library with at least one probe capable of binding to an IL-1 inhibitor gene or its protein product;

(c) Identification of at least one clone containing the gene coding for the inhibitor by virtue of the ability of the clone to bind at least one probe for the gene or its protein product;

(d) Isolation of the gene coding for the inhibitor from the clone(s) identified; and (e) Linking the gene, or suitable fragments thereof, to operational elements necessary to maintain and express the gene in a host cell.

In isolating a natural DNA sequence suitable for use in the above-method, it is preferred to identify the two restriction sites located within and closest to the end portions of the appropriate gene or sections of the gene. The DNA segment containing the appropriate gene is then removed from the remainder of the genomic material using appropriate restriction endonucleases. After excision, the 3' and 5' ends of the DNA sequence and any exon junctions are reconstructed to provide appropriate DNA sequences capable of coding for the N- and C-termini of the IL-1 inhibitor protein and capable of fusing the DNA sequence to its operational elements.

3. Vectors (a) Microorganisms, Especially E. coli

The vectors contemplated for use in the present invention include any vectors into which a DNA sequence as discussed above can be inserted, along with any preferred or required operational elements, and which vector can then be subsequently transferred into a host cell and replicated in such cell. Preferred vectors are those whose restriction sites have been well documented and which contain the operational elements preferred or required for transcription of the DNA sequence. However, certain embodiments of the present invention are also envisioned which employ currently undiscovered vectors which would contain one or more of the cDNA sequences described herein. In particular, it is preferred that all of these vectors have some or all of the following characteristics: (1) possess a minimal number of host-organism sequences; (2) be stably maintained and propagated in the desired host; (3) be capable of being present in a high copy number in the desired host; (4) possess a regulatable promoter positioned so as to promote transcription of the gene of interest; (5) have at least one marker DNA sequence coding for a selectable trait present on a portion of the plasmid separate from that where the DNA sequence will be inserted; and (6) a DNA sequence capable of terminating transcription.

In various preferred embodiments, these cloning vectors containing and capable of expressing the DNA sequences of the present invention contain various operational elements. These "operational elements," as discussed herein, include at least one promoter, at least one Shine-Dalgarno sequence and initiator codon, and at least one terminator codon. Preferably, these "operational elements" also include at least one operator, at least one leader sequence for proteins to be exported from intracellular space, at least one gene for a regulator protein, and any other DNA sequences necessary or preferred for appropriate transcription and subsequence translation of the vector DNA.

Certain of these operational elements may be present in each of the preferred vectors of the present invention. It is contemplated that any additional operational elements which may be required may be added to these vectors using methods known to those of ordinary skill in the art, particularly in light of the teachings herein.

In practice, it is possible to construct each of these vectors in a way that allows them to be easily isolated, assembled and interchanged. This facilitates assembly of numerous functional genes from combinations of these elements and :the coding region of the DNA sequences. Further, many of these elements will be applicable in more than one host. It is additionally contemplated that the vectors, in certain preferred embodiments, will contain DNA sequences capable of functioning as regulators ("operators"), and other DNA sequenes capable of coding for regulator proteins.

(i) Regulators

These regulators, in one embodiment, will serve to prevent expression of the DNA sequence in the presence of certain environmental conditions and, in the presence of other environmental conditions, will allow transcription and subsequent expression of the protein coded for by the DNA sequence. In particular, it is preferred that regulatory segments be inserted into the vector regulators ("operators"), and other DNA sequenes capable of occur to a greatly reduced extent, in the absence of, for example, isopropylthio-beta-D-galactoside. In this situation, the transformed microorganisms containing the DNA sequence may be grown to at a desired density prior to initiation of the expression of IL-1i. In this embodiment, expression of the desired protein is induced by addition of a substance to the microbial environment capable of causing expression of the DNA sequence after the desired density has been achieved.

(ii) Promoters

The expression vectors must contain promoters which can be used by the host organism for expression of its own proteins. While the lactose promoter system is commonly used, other microbial promoters have been isolated and characterized, enabling one skilled in the art to use them for expression of the recombinant IL-1i.

(iii) Transcription Terminator

The transcription terminators contemplated herein serve to stabilize the vector. In particular, those sequences as described by Rosenberg, M. and Court, D., in Ann. Rev. Genet. 13:319–353 (1979), specifically incorporated herein by reference, are contemplated for use in the present invention.

(iv) Non-Translated Sequence

It is noted that, in the preferred embodiment, it may also be desirable to reconstruct the 3' or 5' end of the coding region to allow incorporation of 3' or 5' non-translated sequences into the gene transcript. Included among these non-translated sequences are those which stabilize the mRNA as they are identified by Schmeissner, U., McKenney, K., Rosenberg, M and Court, D. in J. Mol. Biol. 176:39–53 (1984), specifically incorporated herein by reference.

(v) Ribosome Binding Sites

The microbial expression of foreign proteins requires certain operational elements which include, but are not limited to, ribosome binding sites. A ribosome binding site is a sequence which a ribosome recognizes and binds go in the initiation of protein synthesis as set forth in Gold, L., et al., Ann. Rev. Microbio. 35:557–580; or Marquis, D. M., et al., Gene 42:175–183 (1986), both of which are specifically incorporated herein by reference. A preferred ribosome binding site is GAGGCGCAAAAA(ATG).

(vi) Leader Sequence and Translational Coupler

Additionally, it is preferred that DNA coding for an appropriate secretory leader (signal) sequence be present at the 5' end of the DNA sequence as set forth by Watson, M. E. in Nucleic Acids Res. 12:5145–5163, specifically Incorporated herein by reference, if the protein is to be excreted from the cytoplasm. The DNA for the leader sequence must be in a position which allows the production of a fusion protein in which the leader sequence is immediately adjacent to and covalently joined to the inhibitor, i.e., there must be no transcription or translation termination signals between the two DNA coding sequences. The presence of the leader sequence is desired in part for one or more of the following reasons. First, the presence of the leader sequence may facilitate host processing of the IL-1i. In particular, the leader sequence may direct cleavage of the initial translation product by a leader peptidase to remove the leader sequence and leave a polypeptide with the amino acid sequence which has potential protein activity. Second, the presence of the leader sequence may facilitate purification of the IL-1i, through directing the protein out of the cell cytoplasm. In some species of host microorganisms, the presence of an appropriate leader sequence will allow transport of the completed protein into the periplasmic space, as in the case of some E. coli. In the case of certain E. coli, Saccharomyces and strains of Bacillus and Pseudomonas, the appropriate leader sequence will allow transport of the protein through the cell membrane and into the extracellular medium. In this situation, the protein may be purified from extracellular protein. Thirdly, in the case of some of the proteins prepared by the present invention, the presence of the leader sequence may be necessary to locate the completed protein in an environment where it may fold to assume its active structure, which structure possesses the appropriate protein activity.

In one preferred embodiment of the present invention, an additional DNA sequence is located immediately preceding the DNA sequence which codes for the IL-1 inhibitor. The additional DNA sequence is capable of functioning as a translational coupler, i.e., it is a DNA sequence that encodes an RNA which serves to position ribosomes immediately adjacent to the ribosome binding site of the inhibitor RNA with which it is contiguous. In one embodiment of the present invention, the translational coupler may be derived using the DNA sequence TAACGAGGCGCAAAAAAT-GAAAAAGACAGCTATCGCGATCTTGGAG-GATGATTAAATG and methods currently known to those of ordinary skill in the art related to translational couplers.

(vii) Translation Terminator

The translation terminators contemplated herein serve to stop the translation of mRNA. They may be either natural, as described by Kohli, J., Mol. Gen. Genet. 182:430–439; or synthesized, as described by Pettersson, R. F. Gene 24:15–27 (.1983), both of which references are specifically incorporated herein by reference.

(viii) Selectable Marker

Additionally, it is preferred that the cloning vector contain a selectable marker, such as a drug resistance marker or other marker which causes expression of a selectable trait by the host microorganism. In one embodiment of the present invention, the gene for ampicillin resistance is included in the vector while, in other plasmids, the gene for tetracycline resistance or the gene for chloramphenicol resistance is included.

Such a drug resistance or other selectable marker is intended in part to facilitate in the selection of transformants. Additionally, the presence of such a selectable marker in the cloning vector may be of use in keeping contaminating microorganisms from multiplying in the culture medium. In this embodiment, a pure culture of the transformed host microorganisms would be obtained by culturing the microorganisms under conditions which require the induced phenotype for survival.

The operational elements as discussed herein are routinely selected by those of ordinary skill in the art in light of prior literature and the teachings contained herein. General examples of these operational elements are set forth in B.

Lewin, *Genes,* Wiley & Sons, New York (1983), which is specifically incorporated herein by reference. Various examples of suitable operational elements may be found on the vectors discussed above and may be elucidated through review of the publications discussing the basic characteristics of the aforementioned vectors.

Upon synthesis and isolation of all necessary and desired component parts of the above-discussed vector, the vector is assembled by methods generally known to those of ordinary skill in the art. Assembly of such vectors is believed to be within the duties and tasks performed by those with ordinary skill in the art and, as such, is capable of being performed without undue experimentation. For example, similar DNA sequences have been ligated into appropriate cloning vectors, as set forth by Maniatis et al. in Molecular Cloning, Cold Spring Harbor Laboratories (1984), which is specifically incorporated herein by reference.

In construction of the cloning vectors of the present invention, it should additionally be noted that multiple copies of the DNA sequence and its attendant operational elements may be inserted into each vector. In such an embodiment, the host organism would produce greater amounts per vector of the desired IL-1 inhibitor. The number of multiple copies of the DNA sequence which may be inserted into the vector is limited only by the ability of the resultant vector, due to its size, to be transferred into and replicated and transcribed in an appropriate host cell.

(b) Other Microorganisms

Vectors suitable for use in microorganisms other than *E. coli* are also contemplated for this invention. Such vectors are described in Table 1. In addition, certain preferred vectors are discussed below.

3. Shinatake, H. and Rosenberg, M. Nature 292, 128–132 (1981).
4. Derom, C., Gheysen. G. and Fiers, W. Gene 17, 45–51 (1982).
5. Hallewell, R. A. and Emtage, S. Gene 2, 27–47 (1984).
6. Brosius. J., Bull, T. J., Sleeter, D. D. and Noller, H. F. J. Mol. Biol. 148, 107–127 (1981).
7. Normanly, J., Ogden, R. C., Horvath, S. J. and Abelson, J. Nature 321. 213–219 (1986).
8. Belasco, J. G., Nilsson, G., von Gabain, A. and Cohen, S. N. Cell 46, 245–251 (1986).
9. Schmeissner, U., McKenney, K., Rosenberg M. and Court, D. J. Mol. Biol. 176, 39–53 (1984).
10. Mott, J. E., Galloway, J. L. and Platt, T. EMBO J. 4, 1887–1891 (1985).
11. Koshland, D. and Botstein, D. Cell 2, 749–760 (1980).
12. Movva, H. R., Nakamura, K. and Inouye, M. J. Mol. Biol. 143, 317–328 (1950).
13. Surin, B. P., Jans, D. A., Fimmel, A. L., Shaw, D. C., Cox, G. B. and Rosenberg, H. J. Bacteriol. 157, 772–778 (1984).
14. Sutcliffe, J. G. Proc. Natl. Acid. Sci. USA 75, 3737–3741 (1998).
15. Peden, K. W. C. Gene 22, 277–280 (1983).
16. Alton, N. K. and Vapnek. D. Nature 282, 864–869 (1979).
17. Yang, M., Galizzi, A., and Henner, D. Nuc. Acids Res. 11(2), 237–248 (1983).
18. Wong, S.-L., Price, C. W., Goldfarb, D. S., and Doi, R. H. Proc. Natl. Acid. Sci. USA 81, 1164–1188 (1984).
19. Wang, P.-Z., and Doi. R. H. J. Biol. Chem. 259, 8619–8625, (1984).

TABLE 1

| HOSTS | REGULATED PROMOTERS | INDUCER | TRANSCRIPTION TERMINATOR | MRNA STABILIZATION | TRANSCRIPTIONAL START SITE & LEADER PEPTIDE | MARKER | RS BINDING SITE |
|---|---|---|---|---|---|---|---|
| E. coli | Lac[1], Tac[2] Lambda pL Trp[5] | IPTG increased temperature IAA addition or tryptophan depletion | rrnB[6] rrnC[7] | ompA[8] lambda int[9] trp[10] | bla[11] ompA[12] phoS | ampicillin[14] tetracycline[14,15] chloramphenical[16] | |
| Bacillus | *alpha amylase[17] *subtilisin[18] *p-43[19] spac-I[26] | IPTG | E. coli rrn rrn BT.T[20] | | B.amy neutral protease[21] B.amy alpha-amylase[22] B.subt. subtilisin[23] | Kan[r 24] Cam[r 25] | B.amy neural protease B.amy alpha-amylase[22] |
| Pseudomonas | Trp[27] (E. coli) Lac(E. coli) Tac(E. coli) | IAA addition, or tryptophan depletion IPTG | | | phospholipase[28] exotoxin A[29] | sulfonamide[30] streptomycin[30] | Trp (E. coli) |
| Yeast | Gal I[31], 10[32] Adh I[33], II[34] Pho 5 | Glucose depletion and galactose Glucose depletion Phosphate depletion | Cyc 1 Una Alpha factor Sac 2 | | Invertase[36] Acid phosphatase[36] Alpha Factor | Ura 3[37] Leu 2[38] His 3 Tap 1 | |

*non-regulated

1. Backmen, K., Ptashne, M. and Gilbert, W. Proc. Natl. Acad. Sci. USA 73, 4174–4178 (:976).
2. de Boer, H. A., Comstock, L. J., and Vasser, M. Proc. Natl. Acad. Sci. USA 80, 21–25 (1983).
20. Lin, C.-K., Quinn, L. A. Rodriquez, R. L. J. Cell Biochem. Suppl. (9B), p.196 (1985).
21. Vesantha, M., Thompson, L. D., Rhodes, C., Benner, C., Nagle, J., and Filpula, D. J. Bact. 159(3), 811–819 (1984).

22. Palva, I., Servas, M., Lehtovaara, P., Sibazkov, M., and Keariainen, L. Proc. Natl. Aced. Sci. USA 79, 5582–5586 (1982).
23. Wong. S.-L., Price., C. W., Goldfarb, D. S., and Doi, R. H. Proc. Natl. Aced. Sci. USA 81, 1184–1188 (1984).
24. Sullivan, M. A., Yasbin, R. C., and Young, F. E. Gene 29, 21–46 (1984).
25. Vasanthe, N., Thompson, L. D., Rhodes, C., Banner, C. Nagle., J., and Filpula, D. J. Bact. 159(3) 811–819 (1984).
26. Yansura, D. G. and Henner, D. J. PNAS 81, 439–443 (1984).
27. Gray, G. L., McKeown, K. A., Jones, A. J. S., Seeburg, P. H. and Heyneker, H. L. Biotechnology, 161–165 (1984).
28. Lory, S., and Tal, P. C. Gene 22, 95–101 (1983).
29. Liu, P. V. J. Infect. Dis. 130 (suppl), 594–599 (1974).
30. Wood, D. D., Hollinger, N. F., and Tindol, M. H. J. Bact. 145, 1448–1451 (1981).
31. St. John, T. P. and Davis, R. W. J. Mol. Biol. 152, 285–315 (1981).
32. Hopper, J. E., and Rove, L. B. J. Biol. Chem. 253, 7566–7569 (1978).
33. Denis, C. L., Ferguson, J. and Young, E. T. J. Biol. Chem. 258, 1165–1171 (1983).
34. Lutsdorf. L. and Megnet, R. Archs. Biochem. Biophys. 126, 933–944 (1968).
35. Meyhack, B., Bajwe, N., Rudolph, H. and Minnen, A. EMBO. J. 6, 675–680 (1982).
36. Watson, N. E. C. Nucleic Acid Research 12, 5145–5164 (1984).
37. Gerband, C. and Guerineau, W. Curr. Genet. 1, 219–228 (1980).
38. Minnen, A., Hicks, J. D. and Fink, G. R. Proc. Natl. Acad. Sci. USA 75, 1929–1933 (1978).
39. Jabber, N. A., Sivasubramanian, N. and Nayak, D. P. Proc. Natl. Aced. Sci. USA 82, 2019–2023 (1985).

(i) Pseudomonas Vectors

Several vector plasmids which autonomously replicate in a broad range of Gram negative bacteria are preferred for use as cloning vehicles in hosts of the genus Pseudomonas. Certain of these are described by Tait, R. C., Close, T. J., Lundquist, R. C., Hagiya, M., Rodriguez, R. L., and Kado, C. I. In Biotechnology, May, 1983, pp. 269–275; Panopoulos, N. J. in *Genetic Engineering in the Plant Sciences,* Praeger Publishers, New York, N.Y., pp. 163–185 (1981); and Sakagucki, K. in Current Topic in Microbiology and Immunology 96:31–45 (1982), each of which is specifically incorporated herein by reference.

One particularly preferred construction would employ the plasmid RSF1010 and derivatives thereof as described by Bagdasarian, M., Bagdasarian, M. M., Coleman, S., and Timmis, K. N. in *Plasmids of Medical, Environmental and Commercial Importance,* Timmis, K. N. and Puhler, A. eds., Elsevier/North Holland Biomedical Press (1979), specifically incorporated herein by reference. The advantages of RSF1010 are that it is relatively a small, high copy number plasmid which is readily transformed into and stably maintained in both *E. coli* and Pseudomonas species. In this system, it would be preferred to use the Tac expression system as described for Escherichia, since it appears that the *E. coli* trp promoter is readily recognized by Pseudomonas RNA polymerase as set forth by Sakagucki, K. in Current Topics in Microbiology and Immunology 96:31–45 (1982) and Gray, G. L., McKeown, K. A., Jones, A. J. S., Seeburg, P. H., and Heyneker, H. L. in Biotechnology, Feb. 1984, pp. 161–165, both of which are specifically incorporated herein by reference. Transcriptional activity may be further maximized by requiring the exchange of the promoter with, e.g., an *E. coli* or *P. aeruginosa* trp promoter. Additionally, the lacI gene of *E. coli* would also be included in the plasmid to effect regulation.

Translation may be coupled to translation initiation for any of the Pseudomonas proteins, as well as to initiation sites for any of the highly expressed proteins of the type chosen to cause intracellular expression of the inhibitor.

In those cases where restriction minus strains of a host Pseudomonas species are not available, transformation efficiency with plasmid constructs isolated from *E. coli* are poor. Therefore, passage of the Pseudomonas cloning vector through an r– m+ strain of another species prior to transformation of the desired host, as set forth in Bagdasarian, M., et al., Plasmids of *Medical, Environmental and Commercial Importance,* pp. 411–422, Timmis and Puhler eds., Elsevier/North Holland Biomedical Press (1979), specifically incorporated herein by reference, is desired.

(ii) Bacillus Vectors

Furthermore, a preferred expression system in hosts of the genus Bacillus involves using plasmid pUB110 as the cloning vehicle. As in other host vectors system, it is possible in Bacillus to express the IL-1i of the present invention as either an intracellular or a secreted protein. The present embodiments include both systems. Shuttle vectors that replicate in both Bacillus and *E. coli* are available for constructing and testing various genes as described by Dubnau, D., Gryczan, T., Contente, S., and Shivakumar, A. G. in *Genetic Engineering,* Vol. 2, Setlow and Hollander eds., Plenum Press, New York, N.Y., pp. 115–131 (1980), specifically incorporated herein by reference. For the expression and secretion of the IL-1i from *B. subtilis,* the signal sequence of alpha-amylase is preferably coupled to the coding region for the protein. For synthesis of intracellular inhibitor, the portable DNA sequence will be translationally coupled to the ribosome binding site of the alpha-amylase leader sequence.

Transcription of either of these constructs is preferably directed by the alpha-amylase promoter or a derivative thereof. This derivative contains the RNA polymerase recognition sequence of the native alpha-amylase promoter but incorporates the lac operator region as well. Similar hybrid promoters constructed from the penicillinase gene promoter and the lac operator have been shown to function in Bacillus hosts in a regulatable fashion as set forth by Yansura, D. G. and Henner in *Genetics and Biotechnology of Bacilli,* Ganesan, A. T. and Hoch, J. A., eds., Academic Press, pp. 249–263 (1984), specifically incorporated by reference. The lacI gene of *E. coli* would also be included in the plasmid to effect regulation.

(iii) Clostridium Vectors

One preferred construction for expression in Clostridium is in plasmid pJU12, described by Squires, C. H. et al., in J. Bacteriol. 159:465–471 (1984) and specifically incorporated herein by reference, transformed into *C. perfringens* by the method of Heefner, D. L. et al., as described in J. Bacteriol. 159:460–464 (1984), specifically incorporated herein by reference. Transcription is directed by the promoter of the tetracycline resistance gene. Translation is coupled to the Shine-Dalgarno sequences of this same $tet^r$ gene in a manner strictly analogous to the procedures outlined above for vectors suitable for use in other hosts.

(iv) Yeast Vectors

Maintenance of foreign DNA introduced into yeast can be effected in several ways as described by Botstein, D. and Davis, R. W., in *The Molecular Biology of the Yeast Saccharomyces,* Cold Spring Harbor Laboratory, Strathern, Jones and Broach, eds., pp. 607–636 (1982), specifically incorporated hereby by reference. One preferred expression system for use with host organisms of the genus Saccharomyces harbors the IL-1i gene on the 2 micron plasmid. The advantages of the 2 micron circle include relatively high copy number and stablility when introduced into cir° strains. These vectors preferably incorporate the replication origin and at least one antibiotic resistance marker from pBR322 to allow replication and selection in *E. coli*. In addition, the plasmid will preferably have the two micron sequence and the yeast LEU2 gene to serve the same purposes in LEU2 defective mutants of yeast.

If it is contemplated that the recombinant IL-1 inhibitors will ultimately be expressed in yeast, it is preferred that the cloning vector first be transferred into *Escherichia coli*, where the vector would be allowed to replicate and from which the vector would be obtained and purified after amplification. The vector would then be transferred into the yeast for ultimate expression of the IL-1 inhibitor.

(c) Mammalian Cells

The cDNA for the IL-1 inhibitor will serve as the gene for expression of the inhibitor in mammalian cells. It should have a sequence that will be efficient at binding ribsomes such as that described by [Kozak, in Nucleic Acids Research 15:8125–8132 (1987), specifically incorporated herein by reference,] and should have coding capacity for a leader sequence (see section 3(a)(vi)) to direct the mature protein out of the cell in a processed form. The DNA restriction fragment carrying the complete cDNA sequence can be inserted into an expression vector which has a transcriptional promoter and a transcriptional enhancer as described by Guarente, L. in Cell 52:303–305 (1988) and Kadonaga, J. T. et ale., in Cell 51:1079–1090 (1987), both of which are specifically incorporated herein by reference. The promoter may be regulatable as in the plasmid pMSG (Pharmacia Cat. 27450601) if constitutive expression of the inhibitor is harmful to cell growth. The vector should have a complete polyadenylation signal as described by Ausubel, F. M. et al. in Current Protocols in Molecular Biology, Wiley (1987), specifically incorporated herein by reference, so that the mRNA transcribed from this vector is processed properly. Finally, the vector will have the replication origin and at least one antibiotic resistance marker from pBR322 to allow replication and selection in *E. coli*.

In order to select a stable cell line that produces the IL-1 inhibitor, the expression vector can carry the gene for a selectable marker such as a drug resistance marker or carry a complementary gene for, a deficient cell line, such as a dihydrofolate reductase (dhfr) gene for transforming a dhfr$^-$ cell line as described by Ausubel et al., supra. Alternatively, a separate plasmid carrying the selectable marker can be cotransformed along with the expression vector.

4. Host Cells/Transformation

The vector thus obtained is transferred into an appropriate host cell. These host cells may be microorganisms or mammalian cells.

(a) Microorganisms

It is believed that any microorganism having the ability to take up exogenous DNA and express those genes and attendant operational elements may be chosen. After a host organism has been chosen, the vector is transferred into the host organism using methods generally known to those of ordinary skill in the art. Examples of such methods may be found in Advanced Bacterial Genetics by R. W. Davis et al., Cold Spring Harbor Press, Cold Spring Harbor, N.Y., (1980), which is specifically incorporated herein by reference. It is preferred, in one embodiment, that the transformation occur at low temperatures, as temperature regulation is contemplated as a means of regulating gene expression through the use of operational elements as set forth above. In another embodiment, if osmolar regulators have been inserted into the vector, regulation of the salt concentrations during the transformation would be required to insure appropriate control of the foreign genes.

It is preferred that the host microorganism be a facultative anaerobe or an aerobe. Particular hosts which may be preferable for use in this method include yeasts and bacteria. Specific yeasts include those of the genus Saccharomyces, and especially *Saccharomyces cerevisiae*. Specific bacteria include those of the genera Bacillus, Escherichia, and Pseudomonas, especially *Bacillus subtilis* and *Escherichia coli*. Additional host cells are listed in Table I, supra.

(b) Mammalian Cells

The vector can be introduced into mammalian cells in culture by several techniques such as calcium phosphate:DNA coprecipitation, electroporation, or protoplast fusion. The preferred method is coprecipitation with calcium phosphate as described by Ausubel et al., supra.

Many stable cell types exist that are transformable and capable of transcribing and translating the cDNA sequence, processing the precursor IL-1i and secreting the mature protein. However, cell types may be variable with regard to glycosylation of secreted proteins and post-translational modification of amino acid residues, if any. Thus, the ideal cell types are those that produce a recombinant IL-1 inhibitor identical to the natural molecule.

5. Culturing Engineered Cells

The host cells are cultured under conditions appropriate for the expression of the IL-1 inhibitor. These conditions are generally specific for the host cell, and are readily determined by one of ordinary skill in the art in light of the published literature regarding the growth conditions for such cells and the teachings contained herein. For example, Bergey's Manual of Determinative Bacteriology, 8th Ed., Williams & Wilkins Company, Baltimore, Md., which is specifically incorporated herein by reference, contains information on conditions for culturing bacteria. Similar information on culturing yeast and mammalian cells may be obtained from Pollack, R. Mammalian Cell Culture, Cold Spring Habor Laboratories (1975), specifically incorporated herein by reference.

Any conditions necessary for the regulation of the expression of the DNA sequence, dependent upon any operational elements inserted into or present in the vector, would be in effect at the transformation and culturing stages. In one embodiment, cells are grown to a high density in the presence of appropriate regulatory conditions which inhibit the expression of the DNA sequence. When optimal cell density is approached, the environmental conditions are altered to those appropriate for expression of the DNA sequence. It is thus contemplated that the production of the IL-1 inhibitor will occur in a time span subsequent to the growth of the host cells to near optimal density, and that the resultant IL-1 inhibitor will be harvested at some time after the regulatory conditions necessary for its expression were induced.

6. Purification (a) IL-1i Produced From Microorganisms

In a preferred embodiment of the present invention, the recombinant IL-1 inhibitor is purified subsequent to harvesting and prior to assumption of its active structure. This, embodiment is preferred as the inventors believe that recovery of a high yield of re-folded protein is facilitated if the protein is first purified. However, in one preferred, alternate embodiment, the IL-1 inhibitor may be allowed re-fold to assume its active structure prior to purification. In yet another preferred, alternate embodiment, the IL-1 inhibitor is present in its re-folded, active state upon recovery from the culturing medium.

In certain circumstances, the IL-1 inhibitor will assume its proper, active structure upon expression in the host microorganism and transport of the protein through the cell wall or membrane or into the periplasmic space. This will generally occur if DNA coding for an appropriate leader sequence has been linked to the DNA coding for the recombinant protein. If the IL-1 inhibitor does not assume its proper, active structure, any disulfide bonds which have formed and/or any noncovalent interactions which have occurred will first be disrupted by denaturing and reducing agents, for example, guanidinium chloride and beta-mercaptoethanol, before the IL-1 inhibitor is allowed to assume its active structure following dilution and oxidation of these agents under controlled conditions.

For purification prior to and after refolding, some combination of the following steps is preferably used: anion exchange chromatography (MonoQ or DEAE-Sepharose), gel filtration chromatography (superose), chromatofocusing (MonoP), and hydrophobic interaction chromatography (octyl or phenyl sepharose). Of particular value will be antibody affinity chromatography using the IL-li-specific monoclonal antibodies (described in Example 4).

(b) IL-1i Produced from Mammalian Cells

IL-1i produced from mammalian cells will be purified from conditioned medium by steps that will include ion exchange chromatography and immunoaffinity chromatography using monoclonal antibodies described in Example 4. It will be apparent to those skilled in the art that various modifications and variations can be made in the processes and products of the present invention. Thus, it is intended that the present invention cover the modifications and variations of this invention provided they come within the scope of the appended claims and their equivalents.

It is to be understood that application of the teachings of the present invention to a specific problem or environment will be within the capabilities of one having ordinary skill in the art in light of the teachings contained herein. Examples of the products of the present invention and representative processes for their isolation and manufacture appear in the following.

The following examples illustrate various presently preferred embodiments of the present invention. The publications provided in these examples are specifically incorporated by reference wherein.

EXAMPLES

Example 1

Protein Preparation

A. Materials

Hank's Balanced Salt Solution (HBSS) and RPMI were purchased from Mediatech, Washington, D.C. Lymphoprep was obtained from Accurate Chemical and Scientific Corp., Westbury, N.Y. Human IgG, MTT, rabbit anti-prostaglandin $E_2$ antiserum, ammonium bicarbonate, dithiothreitol, complete and incomplete Freund's adjuvants, hypoxanthine, aminopterin, and thymidine were purchased from Sigma Chemical Co., St. Louis, Mo. C3H/HeJ mice were purchased from Jackson Labs, Bar Harbor, Me. BALB/C mice and P3 myeloma cells were obtained from Drs. John Kappler and Philippa Marrack at the National Jewish Center for Immunology and Respiratory Medicine (NJC/IRM), Denver, Colo. Recombinant human IL-1 was obtained from Cistron Biotechnology, Pine Brook, N.J. Purified phytohemagglutinin was purchased from Wellcome Diagnostics, Research Triangle Park, N.C. Human foreskin fibroblasts from primary cultures were obtained from Dr. Richard Clark at the NJC/IRM, Denver, Colo. Monoclonal mouse anti-rabbitt IgG antibodies were purchased from AIA reagents, Aurora, Colo. Low methionine RPMI was made using a Select-Amine kit from GIBCO Laboratories, Grand Island, N.Y. [$^{35}$S]-methionine, diphenyoxazole, and [$^{14}$C]-iodoacetic acid were obtained from DuPont-NEN, Chicago, Ill. Fetal calf serum was purchased from HyClone Laboratories, Logan, Utah. Mono Q and Superose 12 columns were purchased from Pharmacia, Inc., Piscataway, N.J. C4-reversed phase columns were obtained from Synchrom, Inc., Lafayette, Ind. C8-reversed phase columns were obtained from Applied Biosystems, Inc., Foster City, Calif. Acetonitrile and polyethylene glycol 8000 were purchased from J. T. Baker Chemical Co., Phillipsburg, N.J. Trifluroacetic acid and guanidine hydrochloride were obtained from Pierce Chemicals, Rockford, Ill. Endoproteinase Lys C was obtained from Boehringer Mannheim Biochemicals, Indianapolis, Ind. The microtitering plates used for $PGE_2$ ELISA were Nunc-Immuno Plate I obtained from Intermountain Scientific Corporation, Bountiful, Utah. The plates used for hybridoma production were from Costar, Cambridge, Mass.

B. Generation of Monocyte IL-1 Inhibitor

Human leukocytes were obtained from normal donors by leukophoresis, resuspended in Hank's balanced salt solution (HBSS) at 1 part packed cells to 1 part HBSS, underlayed with Lymphoprep and spun at 400×g for 30' at room temperature. The mononuclear fraction was taken (typically 4–5×10$^9$ cells were obtained per donor), washed in HBSS without $Ca^{++}$ or $Mg^{++}$, suspended in serum-free RPMI and plated on petri dishes coated with normal human IgG made LPS free by chromatography over Sephapex G200 (6×10$^7$ cells in 10 ml per 100 mm dish). All reagents contained less than 10 pg/ml LPS. The cells were cultured 24–28 hr, and the resulting conditioned medium constituted the crude IL-1 inhibitor (IL-1i) supernatant. Typically, the cells from one donor yielded 700–900 ml crude IL-1i supernatant.

C. Assays for the IL-1 Inhibitor

Two IL-1 assays have been used routinely to detect the IL-1i. Thymocytes (1×10$^6$ cells from 4 to 6 week old C3H/HeJ mice) respond to 1.0 unit/ml of recombinant human IL-1 plus 1 ug/ml phytohaemaglutinin by proliferating half-maximally, as measured by $^3$H-thymidine incorporation or uptake of the tetrazolium salt MTT (Mosmann, T., J. Immunol. Method, 65:55–61 (1983)) after three days of stimulation. Crude IL-1i supernatant fully inhibits this proliferative response at a $^1$/$_{10}$ dilution. Human dermal fibroblasts (1×10$^5$ cells per well in a 96 well plate) typically respond to 0.5 units/ml recombinant human IL-1 by secreting, at 6 hours of stimulation, approximately 50,000 pg/ml $PGE_2$ that can be measured by ELISA. This assay is as sensitive to IL-1i as is the thymocyte assay.

D. Metabolic Labeling of the IL-1 Inhibitor

The IL-1i was metabolically labeled by culturing mononuclear leukocytes for 48 hours on IgG-coated plates (as described in B) in serum-free RPMI containing only 0.75 ug/ml cold methionine (15ug/ml is normal) and to which was added 0.5 mCi $^{35}$S-methionine (1151 Ci/mmol) per 10$^7$ cells. Control labelings were performed identically except that the plates were coated with fetal calf serum rather than IgG. Assays on such control supernatants showed that very little IL-1i was secreted when the cells were cultured on fetal calf serum-coated plates.

E. Purification of the IL-1 Inhibitor Protein

Figure 1B:
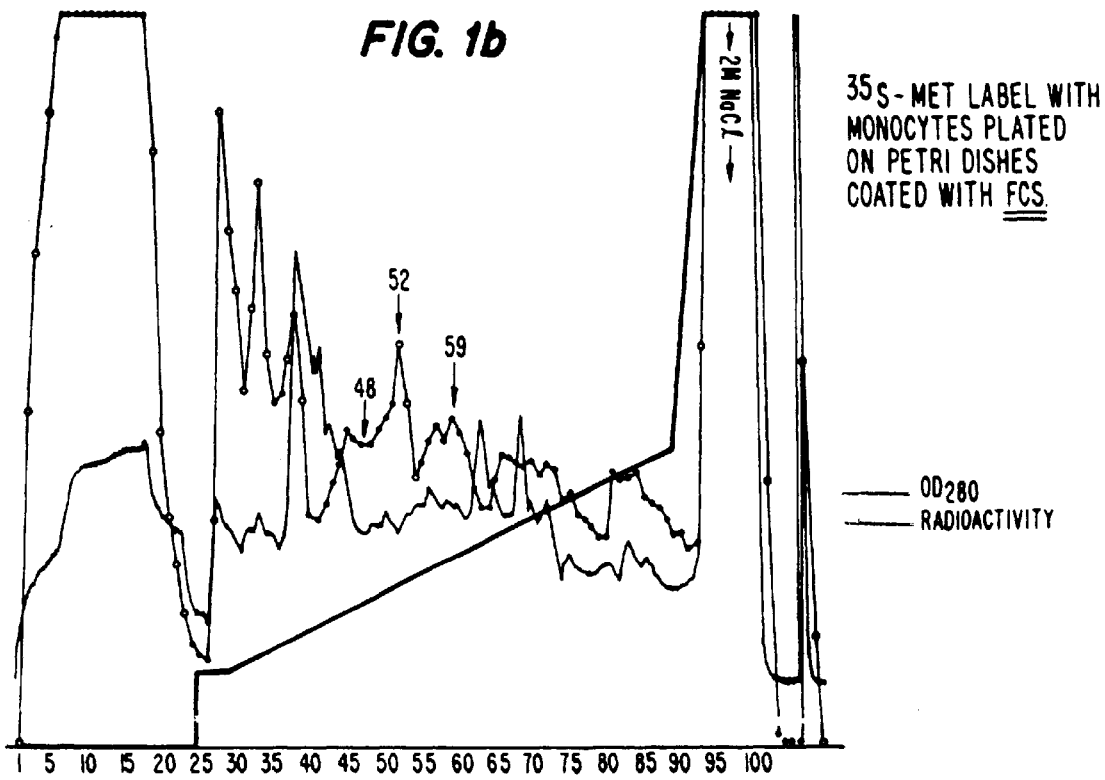
Figure 2A:
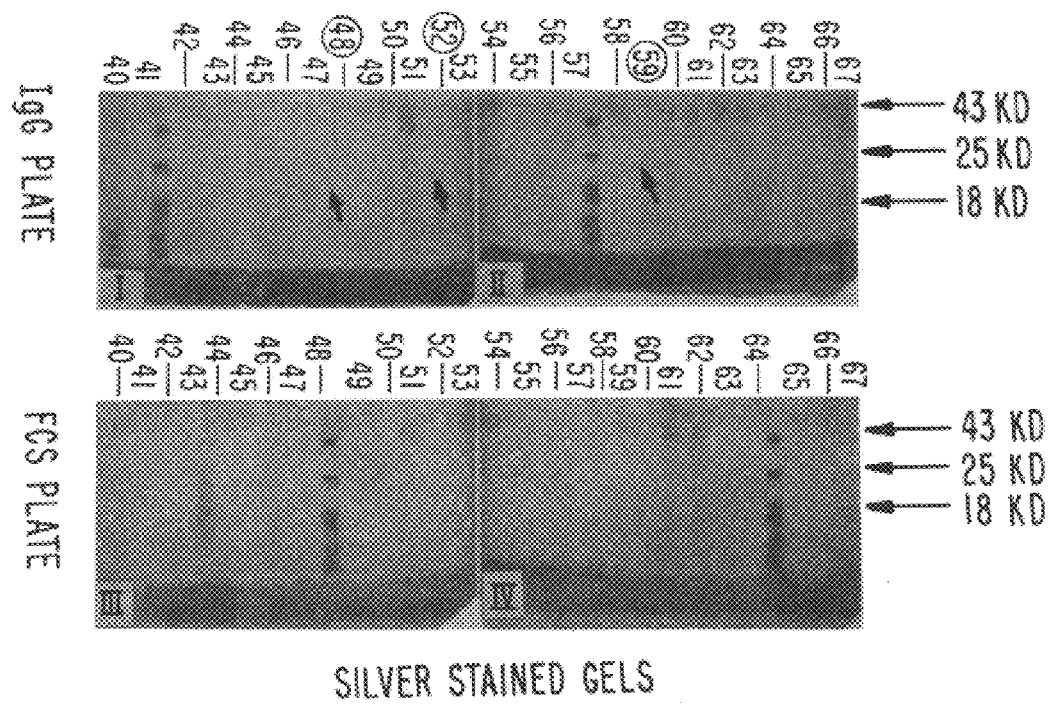
FIG. 2a shows silver stained gels of fractions from the regions indicated in FIGS. 1a and 1b.
Figure 2B:
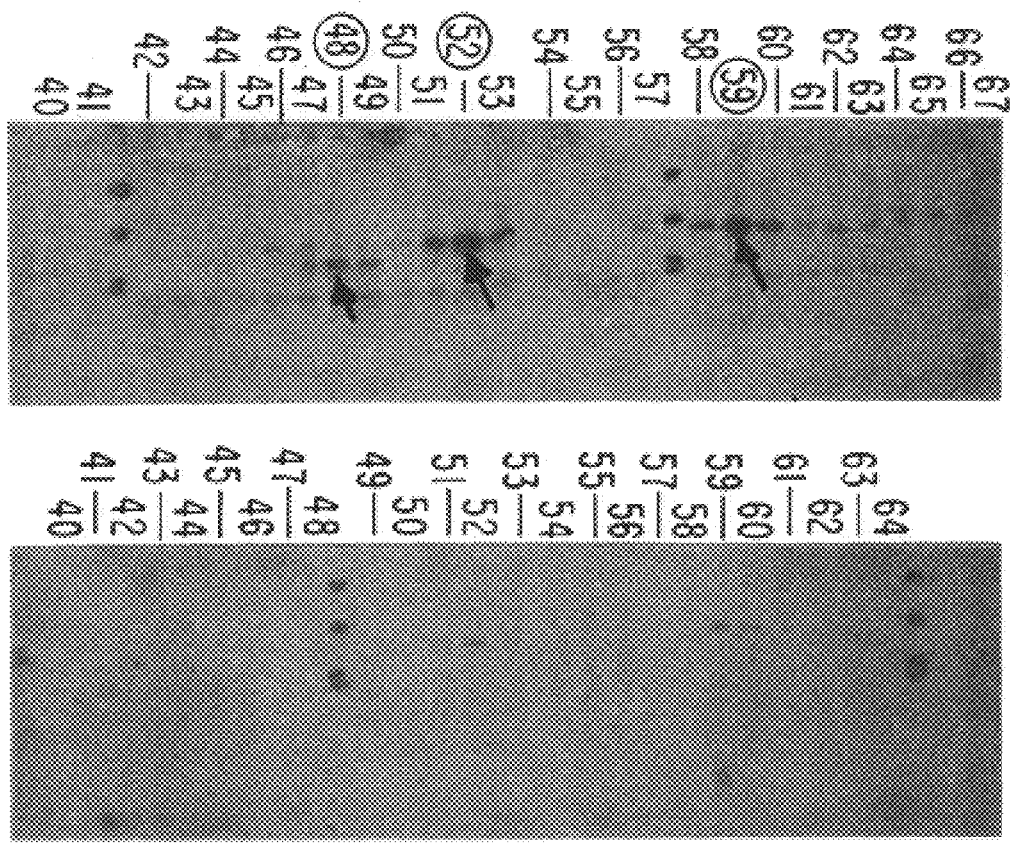

Crude IL-1i supernatants were made 1.0 M in sodium chloride, incubated on ice for 1 hour and centrifuged at 10,000 rpm for 15 minutes. The supernatants, which contained all of the inhibitor activity but only 20% of the initial protein, were then dialyzed extensively at 4° C. versus 0.025M Tris, pH 7.6 containing 0.1% sucrose (the A buffer) for gradient fractionation of proteins on a Mono Q anion exchange column. Following dialysis the inhibitor-containing solutions were recentrifuged at 10,000 rpm for 15 minutes and then passed through 0.22 u nylon filters. The supernatants were typically combined with 10 ml of similarly prepared supernatant from a metabolic labeling and loaded onto Mono Q-Superose (Pharmacia FPLC) columns with bed volumes of either 1.0 ml or 8.0 ml, washed with A buffer until the $OD_{280}$ of the effluent returned to baseline, and carefully chromatographed using a linear sodium chloride gradient (0.025M to 0.10M) in buffer A. Column fractions were collected and analyzed for radioactivity and bioactivity. Samples of each fraction were also run on reduced 12.5% SDS-PAGE, silver stained, permeated with diphenyloxazole, dried and put onto film to obtain autoradiographic data. FIG. 1a shows the protein profile of the Mono Q chromatography of 40 ml crude IL-1i supernatant mixed with 3 ml of metabolically labeled IL-1i supernatant. Superimposed are the amount of radioactivity found in 50 ul of each fraction as well as the IL-1i bioactivity as measured in the $PGE_2$-production assay. Two major and one minor radioactive species are shown that perfectly correlate with three peaks of bioactivity. FIG. 1b shows the similar chromatography of 15 ml of crude IL-1i supernatant mixed with 3 ml of supernatant from monocytes metabolically labeled on plates coated with fetal calf serum (FCS) rather than IgG. The levels of the three radioactive species discussed above are markedly diminished. FIG. 2a shows silver stained gels run on the fractions from the regions of interest in the chromatographies shown in FIGS. 1a and 1b. Note that the fractions of peak radioactivity and bioactivity in FIG. 1a (fractions 52 and 59) both show a major band at 22 Kd (marked with arrows) on SDS-PAGE. The third species (fraction 48 in FIG. 1a) shows a band at 20 kD on SDS-PAGE. Gel filtration experiments on crude IL-1i have shown that the active molecule has a molecular weight of 18–25 Kd. FIG. 2b is an autoradiogram of the gels shown in FIG. 2a. It can be readily seen that the protein bands at 20 and 22 Kd are the major radioactive species in those fractions.

Summarizing these results, we have shown that the metabolic labeling of monocytes plated on petri dishes coated with IgG showed that very little IL-1i was secreted when the cells were the cells are plated on dishes coated with FCS. These induced radioactive species perfectly co-chromatograph with several species of IL-1i bioactivity on Mono Q, and gels and resulting autoradiograms show that the three major induced molecules are proteins of the predicted molecular weight for IL-1i.

Figure 3A:
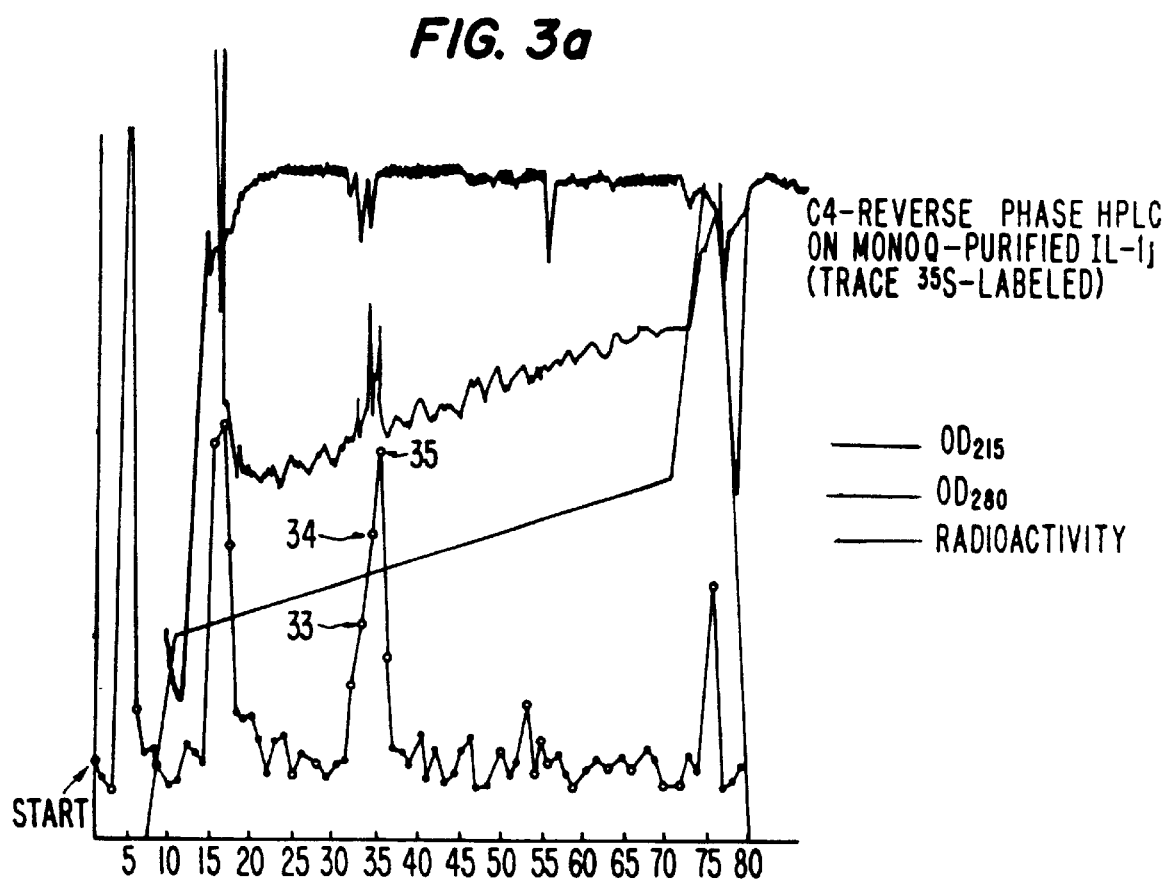
FIGS. 3a, b and c present data on the purified IL-1i of Example 1.
Figure 3B:
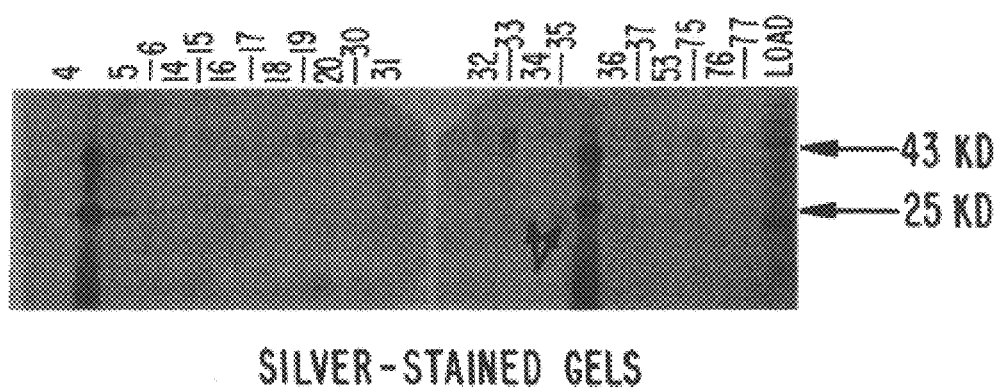
Figure 3C:
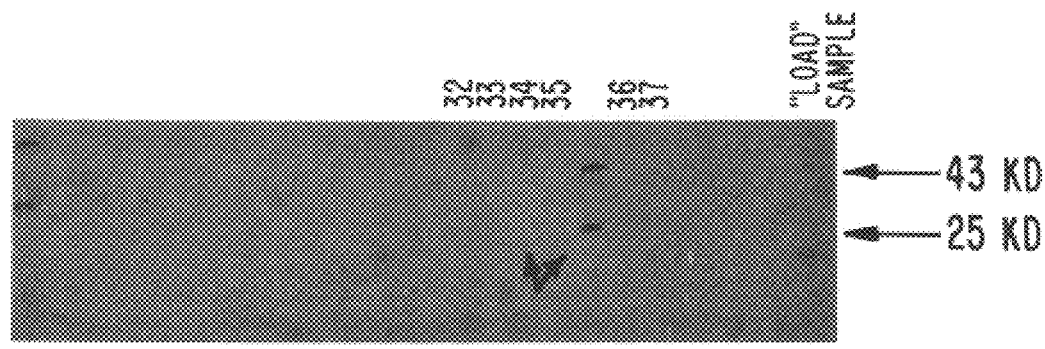
FIG. 3c presents autoradiograms of the gels in FIG. 3b.

The IL-1i molecules were further purified for sequencing in two ways. First, Mono Q fractions with peak bioactivity and radioactivity were loaded onto a C4-reversed phase column and eluted with an $H_2O/0.1\%TFA$: acetonitrile/ 0.1%TFA gradient. Since the IL-1i molecule was trace labeled, samples from each fraction were directly counted for radioactivity and were also analyzed by SDS-PAGE followed by autoradiography. FIG. 3a shows such a chromatograph with the radioactivity pattern superimposed The silver stained gels run on samples from each fraction (FIG. 3b) and subsequent autoradiograms of the gels (FIG. 3c) shows that the IL-1i molecule is found in fractions 32–36.

Figure 4A:
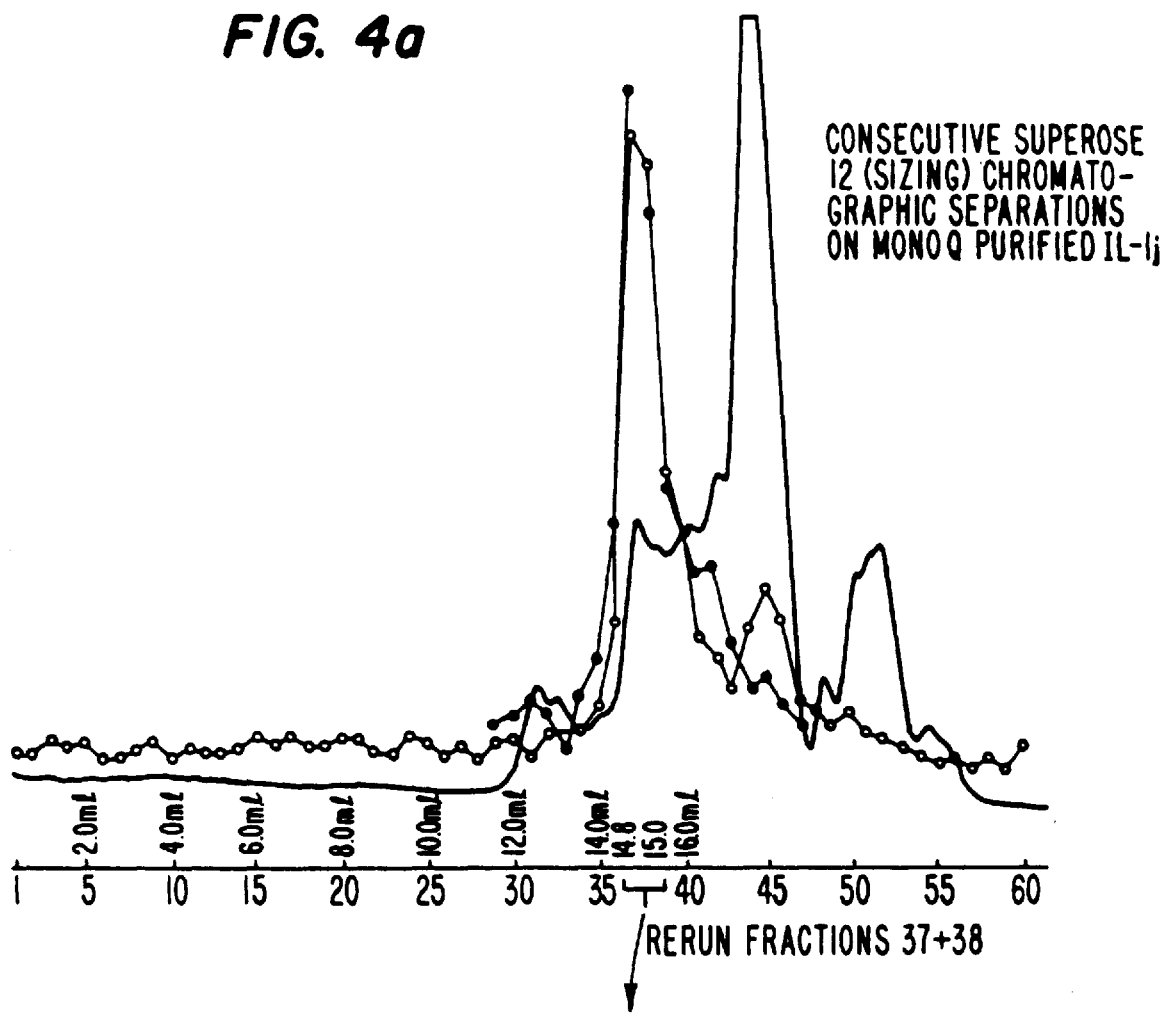
FIGS. 4a and b present the results of gel filtration chromatograms of Mono Q-purified IL-1i.
Figure 4B:
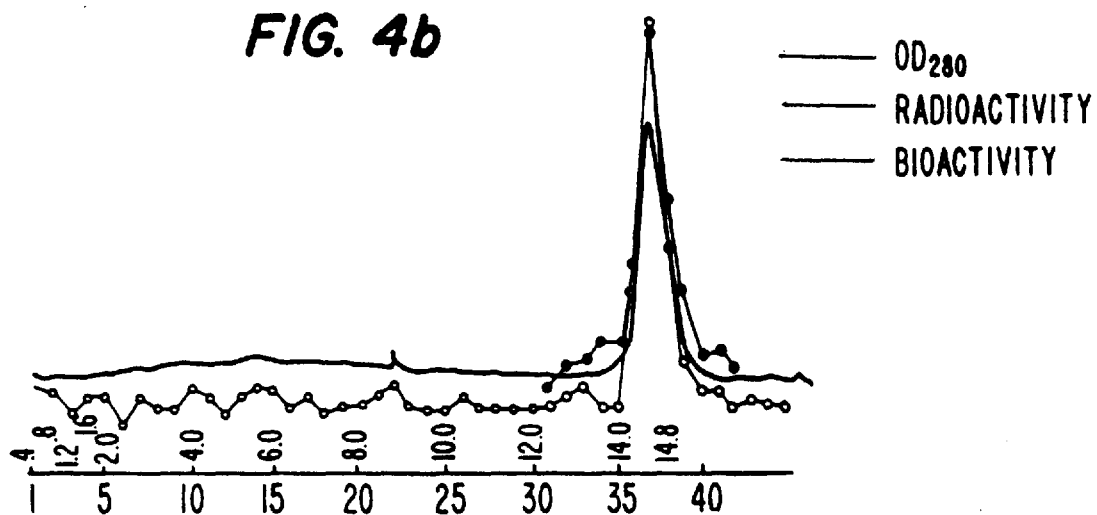

These fractions were dried down and sequenced. Alternatively the peak Mono Q fractions were dried by Speed Vac, resuspended in 0.4 ml 0.05 M $NH_4HCO_3$ and directly chromatographed two times on a 10×300 mm Superose 12 gel filtration column (Pharmacia FPLC) equilibrated in the same buffer, as shown in FIGS. 4a and 4b. Fractions were collected and samples of each were tested for radioactivity and bioactivity and were analyzed by silver stained and autoradiographed SDS-PAGE. Appropriate fractions were then dried on a speed vac and sequenced.

Example 2

Proposed Sequencing of the IL-1 Inhibitor

Prior to sequencing, samples were dissolved in 6 M guanidine-HCl, pH 8.6, reduced for 4 hours at 37° C. under $N_2$ with 100-fold molar excess dithiothreitol over protein, and alkylated for 1 hour with 400-fold excess $^{14}C$-iodoacetic acid. In that case, the reactions would be desalted on a C8-reversed phase column, eluted, and partially dried. N-terminal sequences will be determined using an Applied Biosystems Protein Sequencer. To obtain internal sequences, samples which may have been reduced and alkylated would be digested with cyanogen bromide or proteolytic enzymes using methods known to those of ordinary skill in the art. Reactions will be dried, dissolved in 0.1% $TFA/H_2O$, and peptides will be separated using a C8-reverse phase column.

Example 3

Purification and Sequencing of the Species of IL-1 Inhibitors

A. IL-1i-X, IL-1i-a and IL-1i-b Species

The Mono Q purification of IL-1i resolves the biological activity into three major species, as shown in FIG. 1a and described in Example 1, where the peak fractions for this activity are 48, 52, and 59. SDS-PAGE on samples of these fractions, as shown in FIG. 2a, reveal pertinent species at 20 kD, 22 kD, and 22 kD, respectively. Western analysis of such gels, using the mouse antisera discussed in Example 4 below, stains all three of these species. When IL-1i is prepared from cells metabolically labeled with $^{35}S$-methionine, during growth on plates coated with IgG, each of these bands is radioactive (as shown in FIG. 2b, the autoradiogram of the above-mentioned gel). Based on the logic discussed in Example 1, namely that parallel cells incubated in a non-inducing condition do not produce the IL-1$_i$ bioactivity and do not produce these radioactive bands, we can conclude that these three species account for the biological activity. We have tentatively named these species IL-1i-X, IL-1i-a, and IL-1i-b, respectively.

B. Purification and Sequencing of IL-1i-X

Mono Q fractions containing IL-1i-X and/or IL-1i-a were further purified by reversed-phase HPLC chromatography on a Synchropak RP-4 (C4) column, and radioactive species were submitted for sequence analysis. Numerous attempts at directly sequencing RP-HPLC-purified IL-1i-a and IL-1i-b have failed, suggesting that they are chemically blocked at their N-termini. However, one preparation of IL-1i-a (IL-1i-aB2p42) yielded the following sequence:

```
    1       5         10        15        20
    R P S G R K S S K M Q A F _ I S D V N Q
``` and subsequent preparations of IL-1i-x, similarly purified by C4 RP-HPLC, have produced the same sequence:

```
              1         5         10        15        20
PrepKxF24     _ _ _ _ _ _ _ _ _ _ M Q A F _ I D _ V N _ K _ F
and
PrepKxF23     R P _ _ R K _ L K M Q A F _ I
```

These are obviously part of the sequence found in the initial attempt at sequencing IL-1i-a. It is the inventors' conclusion that the sequence data shown is the N-terminus of the 20 kD species called IL-1i-X.

In these and all subsequent sequences an underlined position indicates either an inability to identify a residue or that ambiguity exists with respect to the residue identified. When two or more residues are put in one position, it indicates that. more than one amino acid was detected at that sequencing step, and the more likely correct residue is on top.

C. Generation, Purification, and Sequencing of Peptides of IL-1i-a and IL-1i-b

Figure 8A:
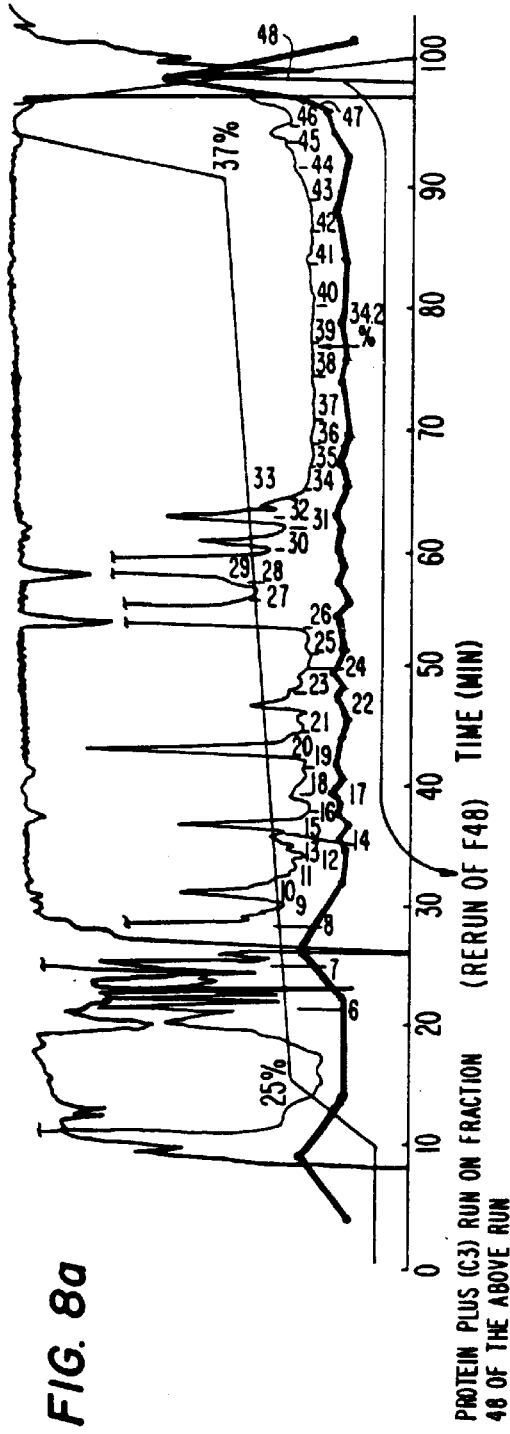
FIGS. 8a–d present data on IL-1i-α.
Figure 8B:
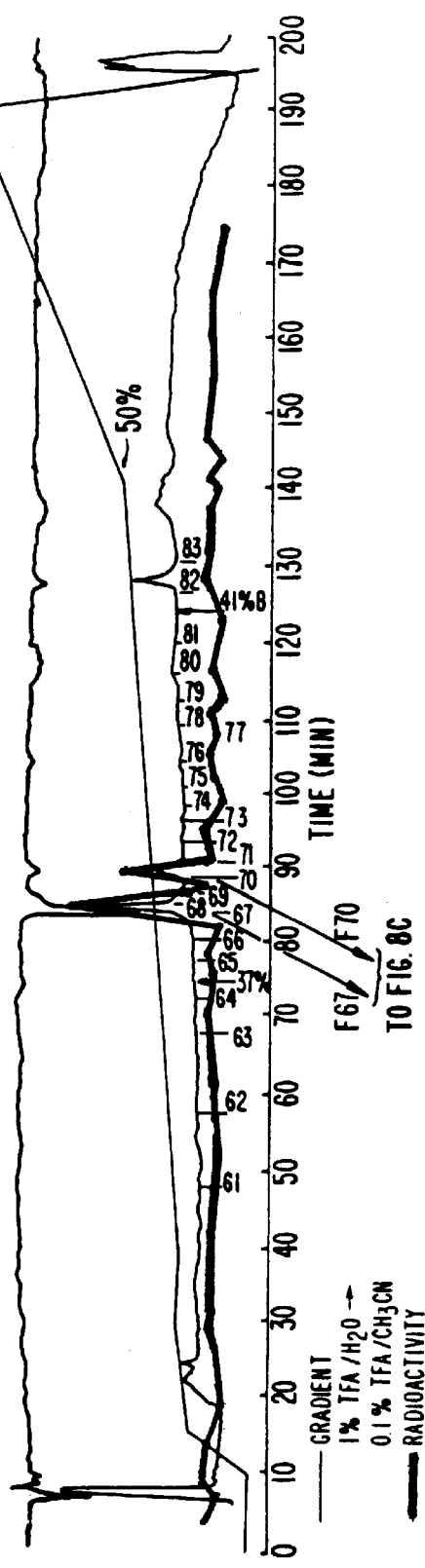
Figure 8C:
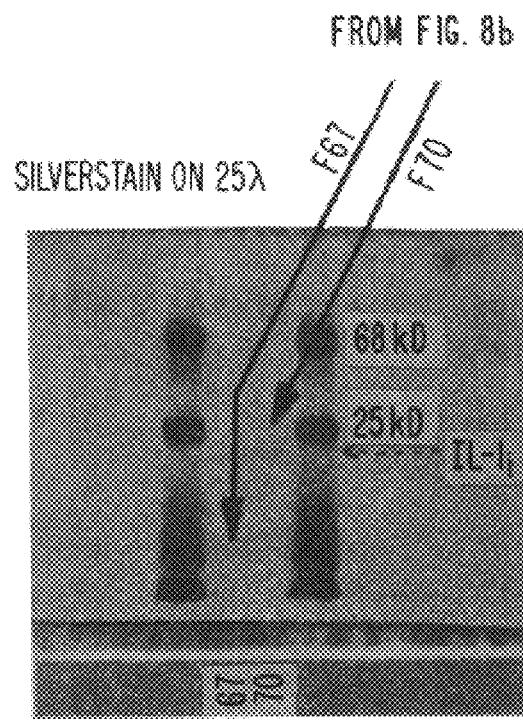
Figure 8D:
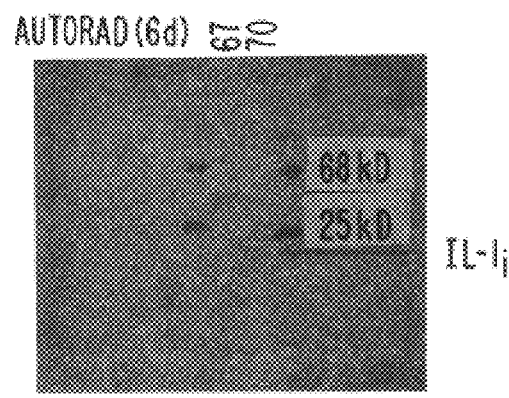
Figure 9B:
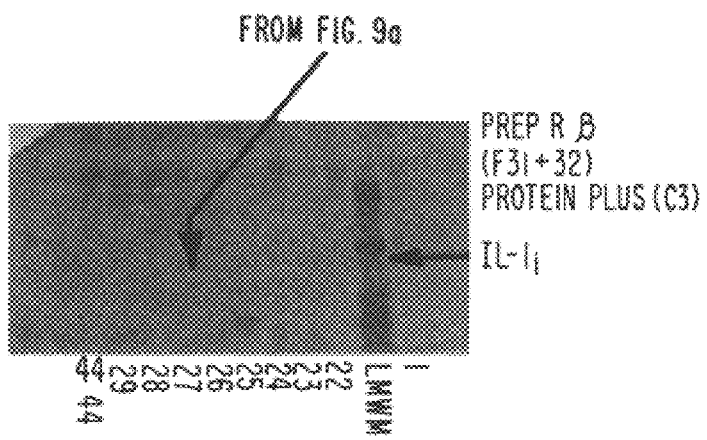

Since IL-1i-a and IL-1i-b are apparently chemically blocked at their N-termini, peptides of each were generated by endoproteinase digestion. Specifically, Mono Q fractions containing either IL-1i-a or IL-1i-b were passed through a 4.6×250 am C3-RPHPLC column (Zorbax Protein Plus), an acceptable alternative to the C-4 columns used in all previous experiments. Very gradual gradients (0.2% acetonitrile per minute at 0.5 ml/min) resolved the IL-1i-a (FIGS. 8a,b) or IL-1i-b (FIG. 9a) away from the major contaminating radioactive species, human lysozyme. The identities of the purified species were confirmed by the presence of a single, radioactive, 22 kD protein on SDS-PAGE and subsequent autoradiograms (FIGS. 8c,d and 9b). The proteins were hand-collected into siliconized glass tubes and to each was added 25 ml of a 0.2% Tween-20 solution. The IL-1i-containing fractions were then reduced in volume on a Speed-Vac to 50 ml, brought up to 300 ml by the addition of 1% $NH_4HCO_3$, followed by the addition of 1 mg of endoproteinase. In the case of IL-1i-a, the enzyme used was Endoproteinase Lys C (Boehringer-Mannheim), while IL-1i-b was cleaved with Endoproteinase Asp N (Boehringer-Mannheim). Cleavage was carried out at 37° C. for 16 hr, and then the volume of the reaction mix was reduced to 50 ml on a Speed Vac.

Figure 11:
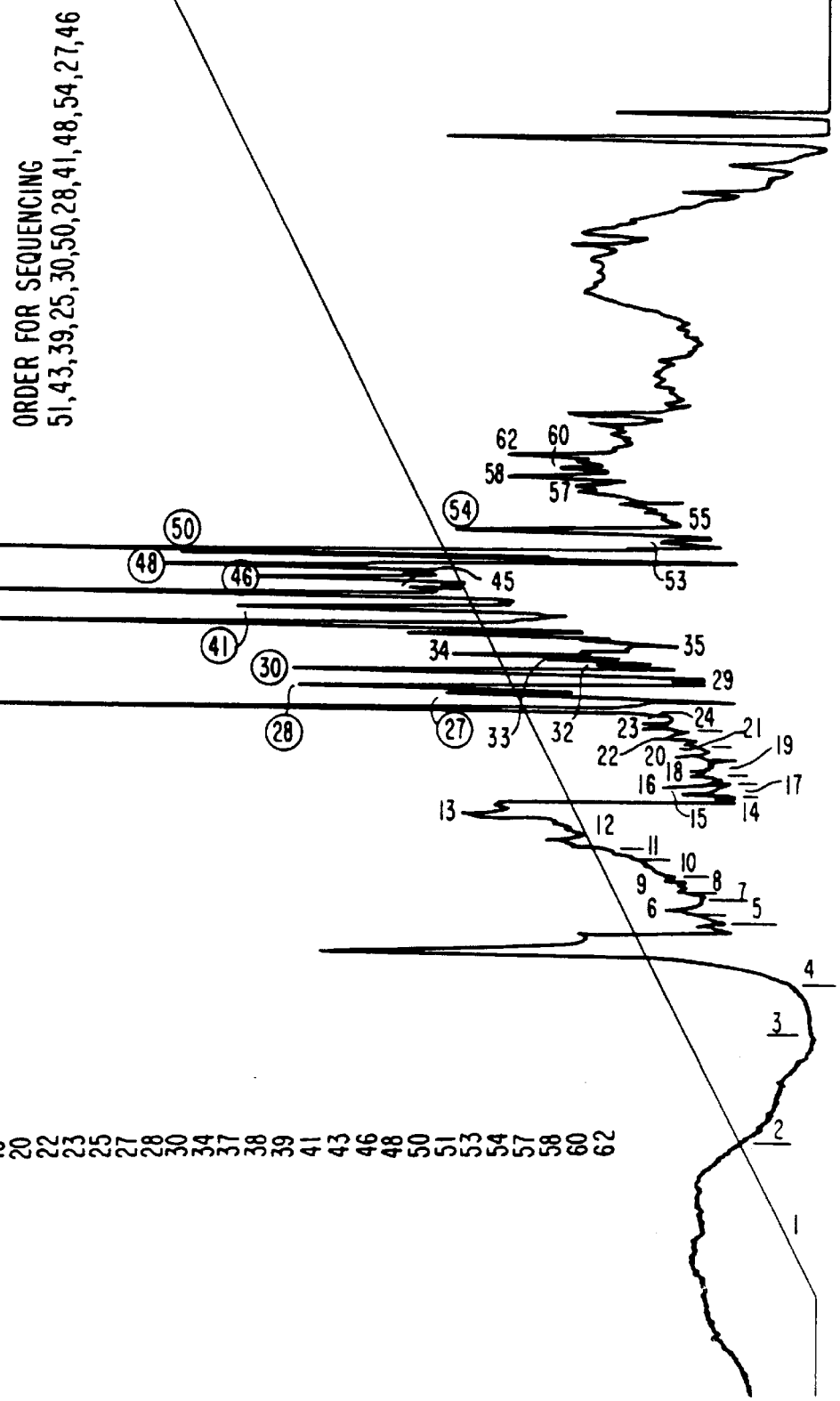
FIG. 11 presents data of IL-1i-β peptide separation.

In the case of IL-1i-a, the sample was directly chromatographed, whereas the IL-1i-b sample was first reduced by the addition of 5ml of 50 mM dithiothreitol in 2 M Tris, pH 8.0, reacted for 30 min at 37° C., and then carboxymethylated by addition of 1.1 umole $^3$H-iodoacetic acid in 10 ml ethanol (reacted 30 min at 37° C. in the dark). Separation of the peptides was performed on a 2.1x250 mm Brownlee Aquapore RP-300 (C8) narrow-bore column at a flow rate of 100 ml/min using a Beckman HPLC outfitted with microbore hardware and microbore-compatible pumps. A 200 min 0–100% linear gradient was used ($H_2O$/0.1% TFA to acetonitrile/0.1% TFA). The peptide separations are shown in FIGS. 10 and 11. The sequence information obtained is as follows:

```
              1         5         10
RαLysC-41     M Q A F _ I _ D V N Q K 1         5         10        15        20        25
                                                                K         P
RαLysC-53     _ F Y L _ N N Q L V A _ Y L Q G P N V N L E E Q I D N _ N 1         5
                        I         Y
RαLysC-61     _ F A T T R H V H 1         5
RαLysC-31     F Y F Q E D 1         5         10        15        20
              G   E               S   I T       S
RαLysC-37     _ Q D F T _ L Q L E A N R Q S Q L G E Q 1         5         10        15        20
RαLysC-35     _ _ _ E T R L Q L E A V _ I T D L L E N 1         5         10        15        20        25
                        Q K T F   L                   G
RβAspN-51     D V N P I E P Y A R N N Q L V A S Y L Q G P N V N L 1         5         10
RβAspN-43     D E G V M V T K F Y F Q 1         5         10        15
                                            K
RβAspN-39     _ P S G R K S S F M Q A F R T Q 1         5
RβAspN-25     D K R F A F I R 1         5         10
                  S     L         Q
RβAspN-30     D _ E V N H L K K I S
```

Two of the peptide sequences are obviously related to that which was obtained earlier from IL-1i-X. One of these, RαLysC-41, is an IL-1i-a sequence, and the other, RbAspN-51, is an IL-1i-b sequence, arguing that the three species of IL-1i are at least closely related proteins if not chemically and/or physically modified forms of a single original IL-1i molecule. If the listed sequences are combined, the following composite sequences result:

$2 \times 10^7$ P3 cells per [8] splenic B cells and spun down. The cells were fused by the dropwise addition of 1 ml of warm, gassed (5% $CO_2$) PEG 6000 (40% polyethylene glycol 6000: 60% minimal essential medium) to the dry pellet. Fused cells were washed with BSS and resuspended in 10 ml of rich media (10% FBS) containing $2 \times 10^5$ peritoneal cells per ml and the pellet was gently broken up using a 10 ml pipet. The volume was adjusted to 20 ml with the addition of more

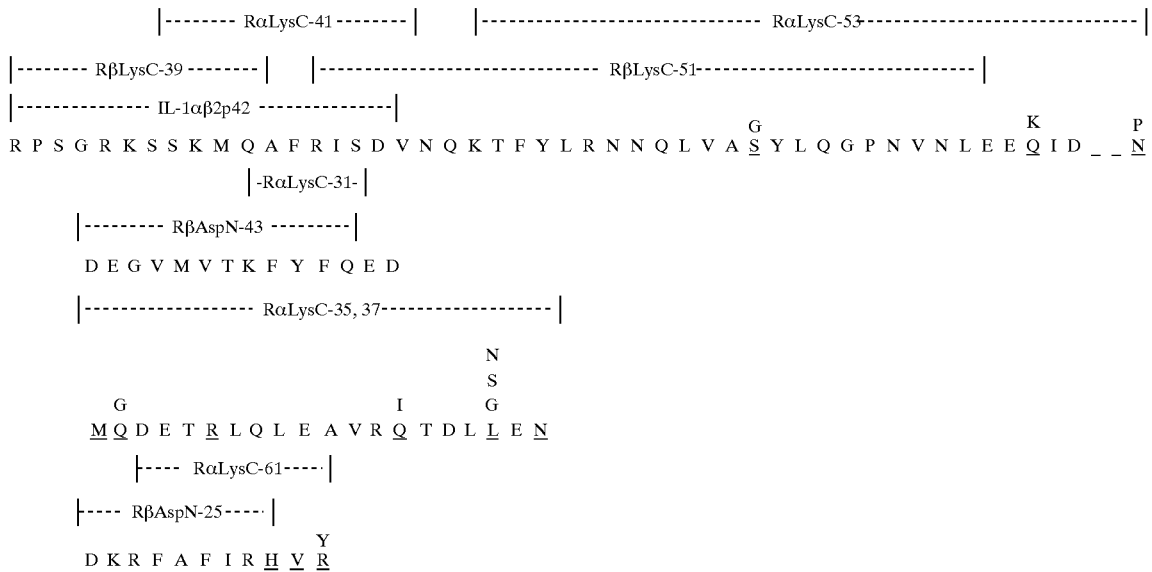

These composite sequences appear to be present in no other known polypeptides listed in the most recently updated Protein Identification Resource Database (PIR 16.0). The inventors believe that these sequences, or minor variants thereof, represent a class of molecules that are capable of acting as IL-1 inhibitors.

Example 4

Preparation of Antibodies Specific for the IL-1 Inhibitor

Figure 5A:
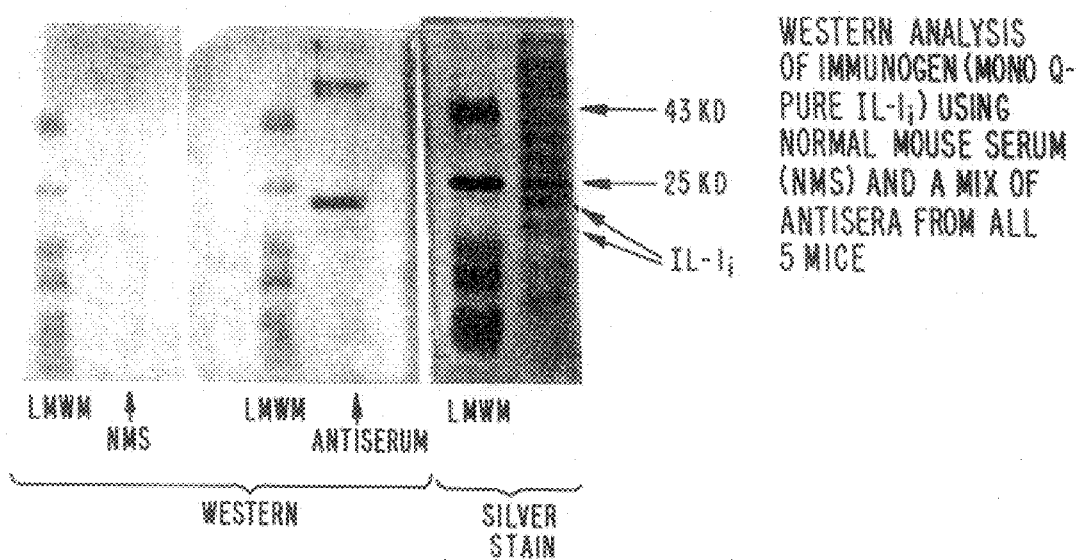
FIGS. 5a and b present Western analysis of mouse antisera.

Ten week old BALB/c mice were injected subcutaneously with IL-1i that was partially purified (400-fold) from crude supernatants by Mono Q-chromatography, dialyzed versus PBS, and emulsified with Complete Freund's Adjuvant. Each mouse received the IL-1i purified from 5 ml of crude supernatant. The mice were boosted every two weeks with an equivalent amount of IL-1i emulsifed with Incomplete Freund's Adjuvant, and serum samples were taken from the tails seven days after each boost. Antisera were tested for anti-IL-1i activity by Western analysis of transblots of the immunogen run on SDS-PAGE, as shown in FIG. 5a. FIG. 5b shows that all of the mice were making anti-IL-1i antibodies after three injections of IL-1i.

Since monoclonal antibodies will be of great value in cloning the IL-1i gene from an expression library, purifying the recombinant IL-1i protein, and studying the biology of the molecule, we have begun the process of making a battery of monoclonal antibodies specific for Il-1i. To produce B cell hybridomas, the above mice were injected intravenously with the same amount of IL-1i in saline 24 hours prior to removal of the spleens. Splenocytes were teased out of the spleens into cold balanced salt solution (BSS), washed two times with BSS, mixed with P3 myeloma cells at a ratio of peritoneal cells in media, and the cells were plated out in 96 well plates at 0.1 ml/well. Plates were placed in a gas incubater and treated in the following manner thereafter:

Day 1—Add 3×HAT (hypoxanthine, aminopterin, thymidine) in rich medium to a final concentration of 1×

Day 5—Change medium, replacing with 200 ul 11×HAT in rich medium

Day 10—Begin checking for hybrid growth. Change medium, replacing with 200 ul 1×HAT in rich medium containing $1.5 \times 10^6$ peritoneal cells per ml.

When hybrid cells are nearly confluent in a well the supernatants are transfered for testing, and the cells are gently scraped with a pipet tip and transfered to 1 ml culture wells containing 1×HAT in rich medium plus $3 \times 10^6$ peritoneal cells per ml.

The supernatants from the confluent wells are tested for anti-IL-1i activity using an ELISA in which partially purified IL-1i (Mono Q-purified material identical to that injected into the mice) is bound to microtitering wells. Normal mouse sera and hyperimmune antisera are used as the negative and positive controls, respectively. Positive supernatants will be retested by ELISA on plates coated with homogeneously purified IL-1i and by immunoprecipitation of purified metabolically labeled IL-1i. Positive cells will then be cloned by limiting dilution and injected into pristane-treated mice for the generation of ascites. Large quantities of IL-1i-specific antibodies can be produced by tissue culture or by massive generation and collection of ascitic fluid in mice. Purification of these antibodies and attachment thereof to insoluble beads will produce affinity adsorbents for the purification of the recombinant IL-1i protein.

Example 5

Cloning the Il-1i cDNA

It was shown that monocytes plated on IgG-coated petri dishes and cultured for 24 hours in the presence of [$^{35}$S]-methionine produced [$^{35}$S)-IL-1i which could be identified by its chromitographic properties on Mono Q.

In order to determine when (during the 24 hour period) IL-1i was being produced at a maximal rate, plated monocytes were exposed to ($^{35}$S]-methionine (pulsed) for a short, two-hour period, at which time a large excess of unlabelled methionine was added and incubated for an additional two hours. The medium was then collected and analyzed for radiolabelled IL-1i. This procedure was applied to monocytes at various times after plating of IgG coated plates and it was found that exposing monocytes to [$^{35}$S]-methionine at 15 hours after plating produced the maximal amount of [$^{35}$S]-IL-1i, indicating that IL-1i mRNA in monocytes was at its maximal level 15 hours after plating on IgG.

Fresh monocytes were then plated on LPS free IgG obtained as in Example IB. After incubating in RPMI media for 15 hours at 37° C., the cells are washed with phosphate buffered saline then lysed with 4M guanidinium thiocyanate; 25 mM sodium citrate, pH 7, 0.5% sarcosyl, 0.1$\underline{M}$ 2-mercaptoethanol. Total RNA was then isolated from this lysate by the AGPC method of P. Chomczynski and N. Sacchi described in Analytical Biochemistry, vol. 162, pp. 156–159 (1987).

Poly A$^+$ RNA was isolated by oligo dT cellulose chromatography by the method of Aviv, H. and Leder, P. (1972) Proc. Natl. Acad. Sci. (USA) 69:1408–1412 precipitated with ethanol and dissolved to a concentration of 0.36 ug/ul. One microgram to poly A$^+$ RNA was used to prepare cDNA according to Gubler, U. and Hoffman, B. J. (1983) Gene 25:263–169.

The cDNA was incorporated into a lambda gtll expression library using Eco R1 linkers from Boehringer Mannheim catalog No. 988448 or New England Bio Lab No. 1070 and instructions provided by these manufacturers.

The resulting library, which contains 10$^6$ independent clones, was screened on E. coli Y1090 rk$^-$ (Promega Biotec) with an appropriate polyclonal antibody to IL-1i as described previously using screening conditions described by R. A. Young and R. W. Davis [(1983) PNAS 80:1194–1198]. Positive signals will be detected using a biotinylated second antibody (such as goat anti-mouse IgG, Bethesda Research Labs) followed by a strepavidin-alkaline phosphatase conjugate (Bethesda Research Labs), as described by Bayer, E. A. and Wilchek, M. (1979) in Methods in Biochemical Analysis, and Guesdon, J. L. Ternynch, T. and Avrameas, S. (1979) J. Histochem. Cytochem. 27:1131–1138 and according to manufacturer's instructions.

Example 6

Preparation and Sequencing of Gene Encoding IL-1i cDNA prepared as described in Example 5 was incorporated into the cloning vector lambda GT10. This cDNA was first methylated using EcoRI methylase with S-adenosylmethionine as the substrate, EcoRI linkers were attached in a ligation reaction, and excess linkers were removed by digestion with EcoRI endonuclease and chromatography on a CL6B spin column. A ligation reaction containing 0.124 ug of Tinkered, size-selected cDNA and 1 ug of EcoRI-cut and phosphatase-treated lambda GT10 was performed, and the products of this ligation reaction were packaged using GIGAPACK GOLD packaging extracts (Stratagene). This yielded a library of 1×10$^7$ members.

In order to screen this GT10 library, oligonucleotide (antisense) probes were synthesized based on protein and peptide sequence presented in Example 3. The sequences of the probes and of their corresponding peptide sequence are as follows.

```
                   T           T           A
Probe    T T C T A C G T C C G N A A G 5'
ILlil-3 Lys   Met   Gln   Ala   Phe T     A     A     A     T     T
Probe    T T C A A G A T G A A G G T C C T C C T 5'
ILlil-4 Lys   Phe   Tyr   Phe   Gln   Glu   Asp T     A     A
Probe    T A C C A N T G N T T C A A G A T G A A 5'
ILlil-5 Met   Val   Thr   Lys   Phe   Tyr   Phe A           A     T     T
Probe    C T G C A N T T G G T C T T C T G 5'
ILlil-6 Asp   Val   Asn   Gln   Lys   Thr A     T     T                 A
Probe    T T G G T C T T C T G N A A G A T 5'
#ILlil-7 Asn   Gln   Lys   Thr   Phe   Tyr
Note:
N = A, G, C, and T
```

Probe #IL1i1-3 was $^{32}$P-phosphorylated at its 5' end and used to screen 3×10$^5$ plaques of the library. The probe hybridized reproducibly to three plaques, and out of these, one plaque was shown to also hybridize to probe #IL1il-4. This plaque, GT10-IL1i-2A, was cultivated and the DNA was isolated using Lambdasorb (Promega) according to the manufacturer's instructions. GT10-IL1i-2A has been deposited at American Type Culture Collection (ATCC) in Rockville, Md. under Accession No. 40488. The DNA was digested with EcoRI, divided into five equal aliquots, and electrophoresed on a 1% agarose gel.

Figure 12A:
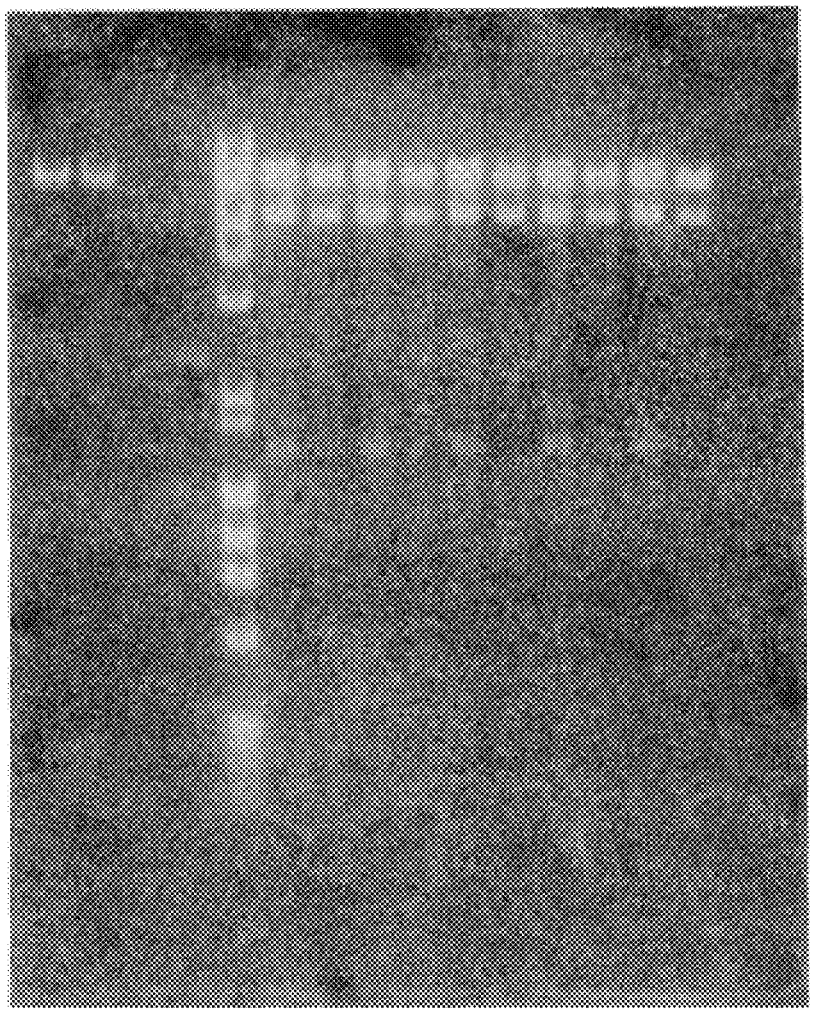
FIG. 12a is a photograph of the gel with the GT10-IL1i-2A digested with EcoRI after electrophoresis according to Example 6.

After electrophoresis, this gel was stained with ethidium bromide. A photograph of this gel is shown in FIG. 12a. Lanes 6, 8, 10, 12, and 14 contain the five aliquots from the EcoRI digestion. Lane 5 contains a mixture of wild-type lambda DNA cut with HindIII and ØX174 RF DNA cut with HaeIII (New England Biolabs) which are useful as molecular weight markers. FIG. 12a shows that GT10-IL1i-2A contains an EcoRI fragment that is 1850 base pairs in length.

In order to demonstrate more conclusively that this 1850 bp fragment carries coding sequence for the IL1 inhibitor, a Southern blot was performed as follows. The DNA fragments in the gel shown in FIG. 12a were blotted onto nitrocellulose using standard methods. The nitrocellulose was then cut lengthwise into five strips such that each strip contained the DNA from lanes 6, 8, 10, 12, and 14. The strips were then individually hybridized to each of the five oligonucleotide probes (above) which were labeled at the 5' end with $^{32}$P phosphate. The oligonucleotide concentration was 1 pmole/ml and the hybridization temperatures were as follows.

| LANE | PROBE | TEMPERATURE |
|---|---|---|
| 6 | #ILlil-3 | 35° C. |
| 8 | #ILlil-4 | 42° C. |
| 10 | #ILlil-5 | 42° C. |
| 12 | #ILlil-6 | 40° C. |
| 14 | #ILlil-7 | 35° C. |

Figure 12B:
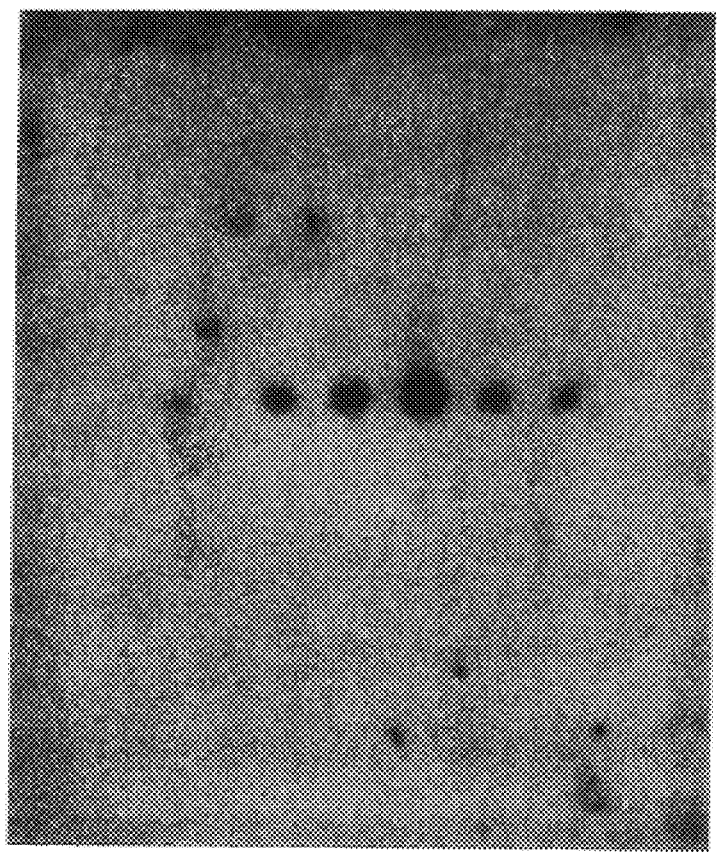

After washing, the strips were lined up and taped together to reform the original nitrocellulose sheet. This was autoradiographed in the presence of an intensifying screen at −70° C. for 24 hours. FIG. 12b is a photograph of this autoradiograph. It provides evidence that all of the probes hybridize specifically to the 1850 bp fragment, proving that this fragment carries substantial coding sequences for the IL1 inhibitor.

In order to determine its DNA sequence, GT10-IL1I-2A DNA was digested with EcoRI, electrophoresed on a 1% agarose gel, and the 1850 bp fragment was isolated. This fragment was ligated with EcoRI-digested M13 mp19 and transformed into E. coli strain JM109. Transformants were screened by looking for those lacking beta-galactosidase activity. Five such transformants were isolated, single-stranded DNA was prepares, and sequencing was performed according to Sanger et al. The DNA sequence of three of the transformants corresponded to the 3' end of the mRNA, while two transformants provided protein coding sequence. In FIG. 13, the DNA sequence is shown that was obtained for the protein coding region of the cDNA.

FIG. 13 also shows the predicted amino acid sequence. The amino acid sequence from the first amino acid Alanine to the 29th amino acid Proline and from the 79th amino acid isoleucine to the end is the hypothesized amino acid sequence. The predicted amino acid sequence from the 30th amino acid Proline to the 78th amino acid Proline agrees with the peptide sequences described in Example 3.

Example 7

Sequencing GT10-IL-1I-2A and IL-1i

A portion of GT10-IL1I-2A has been sequenced and is set forth in FIG. 14. The DNA encodes a protein containing amino acid sequences that are characteristic of IL-1i (nucleotides 99–557). However, it is believed that several modifications may be made to this protein before it is secreted into the extracellular milieu. These modifications may or may not be essential for the protein to have activity as an IL-1i.

GT10-IL1i-2A encodes at least 32 amino acids N-terminal (nucleotides 3–98) to the amino terminus of the form of IL-1i known as X. It is believed that included in these 32 amino acids is a secretory leader sequence that starts at the M encoded by nucleotides 24–26, directs the nascent IL-1i to the extracellular milieu, and is then removed by a leader peptidase, and possibly other peptidases. The extent to which this sequence is removed in forms alpha and beta of IL-1i is presently unknown, but the N-terminus of these forms is thought to be close to that of form X. Removal of the secretory leader sequence is probably required for the protein to have effective IL-1i activity.

Nucleotides 349–351 of GT10-IL1I-2A encode an N residue that is part of a concensus N-glycosylation site. On the basis of their susceptibility to digestion with N-glycanase it is believed that forms alpha and beta of IL-1i are glycosylated. Since form X is not believed to be susceptible to digestion with this enzyme it is believed that it is not glycosylated, although this remains a possibility that could easily be demonstrated by one of ordinary skill in the art of protein sequencing using the information provided here. It is believed that glycosylation at this N residue is not required for the protein to show effective IL-1i activity.

Nucleotides 99–101 of GT10-IL1i-2A encode a P (see FIG. 15), but no P has been detected at this position (the N-terminus) of form X of IL-1i. It is possible that this residue has been modified in the mature protein. It is believed that modification of this residue is not essential for effective IL-1i activity.

The presently unknown N-terminus residues of forms alpha and eta are not wholly detectable by Edman degradation and are likely to be modified following removal of some of the N-terminal residues of the protein encoded by GT10-IL1i-2A. It is believed that this modification is not essential for effective IL-1i activity.

Example 8

Expression of Genes Encoding IL-1i in Animal Cells

Figure 6:
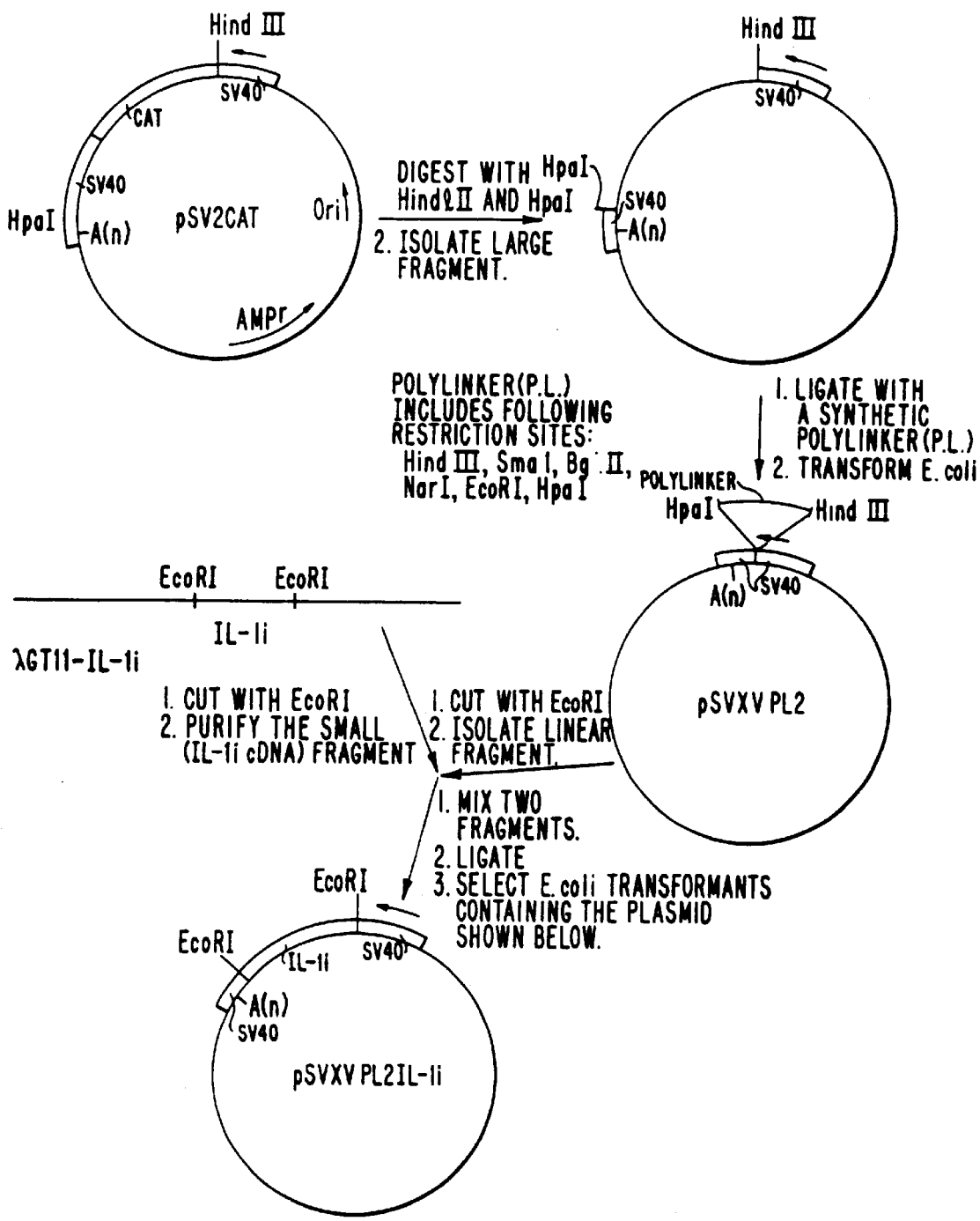
FIG. 6 depicts the construction of plasmid pSVXVPL2IL-1i.
Figure 7:
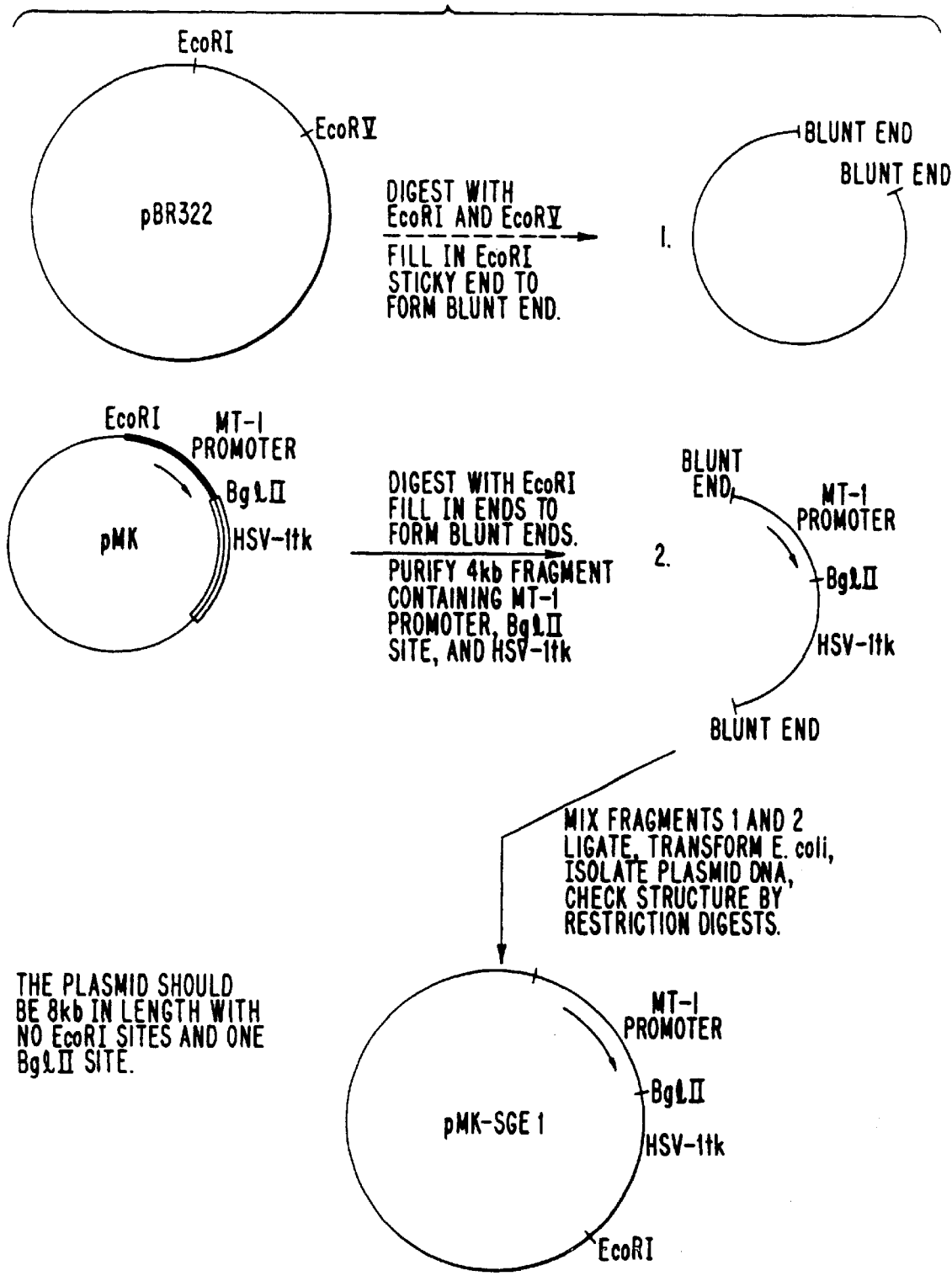
FIG. 7 depicts the construction of plasmid pMK-SGE:IL-1i.
Figure 7:
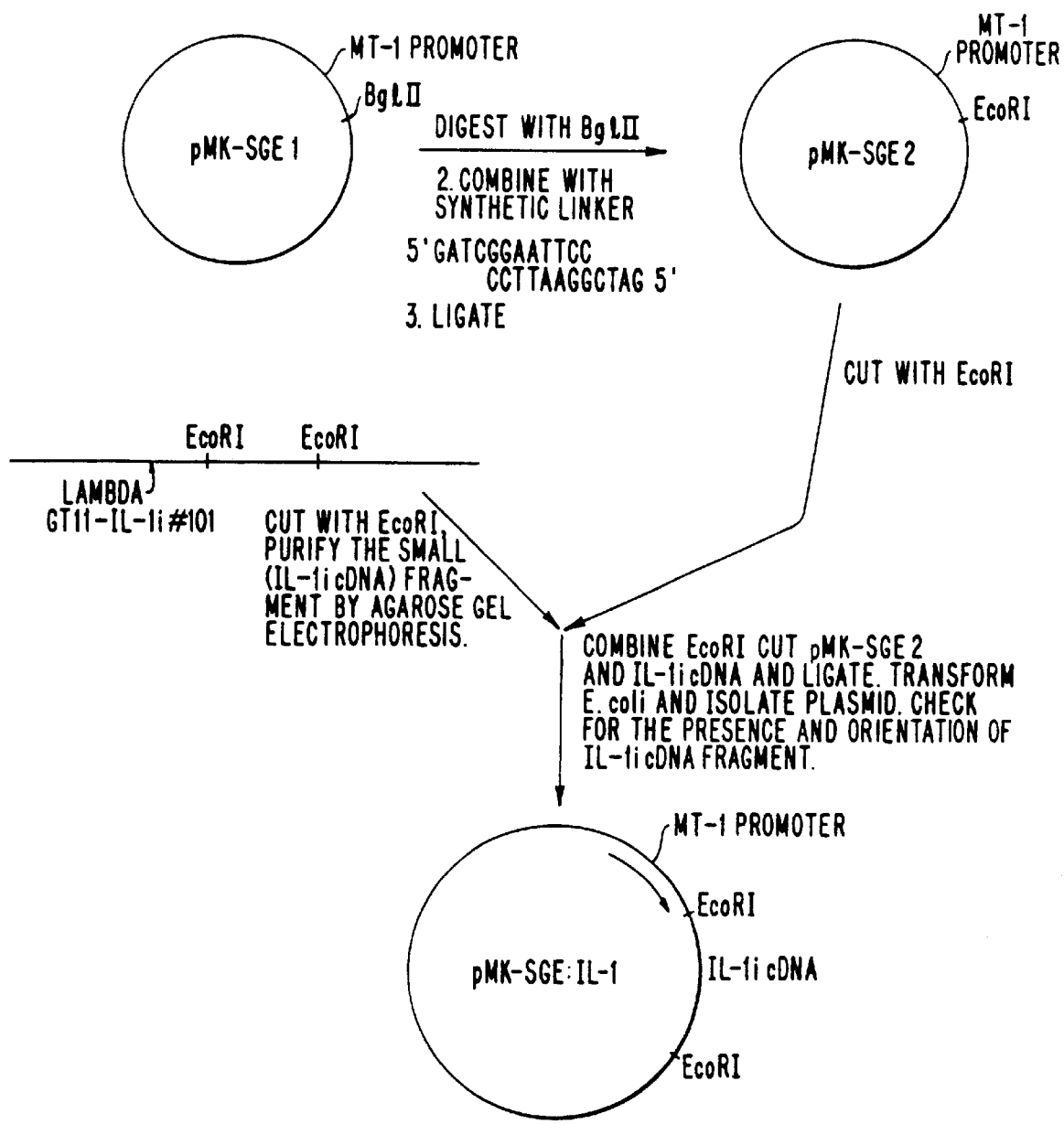

Animal-cell expression of IL-1i requires the following steps:

a. Construction of an expression vector
b. Choice of a host cell line
c. Introduction of the expression vector into host cells
d. Manipulation of recombinant host cells to increase expression levels of IL-1i 1. IL-1i expression vectors designed for use in animal cells can be of several types including strong consitutitve expression constructs, inducible gene constructs, as well as those designed for expression in particular cell types. In all cases promoters and other gene regulatory regions such as enhancers (inducible or not) and polyadenylation signals are placed in the appropriate location in relation to the cDNA sequences in plasmid-based vectors. Two examples of such constructs follow: (1) A construct using a strong constitutive promoter region should be made using the simian virus 40 (SV40) gene control signals in an arrangement such as that found in the plasmid pSV2CAT as described by Gorman et al. in Mol. Cel. Biol. 2:1044–1051,.1982, specifically incorporated herein by reference. This plasmid should be manipulated in such a way as to substitute the IL-1i cDNA for the chloramphenicol acetyltransferase (CAT) coding sequences using standard molecular biological techniques (Maniatis et al., supra), as shown in FIG. 6. (2) An inducible gene construct should be made utilizing the plasmid PMK which contains the mouse metallothionein (MT-1) promoter region (Brinster et al., Cell 27:228–231, 1981). This plasmid can be used as a starting material and should be manipulated as shown in FIG. 7 to yield a metal-inducible gene construct.

2. A number of animal cell lines should be used to express IL-1i using the vectors described above to produce active protein. Two potential cell lines that have been well-characterized for their ability to promote foreign gene expression are mouse Ltk⁻ and Chinese hamster ovary (CHO) dhfr⁻ cells, although expression of Il-1i is not limited to these cell lines.

3. Vector DNA should be introduced into these cell lines using any of a number of gene-transfer techniques. The method employed here involves the calcium phosphate-DNA precipitation technique described by S. L. Graham & A. S. van der Eb (Virology 52:456–467, 1973) in which the expression vector for IL-1i is co-precipitated with a second expression vector encoding a selectable marker. In the case of Ltk⁻ cell transfection, the selectable marker is a thymidine kinase gene and the selection is as described by Wigler, et al. (Cell 16:777–785, 1979) and in the case of CHO dhfr⁻ cells the selectable marker is dihydrofolate reductase (DHFR) whose selection is as described by Ringold et al. in J. Mol. Appl. Genet. 1:165–175, 1981.

4. Cells that express the IL-1i gene constructs should then be grown under conditions that will increase the levels of production of IL-1i. Cells carrying the metallothionein promoter constructs can now be grown in the presence of heavy metals such as cadmium which will lead to a 5-fold increased utilization of the MT-1 promoter (Mayo et al., Cell 29:99–108) subsequently leading to a comparable increase in IL-1i protein levels. Cells containing IL-1i expression vectors (either SV40- or MT-1-based) along with a DHFR expression vector can be taken through the gene amplification protocol described by Ringold et al. (J. Mol. Appl.

Genet. 1:165–175, 1981) using methotrexate, a competitive antagonist of DHFR. This leads to more copies of the DHFR genes present in the cells and, concomitantly, increased copies of the IL-1i genes which, in turn, can lead to more IL-1i protein being produced by the cells.

Example 9

Purification of Il-1i From Recombinant Animal Cells

Since the IL-1i are expected to be secreted from cells like the natural material, it is anticipated that the methods described above for purification of the natural protein will allow similar purification and characterization of the recombinant protein.

Example 10

Sequence of IL-1i

The amino terminal residue of IL-1i has been identified several times by direct protein sequencing as an arginine (R). The result of such sequencing is shown in Example 3. In contrast, the amino terminal residue of IL-1i predicted by the sequence of the cDNA is a proline (P). This amino terminal residue corresponds to nucleotides 85–87 in FIG. 13, and is circled in FIGS. 14 and 15. This apparent disagreement between the cDNA sequence and the direct protein sequence can be resolved by assuming that an error in the cDNA sequence was incorporated during the reverse transcriptase-catalyzed synthesis from its mRNA. That is, a CGA (arginine) codon, located on the mRNA where it would code for that amino terminal residue, could have been changed during the reverse-transcriptase reaction to a CCA (proline) codon in the cDNA. This type of reverse transcriptase problem has been reported in the literature before, e.g., by B. D. Clark et al. in Nucleic Acids Research 14:7897 (1986).

The present inventors believe that the correct amino acid sequence of the protein is as predicted by the cDNA except that the amino terminal amino acid is an arginine instead of the proline residue indicated in FIGS. 13–15. The inventors contemplate that both DNA sequences and their corresponding peptide sequences fall within the scope of their invention although the amino terminal arginine sequence is preferred.

What is claimed is:

1. An interleukin-1 inhibitor (IL-1i), comprising a glycosylated or nonglycosylated polypeptide having interleukin-1 (IL-1) inhibitory activity and being free of other human protein, wherein said polypeptide is selected from the group consisting of:

A) a polypeptide comprising all or an IL-1 inhibitory fragment of the amino acid sequence:

(U) (X) P S G R K S S K M Q A F R I W D V N Q K T

F Y L R N N Q L V A G Y L Q G P N V N L E E K I D

V V P I E P H A L F L G I H G G K M C L S C V K S

G D E T R L Q L E A V N I T D L S E N R K Q D K R

F A F I R S D S G P T T S F E S A A C P G W F L C

T A M E A D Q P V S L T N M P D E G V M V T K F Y

F Q E D E wherein (U) is M or nothing and (X) is R or P; and

B) a polypeptide that is at least about 90% homologous to the amino acid sequence set forth in A).

2. The IL-1i of claim 1, wherein the amino acid sequence of said polypeptide is at least about 95% homologous to the following amino acid sequence:

(U) (X) P S G R K S S K M Q A F R I W D V N Q K T

F Y L R N N Q L V A G Y L Q G P N V N L E E K I D

V V P I E P H A L F L G I H G G K M C L S C V K S

G D E T R L Q L E A V N I T D L S E N R K Q D K R

F A F I R S D S G P T T S F E S A A C P G W F L C

T A M E A D Q P V S L T N M P D E G V M V T K F Y

F Q E D E wherein (U) is M or nothing and (X) is R.

3. A pharmaceutical composition comprising, in a pharmaceutically acceptable preparation, a therapeutically effective amount of the IL-1i of claim 2.

4. A method of treating a patient having arthritis comprising administering to the patient a therapeutically effective amount of an IL-1 inhibitor according to claim 2.

5. A method of treating a patient having rheumatoid arthritis comprising administering to the patient a therapeutically effective amount of an IL-1 inhibitor according to claim 2.

6. A method of treating a patient having osteoarthritis comprising administering to the patient a therapeutically effective amount of an IL-1 inhibitor according to claim 2.

7. A method of treating a patient to reduce an adverse effect of IL-1 comprising administering to the patient a therapeutically effective amount of an IL-1 inhibitor according to claim 2.

8. A method of treating a patient having at least one of the following:

Crohn's disease, ulcerative colitis, glomerulonephritis, or leukemia, comprising administering to the patient a therapeutically effective amount of an IL-1 inhibitor according to claim 2.

9. The IL-1i of claim 1, wherein the amino acid sequence of said polypeptide is at least about 90% homologous to the following amino acid sequence:

(U) (X) P S G R K S S K M Q A F R I W D V N Q K T

F Y L R N N Q L V A G Y L Q G P N V N L E E K I D

V V P I E P H A L F L G I H G G K M C L S C V K S

G D E T R L Q L E A V N I T D L S E N R K Q D K R

F A F I R S D S G P T T S F E S A A C P G W F L C

T A M E A D Q P V S L T N M P D E G V M V T K F Y

F Q E D E wherein (U) is M or nothing and (X) is R.

10. A pharmaceutical composition comprising, in a pharmaceutically acceptable preparation, a therapeutically effective amount of the IL-1i of claim 9.

11. A method of treating a patient having arthritis comprising administering to the patient a therapeutically effective amount of an IL-1 inhibitor according to claim 9.

12. A method of treating a patient having rheumatoid arthritis comprising administering to the patient a therapeutically effective amount of an IL-1 inhibitor according to claim 9.

13. A method of treating a patient having osteoarthritis comprising administering to the patient a therapeutically effective amount of an IL-1 inhibitor according to claim 9.

14. A method of treating a patient to reduce an adverse effect of IL-1 comprising administering to the patient a therapeutically effective amount of an IL-1 inhibitor according to claim 9.

15. A method of treating a patient having at least one of the following:

Crohn's disease, ulcerative colitis, glomerulonephritis, or leukemia, comprising administering to the patient a therapeutically effective amount of an IL-1 inhibitor according to claim 9.

16. The IL-1i of claim 9, wherein the IL-1i is recombinantly made by a host cell not capable of glycosylation or a non-human host cell.

17. The IL-1i of claim 16, wherein said host cell is selected from a yeast cell, a mouse Ltk⁻ cell, and a Chinese hamster ovary cell.

18. The IL-1i of claim 16, wherein said host cell is a prokaryotic cell.

19. The IL-1i of claim wherein said host cell is $E.\ coli$.

20. The IL-1i of claim 16, wherein said host cell is a eukaryotic cell.

21. The IL-1i of claim 20, wherein said host cell is a mammalian cell.

22. The IL-1i of claim 20, wherein said host cell is a Chinese hamster ovary cell.

23. The IL-1i of claim 9, wherein said IL-1i is glycosylated.

24. A pharmaceutical composition comprising, in a pharmaceutically acceptable preparation, a therapeutically effective amount of the IL-1i of claim 23.

25. The IL-1i of claim 9, wherein said IL-1i is nonglycosylated.

26. A pharmaceutical composition comprising, in a pharmaceutically acceptable preparation, a therapeutically effective amount of the IL-1i of claim 25.

27. The IL-1i of claim 9, wherein (U) is nothing.

28. The IL-1i of claim 9, wherein (U) is M.

29. The IL-1i of claim 1, wherein said IL-1i is a polypeptide comprising all or an IL-1 inhibitory fragment of the amino acid sequence:

```
(U) (X) P S G R K S S K M Q A F R I W D V N Q K T
F Y L R N N Q L V A G Y L Q G P N V N L E E K I D
V V P I E P H A L F L G I H G G K M C L S C V K S
G D E T R L Q L E A V N I T D L S E N R K Q D K R
F A F I R S D S G P T T S F E S A A C P G W F L C
T A M E A D Q P V S L T N M P D E G V M V T K F Y
F Q E D E
``` wherein (U) is M or nothing and (X) is R or P.

30. The IL-1i of claim 21, wherein (X) is R.

31. A pharmaceutical composition comprising, in a pharmaceutically acceptable preparation, a therapeutically effective amount of the IL-1i of claim 30.

32. The IL-1i of claim 30, wherein said polypeptide inhibits IL-1 induced PGE$_2$ production.

33. The IL-1i of claim 29, which comprises the following amino acid sequence:

```
(U) (X) P S G R K S S K M Q A F R I W D V N Q K T
F Y L R N N Q L V A G Y L Q G P N V N L E E K I D
V V P I E P H A L F L G I H G G K M C L S C V K S
G D E T R L Q L E A V N I T D L S E N R K Q D K R
F A F I R S D S G P T T S F E S A A C P G W F L C
T A M E A D Q P V S L T N M P D E G V M V T K F Y
F Q E D E
``` wherein (U) is M or nothing and (X) is R or P.

34. The IL-1i of claim 33, wherein (X) is R.

35. A pharmaceutical composition comprising, in a pharmaceutically acceptable preparation, a therapeutically effective amount of the IL-1i of claim 30.

36. A method of treating a patient having arthritis comprising administering to the patient a therapeutically effective amount of an IL-1 inhibitor according to claim 34.

37. A method of treating a patient having rheumatoid arthritis comprising administering to the patient a therapeutically effective amount of an IL-1 inhibitor according to claim 34.

38. A method of treating a patient having osteoarthritis comprising administering to the patient a therapeutically effective amount of an IL-1 inhibitor according to claim 34.

39. A method of treating a patient to reduce an adverse effect of IL-1 comprising administering to the patient a therapeutically effective amount of an IL-1 inhibitor according to claim 34.

40. A method of treating a patient having at least one of the following:

Crohn's disease, ulcerative colitis, glomerulonephritis, or leukemia, comprising administering to the patient a therapeutically effective amount of an IL-1 inhibitor according to claim 34.

41. The IL-1i of claim 34, wherein (U) is M.

42. A pharmaceutical composition comprising, in a pharmaceutically acceptable preparation. a therapeutically effective amount of the IL-1i of claim 41.

43. The IL-1i of claim 34, wherein (U) is nothing.

44. A pharmaceutical composition comprising, in a pharmaceutically acceptable preparation, a therapeutically effective amount of the IL-1i of claim 43.

45. The IL-1i of claim 34, wherein the IL-1i is recombinantly made by a host cell not capable of glycosylation or a non-human host cell.

46. The IL-1i of claim 45, wherein said host cell is selected from a yeast cell, a mouse Ltk⁻ cell, and a Chinese hamster ovary cell.

47. A pharmaceutical composition comprising, in a pharmaceutically acceptable preparation a therapeutically effective amount of the IL-1i of claim 46.

48. The IL-1i of claim 46, wherein said host cell is a mouse Ltk⁻ cell.

49. The IL-1i of claim 45, wherein said host cell is a prokaryotic cell.

50. A pharmaceutical composition comprising, in a pharmaceutically acceptable preparation, a therapeutically effective amount of the IL-1i of claim 49.

51. The IL-1i of claim 49, wherein said host cell is $E.\ coli$.

52. A pharmaceutical composition comprising, in a pharmaceutically acceptable preparation, a therapeutically, effective amount of the IL-1i of claim 51.

53. The IL-1i of claim 45, wherein said host cell is a eukaryotic cell.

54. A pharmaceutical composition comprising, in a pharmaceutically acceptable preparation, a therapeutically effective amount of the IL-1i of claim 53.

55. The IL-1i of claim 53, wherein said host cell is a mammalian cell.

56. A pharmaceutical composition comprising, in a pharmaceutically acceptable preparation, a therapeutically effective amount of the IL-1i of claim 55.

57. The IL-1i of claim 53, wherein said host cell is a Chinese hamster ovary cell.

58. A pharmaceutical composition comprising, in a pharmaceutically acceptable preparation, a therapeutically effective amount of the IL-1i of claim 57.

59. The IL-1i of claim 34 having a purity of at least about 90%.

60. A pharmaceutical composition comprising, in a pharmaceutically acceptable preparation, a therapeutically effective amount of the IL-1i of claim 59.

61. The IL-1i of claim 34 having a purity of at least about 95%.

62. A pharmaceutical composition comprising, in a pharmaceutically acceptable preparation, a therapeutically effective amount of the IL-1i of claim 61.

63. The IL-1i of claim 34, wherein said IL-1i is glycosylated.

64. A pharmaceutical composition comprising, in a pharmaceutically acceptable preparation, a therapeutically effective amount of the IL-1i of claim 63.

65. The IL-1i of claim 34, wherein said IL-1i is nonglycosylated.

66. A pharmaceutical composition comprising, in a pharmaceutically acceptable preparation, a therapeutically effective amount of the IL-1i of claim 65.

67. The pharmaceutical composition of any of claims 42 or 64, further comprising a collagenase inhibitor.

68. The IL-1i of claim 34, wherein said IL-1i is derived from a host cell comprising a recombinant DNA molecule comprising a sequence encoding said IL-1i.

69. The IL-1i of claim 68, further comprising an N-terminal secretion leader sequence.

70. The IL-1i of claim 69, wherein the leader sequence comprises all or part of the following amino acid sequence:

MEICRGLRSHLITLLLFLFHSETIC.

71. The IL-1i of claim 34, which consists of the following amino acid sequence, (U) R P S G R K S S K M Q A F R I W D V N Q K T F
Y L R N N Q L V A G Y L Q G P N V N L E E K I D V
V P I E P H A L F L G I H G G K M C L S C V K S G
D E T R L Q L E A V N I T D L S E N R K Q D K R F
A F I R S D S G P T T S F E S A A C P G W F L C T
A M E A D Q P V S L T N M P D E G V M V T K F Y F
Q E D E wherein (u) is M or nothing.

72. A pharmaceutical composition comprising, in a pharmaceutically acceptable preparation, a therapeutically effective amount of the IL-1i of claim 71.

73. A method of treating a patient having arthritis comprising administering to the patient a therapeutically effective amount of an IL-1 inhibitor according to claim 71.

74. A method of treating a patient having rheumatoid arthritis comprising administering to the patient a therapeutically effective amount of an IL-1 inhibitor according to claim 71.

75. A method of treating a patient having osteoarthritis comprising administering to the patient a therapeutically effective amount of an IL-1 inhibitor according to claim 71.

76. A method of treating a patient to reduce an adverse effect of IL-1 comprising administering to the patient a therapeutically effective amount of an IL-1 inhibitor according to claim 71.

77. A method of treating a patient having at least one of the following:

Crohn's disease, ulcerative colitis, glomerulonephritis, or leukemia, comprising administering to the patient a therapeutically effective amount of an IL-1 inhibitor according to claim 71.

78. The IL-1i of claim 71, wherein (U) is M.

79. A pharmaceutical composition comprising, in a pharmaceutically acceptable preparation, a therapeutically effective amount of the IL-1i of claim 78.

80. A method of treating a patient having arthritis comprising administering to the patient a therapeutically effective amount of an IL-1 inhibitor according to claim 78.

81. A method of treating a patient having rheumatoid arthritis comprising administering to the patient a therapeutically effective amount of an IL-1 inhibitor according to claim 78.

82. A method of treating a patient having osteoarthritis comprising administering to the patient a therapeutically effective amount of an IL-1 inhibitor according to claim 78.

83. A method of treating a patient to reduce an adverse effect of IL-1 comprising administering to the patient a therapeutically effective amount of an IL-1 inhibitor according to claim 78.

84. A method of treating a patient having at least one of the following:

Crohn's disease, ulcerative colitis, glomerulonephritis, or leukemia, comprising administering to the patient a therapeutically effective amount of an IL-1 inhibitor according to claim 76.

85. The IL-1i of claim 78, wherein said IL-1i is nonglycosylated.

86. A pharmaceutical composition comprising, in a pharmaceutically acceptable preparation, a therapeutically effective amount of the IL-1i of claim 85.

87. A method of treating a patient having arthritis comprising administering to the patient a therapeutically effective amount of an IL-1 inhibitor according to claim 85.

88. A method of treating a patient having rheumatoid arthritis comprising administering to the patient a therapeutically effective amount of an IL-1 inhibitor according to claim 85.

89. A method of treating a patient having osteoarthritis comprising administering to the patient a therapeutically effective amount of an IL-1 inhibitor according to claim 85.

90. A method of treating a patient to reduce an adverse effect of IL-1 comprising administering to the patient a therapeutically effective amount of an IL-1 inhibitor according to claim 85.

91. A method of treating a patient having at least one of the following:

Crohn's disease, ulcerative colitis, glomerulonephritis, or leukemia, comprising administering to the patient a therapeutically effective amount of an IL-1 inhibitor according to claim 85.

92. The IL-1i of claim 85, wherein the IL-1i is recombinantly made by an *E. coli* host cell.

93. A pharmaceutical composition comprising, in a pharmaceutically acceptable preparation, a therapeutically effective amount of the IL-1i of claim 92.

94. A method of treating a patient having arthritis comprising administering to the patient a therapeutically effective amount of an IL-1 inhibitor according to claim 92.

95. A method of treating a patient having rheumatoid arthritis comprising administering to the patient a therapeutically effective amount of an IL-1 inhibitor according to claim 92.

96. A method of treating a patient having osteoarthritis comprising administering to the patient a therapeutically effective amount of an IL-1 inhibitor according to claim 92.

97. A method of treating a patient to reduce an adverse effect of IL-1 comprising administering to the patient a therapeutically effective amount of an IL-1 inhibitor according to claim 92.

98. A method of treating a patient having at least one of the following:
Crohn's disease, ulcerative colitus, glomerulonephritis, or leukemia,
comprising administering to the patient a therapeutically effective amount of an IL-1 inhibitor according to claim 92.

99. The IL-1i of claim 92 having a purity of at least about 90%.

100. A pharmaceutical composition comprising, in a pharmaceutically acceptable preparation, a therapeutically effective amount of the IL-1i of claim 99.

101. A method of treating a patient having arthritis comprising administering to the patient a therapeutically effective amount of an IL-1 inhibitor according to claim 99.

102. A method of treating a patient having rheumatoid arthritis comprising administering to the patient a therapeutically effective amount of an IL-1 inhibitor according to claim 99.

103. A method of treating a patient having osteoarthritis comprising administering to the patient a therapeutically effective amount of an IL-1 inhibitor according to claim 99.

104. A method of treating a patient to reduce an adverse effect of IL-1 comprising administering to the patient a therapeutically effective amount of an IL-1 inhibitor according to claim 99.

105. A method of treating a patient having at least one of the following:
Crohn's disease, ulcerative colitus, glomerulonephritis, or leukemia,
comprising administering to the patient a therapeutically effective amount of an IL-1 inhibitor according to claim 99.

106. The IL-1i of claim 92 having a purity of at least about 95%.

107. A pharmaceutical composition comprising, in a pharmaceutically acceptable preparation, a therapeutically effective amount of the IL-1i of claim 106.

108. A method of treating a patient having arthritis comprising administering to the patient a therapeutically effective amount of an IL-1 inhibitor according to claim 106.

109. A method of treating a patient having rheumatoid arthritis comprising administering to the patient a therapeutically effective amount of an IL-1 inhibitor according to claim 106.

110. A method of treating a patient having osteoarthritis comprising administering to the patient a therapeutically effective amount of an IL-1 inhibitor according to claim 106.

111. A method of treating a patient to reduce an adverse effect of IL-1 comprising administering to the patient a therapeutically effective amount of an IL-1 inhibitor according to claim 106.

112. A method of treating a patient having at least one of the following:
Crohn's disease, ulcerative colitus, glomerulonephritis, or leukemia,
comprising administering to the patient a therapeutically effective amount of an IL-1 inhibitor according to claim 106.

113. The IL-1i of claim 71 wherein the IL-1i is recombinantly made by a Chinese hamster ovary host cell.

114. The IL-1i of claim 71 having a purity of at least about 90%.

115. A pharmaceutical composition comprising, in a pharmaceutically acceptable preparation, a therapeutically effective amount of the IL-1i of claim 114.

116. A method of treating a patient having arthritis comprising administering to the patient a therapeutically effective amount of an IL-1 inhibitor according to claim 114.

117. A method of treating a patient having rheumatoid arthritis comprising administering to the patient a therapeutically effective amount of an IL-1 inhibitor according to claim 114.

118. A method of treating a patient having osteoarthritis comprising administering to the patent a therapeutically effective amount of an IL-1 inhibitor according to claim 114.

119. A method of treating a patient to reduce an adverse effect of IL-1 comprising administering to the patient a therapeutically effective amount of an IL-1 inhibitor according to claim 114.

120. A method of treating a patient having at least one of the following:
Crohn's disease, ulcerative colitus, glomerulonephritis, or leukemia,
comprising administering to the patient a therapeutically effective amount of an IL-1 inhibitor according to claim 114.

121. The IL-1i of claim 114, wherein said IL-1i is glycosylated.

122. A pharmaceutical composition comprising, in a pharmaceutically acceptable preparation, a therapeutically effective amount of the IL-1i of claim 121.

123. A method of treating a patient having arthritis comprising administering to the patient a therapeutically effective amount of an IL-1 inhibitor according to claim 121.

124. A method of treating a patient having rheumatoid arthritis comprising administering to the patient a therapeutically effective amount of an IL-1 inhibitor according to claim 121.

125. A method of treating a patient having osteoarthritis comprising administering to the patient a therapeutically effective amount of an IL-1 inhibitor according to claim 121.

126. A method of treating a patient to reduce an adverse effect of IL-1 comprising administering to the patient a therapeutically effective amount of an IL-1 inhibitor according to claim 121.

127. A method of treating a patient having at least one of the following:
Crohn's disease, ulcerative coitus, glomerulonephritis, or leukemia,
comprising administering to the patient a therapeutically effective amount of an IL-1 inhibitor according to claim 121.

128. The IL-1i of claim 71 having a purity of at least about 95%.

129. A pharmaceutical composition comprising, in a pharmaceutically acceptable preparation, a therapeutically effective amount of the IL-1i of claim 128.

130. A method of treating a patient having arthritis comprising administering to the patent a therapeutically effective amount of an IL-1 inhibitor according to claim 128.

131. A method of treating a patient having rheumatoid arthritis comprising administering to the patient a therapeutically effective amount of an IL-1 inhibitor according to claim 128.

132. A method of treating a patient having osteoarthritis comprising administering to the patient a therapeutically effective amount of an IL-1 inhibitor according to claim 128.

133. A method of treating a patient to reduce an adverse effect of IL-1 comprising administering toe patient a therapeutically effective amount of an IL-1 inhibitor according to claim 128.

134. A method of treating a patient having at least one of the following:
Crohn's disease, ulcerative colitis, glomerulonephritis, or leukemia,
comprising administering to the patient a therapeutically effective amount of an IL-1 inhibitor according to claim 128.

135. The IL-1i of claim 71, wherein the IL-1i is recombinantly made by a eukaryotic host cell.

136. The IL-1i of claim 128, wherein said IL-1i is glycosylated.

137. A pharmaceutical composition comprising, in a pharmaceutically acceptable preparation, a therapeutically effective amount of the IL-1i of claim 136.

138. A method of treating a patient having arthritis comprising administering to the patient a therapeutically effective amount of an IL-1 inhibitor according to claim 136.

139. A method of treating a patient having rheumatoid arthritis comprising administering to the patient a therapeutically effective amount of an IL-1 inhibitor according to claim 136.

140. A method of treating a patient having osteoarthritis comprising administering to the patient a therapeutically effective amount of an IL-1 inhibitor according to claim 136.

141. A method of treating a patient to reduce an adverse effect of IL-1 comprising administering to the patient a therapeutically effective amount of an IL-1 inhibitor according to claim 136.

142. A method of treating a patient having at least one of the following:
Crohn's disease, ulcerative colitis, glomerulonephritis, or leukemia,
comprising administering to the patient a therapeutically effective amount of an IL-1 inhibitor according to claim 136.

143. The IL-1i of claim 128, wherein the IL-1i is recombinantly made by a mammalian host cell.

144. A pharmaceutical composition comprising, in a pharmaceutically acceptable preparation, a therapeutically effective amount of the IL-1i of claim 143.

145. The IL-1i of claim 128, wherein the IL-1i is recombinantly made by a prokaryotic host cell.

146. An interleukin-1 inhibitor (IL-1i), comprising a glycosylated or nonglycosylated polypeptide having interleukin-1 (IL-1) inhibitory activity, wherein said polypeptide is produced by a non-human host cell comprising a recombinant DNA molecule comprising a sequence encoding said polypeptide, and wherein said polypeptide is selected from the group consisting of:

A) a polypeptide comprising all or an IL-1 inhibitory fragment of the amino acid sequence:

(U) (X) P S G R K S S K M Q A F R I W D V N Q K T
F Y L R N N Q L V A G Y L Q G P N V N L E E K I D
V V P I E P H A L F L G I H G G K M C L S C V K S
G D E T R L Q L E A V N I T D L S E N R K Q D K R
F A F I R S D S G P T T S F E S A A C P G W F L C
T A M E A D Q P V S L T N M P D E G V M V T K F Y
F Q E D E wherein (U) is M or nothing and (X) is R or P; and B) a polypeptide that is at least about 90% homologous to the amino acid. sequence set forth in A).

147. The IL-1i of claim 146 wherein said polypeptide comprises an N-terminal amino acid sequence as follows:

(U)(X)PSGRKSSKMQAFRIWDVNQ wherein (U) is M or nothing and (X) is R or P.

148. The IL-1i of claim 146 wherein said polypeptide comprises the following amino acid sequence:

(U)(X)PSGRKSSKMQAFR wherein (U) is M or nothing and (X) is R or P.

149. The IL-1i of claim 146 wherein said polypeptide comprises the following amino acid sequence:

DVNQKTFYLRNNQLVAG

YLQGPNVNLEEKIDVVP.

150. The IL-1i of claim 146 wherein said polypeptide comprises the following amino acid sequence:

DVNQKTFYLRNNQLVAGYLQGPNVNL.

151. The IL-1i of claim 146 wherein said polypeptide comprises the following amino acid sequence:

YLRNNQLVAGYLQGPNVNLEEKIDVVP.

152. The IL-1i of claim 146 wherein said polypeptide comprises the following amino acid sequence

DFGVMVTKFYFQED.

153. The IL-1i of claim 146 wherein said polypeptide comprises the following amino acid sequence:

DEGVMVTKFYFQ.

154. The IL-1i of claim 146, wherein the amino acid sequence of said polypeptide is at least about 95% homologous to the following amino acid sequence:

(U) (X) P S G R K S S K M Q A F R I W D V N Q K T
F Y L R N N Q L V A G Y L Q G P N V N L E E K I D

-continued

```
V V P I E P H A L F L G I H G G K M C L S C V K S

G D E T R L Q L E A V N I T D L S E N R K Q D K R

F A F I R S D S G P T T S F E S A A C P G W F L C

T A M E A D Q P V S L T N M P D E G V M V T K F Y

F Q E D E
``` wherein (U) is M or nothing and (X) is R.

155. A pharmaceutical composition comprising, in a pharmaceutically acceptable preparation, a therapeutically effective amount of the IL-1i of claim 154.

156. A method of treating a patient having arthritis comprising administering to the patient a therapeutically effective amount of an IL-1 inhibitor according to claim 154.

157. A method of treating a patient having rheumatoid arthritis comprising administering to the patient a therapeutically effective amount of an IL-1 inhibitor according to claim 154.

158. A method of treating a patient having osteoarthritis comprising administering to the patient a therapeutically effective amount of an IL-1 inhibitor according to claim 154.

159. A method of treating a patient to reduce an adverse effect of IL-1 comprising administering to the patient a therapeutically effective amount of an IL-1 inhibitor according to claim 154.

160. A method of treating a patient having at least one of the following:
Crohn's disease, ulcerative colitis, glomerulonephritis, or leukemia,
comprising administering to the patient a therapeutically effective amount of an IL-1 inhibitor according to claim 154.

161. The IL-1i of claim 146, wherein the amino acid sequence of said polypeptide is at least about 90% homologous to the following amino acid sequence:

```
(U) (X) P S G R K S S K M Q A F R I W D V N Q K T

F Y L R N N Q L V A G Y L Q G P N V N L E E K I D

V V P I E P H A L F L G I H G G K M C L S C V K S

G D E T R L Q L E A V N I T D L S E N R K Q D K R

F A F I R S D S G P T T S F E S A A C P G W F L C

T A M E A D Q P V S L T N M P D E G V M V T K F Y

F Q E D E
``` wherein (U) is M or nothing and (X) is R.

162. A pharmaceutical composition comprising, in a pharmaceutically acceptable preparation, a therapeutically effective amount of the IL-1i of claim 161.

163. A method of treating a patient having arthritis comprising administering to the patient a therapeutically effective amount of an IL-1 inhibitor according to claim 161.

164. A method of treating a patient having rheumatoid arthritis comprising administering to the patient a therapeutically effective amount of an IL-1 inhibitor according to claim 161.

165. A method of treating a patient having osteoarthritis comprising administering to the patient a therapeutically effective amount of an IL-1 inhibitor according to claim 161.

166. A method of treating a patient to reduce an adverse effect of IL-1 comprising administering to the patient a therapeutically effective amount of an IL-1 inhibitor according to claim 161.

167. A method of treating a patient having at least one of the
Crohn's disease, ulcerative colitis, glomerulonephritis, or leukemia,
comprising administering to the patient a therapeutically effective amount of an IL-1 inhibitor according to claim 161.

168. The IL-1i of claim 161, wherein said host cell is selected from a yeast cell, a mouse Ltk⁻ cell, and a Chinese hamster ovary cell.

169. The IL-1i of claim 161, wherein said host cell is a prokaryotic cell.

170. The IL-1i of claim 169, wherein said host cell is *E. coli*.

171. The IL1i of claim 161, wherein said host cell is a eukaryotic cell.

172. The IL-1i of claim 171, wherein said host cell is a mammalian cell.

173. The IL-1i of claim 174, wherein said host cell is a Chinese hamster ovary cell.

174. The IL-1i of claim 161, wherein said IL-1i is glycosylated.

175. A pharmaceutical composition comprising, in a pharmaceutically acceptable preparation, a therapeutically effective amount of the IL-1i of claim 174.

176. The IL-1i of claim 161, wherein said IL-1i is nonglycosylated.

177. A pharmaceutical composition comprising, in a pharmaceutically acceptable preparation, a therapeutically effective amount of the IL-1i of claim 176.

178. The IL-1i of claim 161, wherein (U) is nothing.

179. The IL-1i of claim 161, wherein (U) is M.

180. The IL-1i of claim 161, further comprising an N-terminal secretion leader sequence.

181. The IL-1i of claim 180, wherein the leader sequence comprises all or part of the following amino acid sequence:

MEICRGLRSHLITLLLFLFHSETIC.

182. The IL-1i of claim 146, wherein said IL-1i is a polypeptide comprising all or an IL-1 inhibitory fragment of the amino acid sequence:

```
(U) (X) P S G R K S S K M Q A F R I W D V N Q K T

F Y L R N N Q L V A G Y L Q G P N V N L E E K I D

V V P I E P H A L F L G I H G G K M C L S C V K S

G D E T R L Q L E A V N I T D L S E N R K Q D K R

F A F I R S D S G P T T S F E S A A C P G W F L C

T A M E A D Q P V S L T N M P D E G V M V T K F Y

F Q E D E
``` wherein (U) is M or nothing and (X) is R or P.

183. The IL-1i of claim 183, wherein (X) is R.

184. A pharmaceutical composition comprising, in a pharmaceutically acceptable preparation, a therapeutically effective amount of the IL-1i of claim 183.

185. The IL-1i of claim 183, wherein said polypeptide inhibits IL-1 induced PGE$_2$ production.

186. The IL-1i of claim 182, which comprises the following amino acid sequence:

(U) (X) P S G R K S S K M Q A F R I W D V N Q K T
F Y L R N N Q L V A G Y L Q G P N V N L E E K I D
V V P I E P H A L F L G I H G G K M C L S C V K S
G D E T R L Q L E A V N I T D L S E N R K Q D K R
F A F I R S D S G P T T S F E S A A C P G W F L C
T A M E A D Q P V S L T N M P D E G V M V T K F Y
F Q E D E wherein (U) is M or nothing and (X) is R or P.

187. The IL-1i of claim 186, wherein (X) is R.

188. A pharmaceutical composition comprising, in a pharmaceutically acceptable preparation, a therapeutically effective amount of the IL-1i of claim 187.

189. A method of treating a patient having arthritis comprising administering to the patient a therapeutically effective amount of an IL-1 inhibitor according to claim 187.

190. A method of treating a patient having rheumatoid arthritis comprising administering to the patient a therapeutically effective amount of an IL-1 inhibitor according to claim 187.

191. A method of treating a patient having osteoarthritis comprising administering to the patient a therapeutically effective amount of an IL-1 inhibitor according to claim 187.

192. A method of treating a patient to reduce an adverse effect of IL1 comprising administering to the patient a therapeutically effective amount of an IL-1 inhibitor according to claim 187.

193. A method of treating a patient having at least one of the following:
Crohn's disease, ulcerative colitis, glomerulonephritis, or leukemia,
comprising administering to the patient a therapeutically effective amount of an IL-1 inhibitor according to claim 187.

194. The IL-1i of claim 187, wherein (U) is M.

195. A pharmaceutical composition comprising, in a pharmaceutically acceptable preparation, a therapeutically effective amount of the IL-1i of claim 194.

196. The IL-1i of claim 187, wherein (U) is nothing.

197. A pharmaceutical composition comprising, in a pharmaceutically acceptable preparation, a therapeutically effective amount of the IL-1i of claim 196.

198. The IL-1i of claim 187, wherein said host cell is selected from a yeast cell, a mouse Ltk⁻ cell, and a Chinese hamster ovary cell.

199. A pharmaceutical composition comprising, in a pharmaceutically acceptable preparation, a therapeutically effective amount of the IL-1i of claim 198.

200. The IL-1i of claim 198, wherein said host cell is a mouse Ltk⁻ cell.

201. The IL-1i of claim 187, wherein said host cell is a prokaryotic cell.

202. A pharmaceutical composition comprising, in a pharmaceutically acceptable preparation, a therapeutically effective amount of the IL-1i of claim 201.

203. The IL-1i of claim 201, wherein said host cell is *E. coli*.

204. A pharmaceutical composition comprising, in a pharmaceutically acceptable preparation, a therapeutically effective amount of the IL-1i of claim 203.

205. The IL-1i of claim 187, wherein said host cell is a eukaryotic cell.

206. A pharmaceutical composition comprising, in a pharmaceutically acceptable preparation, a therapeutically effective amount of the IL-1i of claim 205.

207. The IL-1i of claim 205, wherein said host cell is a mammalian cell.

208. A pharmaceutical composition comprising, in a pharmaceutically acceptable preparation, a therapeutically effective amount of the IL-1i of claim 207.

209. The IL-1i of claim 205, wherein said host cell is a Chinese hamster ovary cell.

210. A pharmaceutical composition comprising, in a pharmaceutically acceptable preparation, a therapeutically effective amount of the IL-1i of claim 209.

211. The IL-1i of claim 187 having a purity of at least about 90%.

212. A pharmaceutical composition comprising, in a pharmaceutically acceptable preparation. a therapeutically effective amount of the IL-1i of claim 211.

213. The IL-1i of claim 187 having a purity of at least about 95%.

214. A pharmaceutical composition comprising, in a pharmaceutically acceptable preparation, a therapeutically effective amount of the IL-1i of claim 213.

215. The pharmaceutical composition of any of claims 175 or 214, further comprising a collagenase inhibitor.

216. The IL-1i of claim 187, wherein said IL-1i is glycosylated.

217. A pharmaceutical composition comprising, in a pharmaceutically acceptable preparation, a therapeutically effective amount of the IL-1i of claim 216.

218. The IL-1i of claim 187, wherein said IL-1i is nonglycosylated.

219. A pharmaceutical composition comprising, in a pharmaceutically acceptable preparation, a therapeutically effective amount of the IL-1i of claim 218.

220. The IL-1i of claim 187, which consists of the following amino acid sequence:

(U) R P S G R K S S K M Q A F R I W D V N Q K T F
Y L R N N Q L V A G Y L Q G P N V N L E E K I D V
V P I E P H A L F L G I H G G K M C L S C V K S G
D E T R L Q L E A V N I T D L S E N R K Q D K R F
A F I R S D S G P T T S F E S A A C P G W F L C T
A M E A D Q P V S L T N M P D E G V M V T K F Y F
Q E D E wherein (U) is M or nothing.

221. A pharmaceutical composition comprising, in a pharmaceutically acceptable preparation, a therapeutically effective amount of the IL-1i of claim 220.

222. A method of treating a patient having arthritis comprising administering to the patient a therapeutically effective amount of an IL-1 inhibitor according to claim 220.

223. A method of treating a patient having rheumatoid arthritis comprising administering to the patient a therapeutically effective amount of an IL-1 inhibitor according to claim 220.

224. A method of treating a patient having osteoarthritis comprising administering to the patient a therapeutically effective amount of an IL-1 inhibitor according to claim 220.

225. A method of treating a patient to reduce an adverse effect of IL1 comprising administering to the patient a therapeutically effective amount of an IL-1 inhibitor according to claim 220.

226. A method of treating a patient having at least one of the following:
Crohn's disease, ulcerative colitis, glomerulonephritis, or leukemia,
comprising administering to the patient a therapeutically effective amount of an IL-1 inhibitor according to claim 220.

227. The IL-1i of claim 187, wherein (U) is M.

228. A pharmaceutical composition comprising, in a pharmaceutically acceptable preparation, a therapeutically effective amount of the IL-1i of claim 227.

229. A method of treating a patient having arthritis comprising administering to the patient a therapeutically effective amount of an IL-1 inhibitor according to claim 227.

230. A method of treating a patient having rheumatoid arthritis comprising administering to the patient a therapeutically effective amount of an IL-1 inhibitor according to claim 227.

231. A method of treating a patient having osteoarthritis comprising administering to the patient a therapeutically effective amount of an IL-1 inhibitor according to claim 227.

232. A method of treating a patient to reduce an adverse effect of IL1 comprising administering to the patient a therapeutically effective amount of an IL-1 inhibitor according to claim 227.

233. A method of treating a patient having at least one of the following:
Crohn's disease, ulcerative colitis, glomerulonephritis, or leukemia,
comprising administering to the patient a therapeutically effective amount of an IL-1 inhibitor according to claim 227.

234. The IL-1i of claim 227, wherein said IL-1i is nonglycosylated.

235. A pharmaceutical composition comprising, in a pharmaceutically acceptable preparation, a therapeutically effective amount of the IL-1i of claim 234.

236. A method of treating a patient having arthritis comprising administering to the patient a therapeutically effective amount of an IL-1 inhibitor according to claim 234.

237. A method of treating a patient having rheumatoid arthritis comprising administering to the patient a therapeutically effective amount of an IL-1 inhibitor according to claim 234.

238. A method of treating a patient having osteoarthritis comprising administering to the patient a therapeutically effective amount of an IL-1 inhibitor according to claim 234.

239. A method of treating a patient to reduce an adverse effect of IL-1 comprising administering to the patient a therapeutically effective amount of an IL-1 inhibitor according to claim 234.

240. A method of treating a patient having at least one of the following:
Crohn's disease, ulcerative colitis, glomerulonephritis, or leukemia,
comprising administering to the patient a therapeutically effective amount of an IL-1 inhibitor according to claim 234.

241. The IL-1i of claim 234, wherein the IL-1i is recombinantly made by an *E. coli* host cell.

242. A pharmaceutical composition comprising, in a pharmaceutically acceptable preparation, a therapeutically effective amount of the IL-1i of claim 241.

243. A method of treating a patient having arthritis comprising administering to the patient a therapeutically effective amount of an IL-1 inhibitor according to claim 241.

244. A method of treating a patient having rheumatoid arthritis comprising administering to the patient a therapeutically effective amount of an IL-1 inhibitor according to claim 241.

245. A method of treating a patient having osteoarthritis comprising administering to the patient a therapeutically effective amount of an IL-1 inhibitor according to claim 241.

246. A method of treating a patient to reduce an adverse effect of IL-1 comprising administering to the patient a therapeutically effective amount of an IL-1 inhibitor according to claim 241.

247. A method of treating a patient having at least one of the following:
Crohn's disease, ulcerative colitis, glomerulonephritis, or leukemia,
comprising administering to the patient a therapeutically effective amount of an IL-1 inhibitor according to claim 241.

248. The IL-1i of claim 241 having a purity of at least about 90%.

249. A pharmaceutical composition comprising, in a pharmaceutically acceptable preparation, a therapeutically effective amount of the IL-1i of claim 248.

250. A method of treating a patient having arthritis comprising administering to the patient a therapeutically effective amount of an IL-1 inhibitor according to claim 248.

251. A method of treating a patient having rheumatoid arthritis comprising administering to the payment a therapeutically effective amount of an IL-1 inhibitor according to claim 248.

252. A method of treating a patient having osteoarthritis comprising administering to the patient a therapeutically effective amount of an IL-1 inhibitor according to claim 248.

253. A method of treating a patient to reduce an adverse effect of IL1 comprising administering to the patient a therapeutically effective amount of an IL-1 inhibitor according to claim 248.

254. A method of treating a patient having at least one of the following:
Crohn's disease, ulcerative colitis, glomerulonephritis, or leukemia,
comprising administering to the patient a therapeutically effective amount of an IL-1 inhibitor according to claim 248.

255. The IL-1i of claim 241 having a purity of at least about 95%.

256. A pharmaceutical composition comprising, in a pharmaceutically acceptable preparation, a therapeutically effective amount of the IL-1i of claim 255.

257. A method of treating a patient having arthritis comprising administering to the patient a therapeutically effective amount of an IL-1 inhibitor according to claim 255.

258. A method of treating a patient having rheumatoid arthritis comprising administering to the patient a therapeutically effective amount of an IL-1 inhibitor according to claim 255.

259. A method of treating a patient having osteoarthritis comprising administering to the patient a therapeutically effective amount of an IL-1 inhibitor according to claim 255.

260. A method of treating a patient to reduce an adverse effect of IL-1 comprising administering to the patient a therapeutically effective amount of an IL-1 inhibitor according to claim 255.

261. A method of treating a patient having at least one of the following:
Crohn's disease, ulcerative colitis, glomerulonephritis, or leukemia, comprising administering to the patient a therapeutically effective amount of an IL-1 inhibitor according to claim 255.

262. The IL-1i of claim 220, wherein the IL-1i is recombinantly made by a Chinese hamster ovary cell.

263. The IL-1i of claim 220 having a purity of at least about 90%.

264. A pharmaceutical composition comprising, in a pharmaceutically acceptable preparation, a therapeutically effective amount of the IL-1i of claim 263.

265. A method of treating a patient having arthritis comprising administering to the patient a therapeutically effective amount of an IL-1 inhibitor according to claim 263.

266. A method of treating a patient having rheumatoid arthritis comprising administering to the patient a therapeutically effective amount of an IL-1 inhibitor according to claim 263.

267. A method of treating a patient having osteoarthritis comprising administering to the patient a therapeutically effective amount of an IL-1 inhibitor according to claim 263.

268. A method of treating a patient to reduce an adverse effect of IL1 comprising administering to the patient a therapeutically effective amount of an IL-1 inhibitor according to claim 263.

269. A method of treating a patient having at least one of the following:

Crohn's disease, ulcerative colitis, glomerulonephritis, or leukemia, comprising administering to the patient a therapeutically effective amount of an IL-1 inhibitor according to claim 263.

270. The IL-1i of claim 263, wherein said IL-1i is glycosylated.

271. A pharmaceutical composition comprising, in a pharmaceutically acceptable preparation, a therapeutically effective amount of the IL-1i of claim 270.

272. A method of treating a patient having arthritis comprising administering to the patient a therapeutically effective amount of an IL-1 inhibitor according to claim 270.

273. A method of treating a patient having rheumatoid arthritis comprising administering to the patient a therapeutically effective amount of an IL-1 inhibitor according to claim 270.

274. A method of treating a patient having osteoarthritis comprising administering to the patient a therapeutically effective amount of an IL-1 inhibitor according to claim 270.

275. A method of treating a patient to reduce an adverse effect of IL1 comprising administering to the patient a therapeutically effective amount of an IL-1 inhibitor according to claim 270.

276. A method of treating a patient having at least one of the following:

Crohn's disease, ulcerative colitis, glomerulonephritis, or leukemia, comprising administering to the patient a therapeutically effective amount of an IL-1 inhibitor according to claim 270.

277. The IL-1i of claim 220 having a purity of at least about 95%.

278. A pharmaceutical composition comprising, in a pharmaceutically acceptable preparation, a therapeutically effective amount of the IL-1i of claim 277.

279. A method of treating a patient having arthritis comprising administering to the patient a therapeutically effective amount of an IL-1 inhibitor according to claim 277.

280. A method of treating a patient having rheumatoid arthritis comprising administering to the patient a therapeutically effective amount of an IL-1 inhibitor according to claim 277.

281. A method of treating a patient having osteoarthritis comprising administering to the patient a therapeutically effective amount of an IL-1 inhibitor according to claim 277.

282. A method of treating a patient to reduce an adverse effect of IL1 comprising administering to the patient a therapeutically effective amount of an IL-1 inhibitor according to claim 277.

283. A method of treating a patient having at least one of the following:

Crohn's disease, ulcerative colitis, glomerulonephritis, or leukemia, comprising administering to the patient a therapeutically effective amount of an IL-1 inhibitor according lo claim 277.

284. The IL-1i of claim 277, wherein the IL-1i is recombinantly made by a eukaryotic host cell.

285. The IL-1i of claim 277, wherein said IL-1i is glycosylated.

286. A pharmaceutical composition comprising, in a pharmaceutically acceptable preparation, a therapeutically effective amount of the IL-1i of claim 285.

287. A method of treating a patient having arthritis comprising administering to the patient a therapeutically effective amount of an IL-1 inhibitor according to claim 285.

288. A method of treating a patient having rheumatoid arthritis comprising administering to the patient a therapeutically effective amount of an IL-1 inhibitor according to claim 285.

289. A method of treating a patient having osteoarthritis comprising administering to the patient a therapeutically effective amount of an IL-1 inhibitor according to claim 285.

290. A method of treating a patient to reduce an adverse effect of IL1 comprising administering to the patient a therapeutically effective amount of an IL-1 inhibitor according to claim 285.

291. A method of treating a patient having at least one of the following:

Crohn's disease, ulcerative colitis, glomerulonephritis, or leukemia, comprising administering to the patient a therapeutically effective amount of an IL-1 inhibitor according to claim 285.

292. The IL-1i of claim 277, wherein the IL-1i is recombinantly made by a mammalian host cell.

293. A pharmaceutical composition comprising, in a pharmaceutically acceptable preparation, a therapeutically effective amount of the IL-1i of claim 292.

294. The IL-1i of claim 277, wherein the IL-1i is recombinantly made by a prokaryotic host cell.

295. A method of any one of claims 4–6, 11–13, 36–38, 73–75, 80–82, 87–89, 94–96, 101–103, 108–110, 116–118, 123–125, 130–132, and 138–140, further comprising administering to the patient a therapeutically effective amount of a collagenase inhibitor.

296. A method of any one of claims 156–158, 163–165, 189–191, 222–224, 229–231, 236–238, 243–245, 250–252, 257–259, 265–267, 272–274, 279–281, and 287–289, further comprising administering to the patient a therapeutically effective amount of a collagenase inhibitor.

* * * * *